(12) United States Patent
Jinno

(10) Patent No.: US 9,532,794 B2
(45) Date of Patent: *Jan. 3, 2017

(54) MEDICAL MANIPULATOR

(71) Applicant: Karl Storz GmbH & Co. KG, Tuttlingen (DE)

(72) Inventor: Makoto Jinno, Fujinomiya (JP)

(73) Assignee: Karl Storz GmbH & Co. KG, Tuttlingen (DE)

( * ) Notice: Subject to any disclaimer, the term of this patent is extended or adjusted under 35 U.S.C. 154(b) by 602 days.

This patent is subject to a terminal disclaimer.

(21) Appl. No.: 13/922,896

(22) Filed: Jun. 20, 2013

(65) Prior Publication Data

US 2013/0282051 A1 Oct. 24, 2013

Related U.S. Application Data

(63) Continuation of application No. 12/717,665, filed on Mar. 4, 2010, now Pat. No. 8,500,721.

(30) Foreign Application Priority Data

Mar. 4, 2009 (JP) .................................. 2009-50474

(51) Int. Cl.
*A61B 17/29* (2006.01)
*A61B 17/00* (2006.01)

(52) U.S. Cl.
CPC .......... *A61B 17/2909* (2013.01); *A61B 34/70* (2016.02); *A61B 17/29* (2013.01); *A61B 2017/0046* (2013.01); *A61B 2017/00398* (2013.01); *A61B 2034/305* (2016.02); *A61B 2034/742* (2016.02)

(58) Field of Classification Search
CPC . A61B 19/22; A61B 2019/2234; A61B 17/29; A61B 17/2909; A61B 2017/00398; A61B 2017/0046
USPC ........................................................ 606/1, 5
See application file for complete search history.

(56) References Cited

U.S. PATENT DOCUMENTS

| | | | | |
|---|---|---|---|---|
| 2,365,232 | A * | 12/1944 | Wert | B24B 23/02 451/359 |
| 3,739,923 | A | 6/1973 | Totsuka | |
| 3,784,031 | A | 1/1974 | Niitu et al. | |
| 3,802,420 | A * | 4/1974 | Moffat | A61C 17/26 15/28 |
| 5,254,126 | A * | 10/1993 | Filipi | A61B 17/0469 606/139 |
| 5,591,170 | A | 1/1997 | Spievack et al. | |
| 5,702,420 | A * | 12/1997 | Sterling | A61B 17/32002 30/228 |

(Continued)

Primary Examiner — Gary Jackson
Assistant Examiner — Nathan J Jenness
(74) Attorney, Agent, or Firm — Whitmyer IP Group LLC

(57) ABSTRACT

A medical manipulator is provided. The medical manipulator includes an end effector that is configured to perform motions with respect to at least two different axes, and that is inserted in a body cavity during operation of the medical manipulator. The medical manipulator also includes at least two cylindrical motors that each include a longitudinal axis and that drive at least a part of the end effector. The motors remain outside a living body during operation of the medical manipulator and the motors are mounted on at least one bracket. A shaft interconnects the bracket and the end effector. A longitudinal axis of the shaft extends substantially parallel to each of the longitudinal axes of the motors.

16 Claims, 48 Drawing Sheets

(56) References Cited

U.S. PATENT DOCUMENTS

| | | | |
|---|---|---|---|
| 5,792,165 A | 8/1998 | Klieman et al. | |
| 5,954,731 A | 9/1999 | Yoon | |
| 6,394,998 B1* | 5/2002 | Wallace | A61B 19/2203 606/1 |
| 6,889,116 B2 | 5/2005 | Jinno | |
| 7,101,363 B2 | 9/2006 | Nishizawa et al. | |
| 7,208,005 B2 | 4/2007 | Frecker et al. | |
| 2003/0208187 A1* | 11/2003 | Layer | A61B 19/201 606/1 |
| 2004/0138667 A1* | 7/2004 | Kimura | A61B 17/1622 606/80 |
| 2006/0206100 A1* | 9/2006 | Eskridge | A61B 17/14 606/1 |
| 2006/0278681 A1* | 12/2006 | Viola | A61B 17/07207 227/176.1 |
| 2007/0233053 A1* | 10/2007 | Shelton | A61B 17/07207 606/1 |
| 2008/0103491 A1 | 5/2008 | Omori et al. | |
| 2008/0245175 A1 | 10/2008 | Jinno et al. | |

\* cited by examiner

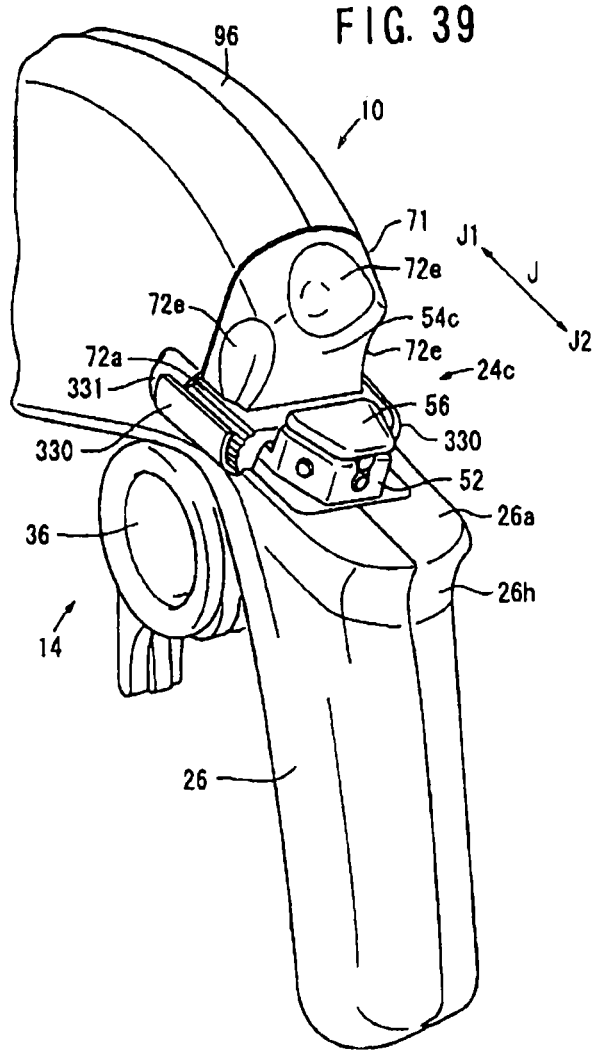

MEDICAL MANIPULATOR

CROSS-REFERENCE TO RELATED APPLICATIONS

This application is a continuation of U.S. application Ser. No. 12/717,665, filed Mar. 4, 2010, and is based upon and claims the benefit of priority from Japanese Application Number 2009-50474, filed Mar. 4, 2009, the entire contents of both of which are incorporated herein by reference.

BACKGROUND OF THE INVENTION

Field of the Invention

The present invention relates to a medical manipulator which has an end effector.

Description of the Related Art

In laparoscopic surgical operations, a few small holes are punctured in a patient's abdominal part or the like, an endoscope or a manipulator (or forceps) or the like is inserted into the abdominal cavity through the hole, and operators perform a surgical operation while viewing the endoscopic image. Such a laparoscopic surgical operation is expected to be applied to a broader range of fields, since it imposes little burden on the patient due to the absence of need for laparotomy and it largely reduces the number of days necessary for the patient to recover from the operation or to leave hospital.

On the other hand, a manipulator used in the laparoscopic surgical operation is desired to permit a swift and appropriate procedure according to the position and size of an affected part. Moreover, while using the manipulator, various procedures such as resection of an affected part, suture and ligation are conducted. In relation to such a surgical system, manipulators which have a high degree of freedom in operation and can be operated easily have been proposed (refer to, for example, U.S. Pat. No. 6,889,116, U.S. Patent Publication No. 2008/0103491 and U.S. Patent Publication No. 2008/0245175).

These manipulators in the related art each have an end effector that is inserted into the abdominal cavity to perform the desired procedure, an operating unit that is gripped and operated by the operator (generally, a surgeon), and a shaft interconnecting the end effector and the operating unit in a basic configuration. The operating unit includes a grip handle that is gripped by the operator, a plurality of motors that actuate the end effector, a trigger lever that gives a command relating to opening and closing actions of a gripper of the end effector, and other predetermined members.

In the manipulator described in the U.S. 2008/0103491, transmission of motive power from the motors to the end effector is conducted by use of wires, for example. Further, small-type motors are used in order to achieve a considerable reduction in weight.

SUMMARY OF THE INVENTION

According to one aspect, a medical manipulator includes an end effector that is configured to perform motions with respect to at least two different axes, and that is inserted in a body cavity during operation of the medical manipulator. The medical manipulator also includes at least two cylindrical motors that each include a longitudinal axis and that drive at least a part of the end effector. The motors remain outside a living body during operation of the medical manipulator and the motors are mounted on at least one bracket. A shaft interconnects the bracket and the end effector. A longitudinal axis of the shaft extends substantially parallel to each of the longitudinal axes of the motors.

In a further aspect, a medical manipulator includes an operating unit that includes a grip handle and an actuator block that includes at least two motors. The medical manipulator further includes a working unit that includes an end effector and an elongated hollow connector shaft that interconnects the end effector and the operating unit. The actuator block includes at least two motors that extend substantially parallel to a direction of extension of the connector shaft and that control at least one function of the end effector.

In a further aspect, A medical manipulator includes a working unit that includes an end effector and an elongated hollow connector shaft, and an operating unit that includes at least two actuator sets. Each actuator set includes a motor that operates at least one element of the end effector and extends substantially parallel to the connector shaft, the motor including a drive mechanism, and a drive shaft that extends substantially perpendicular to the motor, the drive shaft including a driven mechanism that engages the drive mechanism of the motor. The elongated hollow connector shaft interconnecting the end effector and the operating unit.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 39 is a perspective view of a misoperation preventive cover according to a third configuration example and the vicinity thereof;

DETAILED DESCRIPTION OF THE PREFERRED EMBODIMENTS

Figure 1:
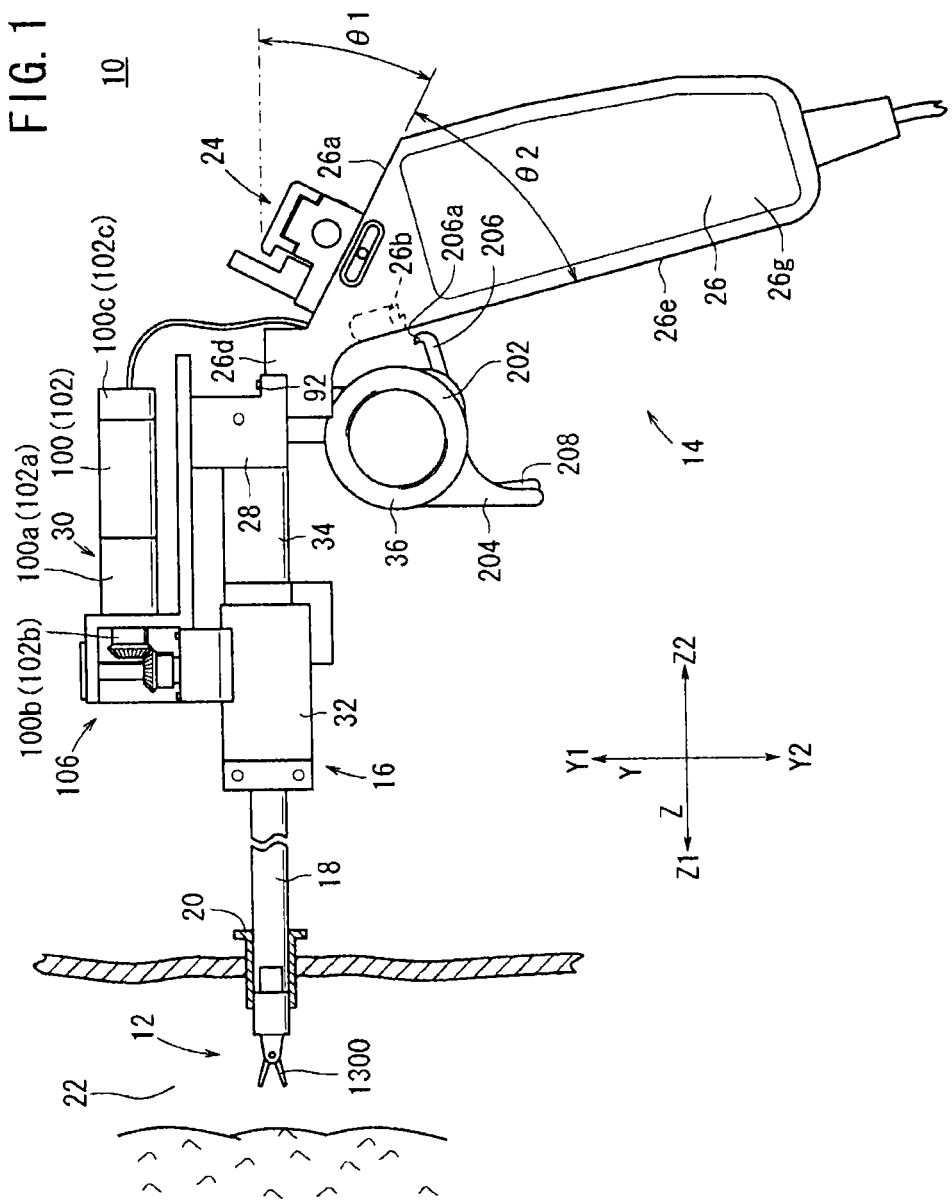
FIG. 1 is a side view of a medical manipulator.

Referring now to the drawings, wherein like reference numerals designate identical or corresponding parts throughout the several views.

Conventional ordinary forceps used in flexible-endoscopic operations and laparoscopic operations have a simple configuration in which a pair of finger insertion rings capable of being opened and closed are only provided at the proximal operating unit, and these forceps are much lighter in weight than the manipulator described in the U.S. 2008/0103491. Therefore, an operator accustomed to such conventional forceps may get a sense of discomfort in using the manipulator described in the U.S. 2008/0103491.

Particularly, in order to actuate the end effector through wires, it is appropriate to operate the wires by pulleys set vertical to the shaft. This approach, however, results in that the motors that rotate the pulleys necessarily protrude in a vertical direction from the shaft and, hence, have to be disposed remote from the grip handle which is gripped by the operator.

Consequently, a somewhat large moment due to the weight of the motors is generated on the grip handle, imposing a burden on the operator's hand.

Besides, depending on the procedure to be performed, there are cases where it is desired to put the grip handle as close as possible to a body surface of a patient. In such a situation, if the motors are disposed a little on the distal side of the grip handle and the trigger lever, the motors may contact the body surface or a trocar.

Further, if the motors are disposed to protrude over sideways from the shaft, the motor section may contact (interfere with) the endoscope (laparoscope) or other forceps or the like, thereby lowering the operability of the system.

Besides, while the conventional forceps have only an opening and closing axis, the end effector in the manipulators described in the U.S. Pat. No. 6,889,116 and the U.S. 2008/0103491 has a gripper that is opened and closed, a turning mechanism (an angular displacement mechanism) that turns the gripper in roll directions, and a pivot axis mechanism that tilts the gripper with reference to a predetermined pivot axis. Accordingly, at least three input units corresponding to these components of the manipulator are required.

An operator accustomed to the conventional forceps must learn how to operate the three input units, but the methods for operating the manipulators described in the U.S. Pat. No. 6,889,116 and the U.S. 2008/0103491 are not simple. Especially, it may be impossible to intuitively understand the operations of the turning mechanism and the pivot axis mechanism.

The present invention has been made in consideration of the above-mentioned problems. Accordingly, it is an object of the present invention to provide a medical manipulator which is excellent in operability and which can alleviate the burden on the operator.

It is another object of the present invention to provide a medical manipulator which promises intuitive operability as to input units for a turning mechanism (an angular displacement mechanism) and a pivot-axis mechanism and which permits easy and appropriate use of these components according to the purpose.

In one exemplary aspect, a medical manipulator includes an end effector that is inserted in a body cavity and operable to perform motions with respect to at least two axes, at least two cylindrical motors that are provided outside a living body and are operable to drive at least a part of the end effector, and a connector shaft that connects the part where the motors are provided and the end effector. Each of the at least two motors and the connector shaft are so provided as to have their axes substantially parallel to each other.

When the motors that actuate the end effector are provided in parallel to the connector shaft, the degree of freedom in layout is enhanced and, for example, the motors can be disposed near a grip handle. As a result, mass concentration on the vicinity of the grip handle can be achieved, which alleviates the burden on the operator's hand and enhances operability of the manipulator. In addition, a moment of inertia about the connector shaft is reduced, which also enhances the operability. Since the motors do not protrude sideways, a compact structure is realized.

According to another aspect, the medical manipulator may have a grip handle that is gripped by a hand on the proximal side. When viewed from the side, the motors and the grip handle may be disposed on opposite sides of an axis of the connector shaft, and all of the at least two motors are juxtaposed in the direction away from the viewer of the side view.

In the part on the proximal side of the medical manipulator, the motors and the grip handle are comparatively large in weight and volume. Where the motors and the grip handle with such characteristics are disposed on opposite sides with reference to the axis of the connector shaft, good balance is ensured, the degree of freedom in layout is enhanced, and operability is further enhanced.

Here, the juxtaposed arraying in the direction away from the viewer of from a side of the manipulator is not limited to a perfectly juxtaposed array without any stagger. For example, where the motors are somewhat different in length, it suffices for the motors that are juxtaposed over at least half the length thereof.

The motors and the grip handle may be disposed on a proximal side relative to a proximal portion of the connector shaft. This results in that the motors and the grip handle are disposed close to each other, whereby further concentration of mass can be achieved and the operability is further enhanced.

According to another aspect, the medical manipulator may further include rotators which are provided for each respective motor. The rotators include center axes that extend in a direction orthogonal to the array direction of the motors and the axial direction of extension of the motors. The rotators are disposed on extension lines of the axial directions of the motors, and are driven to rotate by the motors through a drive bevel gear and a driven bevel gear.

Two flexible members that are partly wrapped around a respective one of the rotators, pass through the connector shaft so as to transmit motive power to the end effector. The medical manipulator further includes a guide unit that guides the two flexible members to a proximal opening of the connector shaft. As a result of this configuration, the motors can be juxtaposed even when they are larger in diameter than the connector shaft. In addition, the degree of freedom in layout of the motors is enhanced, and the connector shaft can be made to be sufficiently slender, independently from the motor diameter.

It is preferable, from the viewpoint of balance, that the two sets of the motor and the rotator are provided at symmetrical positions with reference to the connector shaft.

Where the guide unit is a pulley having its axis parallel to the axis of the rotator, frictionless motions can be achieved.

In the medical manipulator, the flexible member may include a forward line and a return line, and the pulley may have a two-layer structure in which the two layers correspond to the forward line and the return line, respectively, and the two layers can be rotated independently. With the forward line and the return line, a shaft part that is actuated in the end effector can be driven in both normal and reverse directions. While the forward line and the return line act in opposite directions, the corresponding two layers of pulleys permit frictionless motions.

The medical manipulator may have a configuration in which the rotator is rotatably borne by a pair of bearing members on opposite sides with reference to the area where the driven bevel gear is provided, the motor is fixed to a motor plate which interconnects the pair of bearing members, and an output shaft of the motor protrudes through a hole provided in the motor plate and is connected to the driven bevel gear through the drive bevel gear. The bearing members and the motor plate arranged in this manner make it possible to obtain a high rigidity notwithstanding the simple structure, and to stably hold the motors and the rotators.

Where reinforcement plates that interconnect the pair of bearing members and the motor plate respectively are provided between the two rotators, a further enhanced rigidity can be obtained.

Parts, around which the flexible members are wound, of the rotators and the guide unit may be provided in a cavity of a box into which a proximal portion of the connector shaft opens, and the rotators may be sealed air-tight in a rotatable manner, in relation to the cavity. This makes it possible to keep air-tight the inside of the connector shaft and the body cavity with which the connector shaft communicates.

The end effector may include an end effector shaft that performs a procedure and at least one attitude shaft that changes the direction of the end effector shaft, the attitude shaft may be driven by the motor, and the end effector shaft may be driven through an operation transmission unit by which an operation on a predetermined input unit by a hand is mechanically transmitted. Where the drive members are thus mechanically connected to the input units operated by a hand, the operator can sense securely and easily the external forces exerted on the end effector and the like. In addition, a motor that drives the end effector shaft is unnecessitated, whereby reductions in the number of motors and in weight are realized.

The operation transmission unit may include a rod protruding to the proximal side from the inside of the connector shaft, connected to the input unit, and made to advance and retract in the direction in which the connector shaft extends, and the rod may be sealed air-tight so as to be capable of advancing and retracting, in relation to the connector shaft and a space with which the connector shaft communicates. This ensures that the connector shaft and the inside of the body cavity with which the connector shaft communicates can be maintained in an air-tight fashion.

According to another aspect, there is provided a medical manipulator including: an end effector that is inserted into a body cavity and operable to perform motions; a turning mechanism provided at the end effector and capable of turning about an axis along which the end effector extends; at least two motors provided in the exterior of a living body and operable to actuate at least a part of the end effector; a connector shaft that interconnects a part where the motors are provided and the end effector; a pivot axis mechanism provided at the end effector and capable of tilting in non-parallel to an axis which extends from the proximal side toward the distal side of the connector shaft; an operating unit including a grip handle that is gripped by a hand on the proximal side; a rotation operating part turned in a circumferential direction by a finger and operable to actuate the turning mechanism; and a tilt operating part tilted through being pushed in by a finger and operable to actuate the pivot axis mechanism; wherein an outer peripheral surface of the rotation operating part is provided with a finger holder on the radially outer side relative to an end portion or upper portion of the tilt operating part.

According to the turning input unit thus provided with the finger holder at an outer peripheral surface thereof, a turning operation about an axis of rotation can be performed, and intuitive operability as to the turning mechanism can be obtained. In addition, with the finger holder provided on the radially outer side relative to an end portion of the tilt operating part, the rotation operating part and the tilt operating part can easily be used appropriately according to the purpose. Here, the expression "finger holder" is used in a broadest sense, including a finger rest and the like. Besides, the respective correspondence of these operations with the turning mechanism and the pivot axis mechanism can be easily understood based on the difference in operating method between turning along the circumferential direction and tilting by pushing-in.

Let the thumb placing side (a Y1 side) in the grip handle on the upper side, then the rotation operating part and the tilt operating part may be provided at an upper-side end portion of the grip handle, and, in side view, the axes of rotation of the rotation operating part and the tilt operating part may be oriented upward toward the distal end (toward a Z1 side). Consequently, turning of the rotation operating part and the tilt operating part while gripping the grip handle is facilitated.

The axis of rotation of the rotation operating part may be at an angle of from 20° to 35° relative to the axis of the connector shaft, whereby a further easier operation is promised.

The tilt operating part may be tilted in left-right directions with reference to an axis parallel to the axis of rotation of the rotation operating part, whereby operability is enhanced.

The angles of the axes of rotation of the rotation operating part and the tilt operating part relative to the direction in which the grip handle extends may be from 40° to 60°, whereby operability is further enhanced. Here, the expression "the direction in which the grip handle extends" is defined by the direction of an edge line (where the edge line is a curved line, an average line of the curved edge line) on the side (a Z1 side) facing the end effector.

The rotation operating part and the tilt operating part may be unitized into an integral composite input unit, the position of which may be adjustable along the direction in which the rotational axis of the rotation operating part or the rotational axis of the tilt operating part extends. This makes it possible to cope with individual differences in finger length and the like.

When it is assumed that, in the plane containing both the direction in which the connector shaft extends and the direction in which the grip handle extends, the outward direction orthogonal to the axis of rotation of the rotation operating part is made to be an input unit outward direction, then the rotational axis of the rotation operating part, the rotational axis of the tilt operating part, and the operating surface of the tilt operating part that is operated by a finger may be arranged in this order along the input unit outward direction. This facilitates the configurations of the rotation operating part and the tilt operating part, and enhances the operability of the tilt operating part. In addition, due to the stagger between the axes of rotation, the rotation operating part and the tilt operating part give different tactile sensation when operated and, therefore, these parts can easily be used appropriately according to the purpose.

The finger holder may be provided on the outer side in the left-right directions of the tilt operating part. As a result, appropriate use of the rotation operating part and the tilt operation part according to the purpose is facilitated, and the turning input unit can be easily operated in the circumferential direction.

The tilt operating part may be provided so as to cover an upper portion of a part of the rotation operating part. This ensures that the rotation operating part and the tilt operating part are arranged in a compact form and are easy to operate.

The tilt operating part may be disposed on the proximal side of the rotation operating part, and the finger holder may be provided at an arcuate part larger in diameter than the tilt operating part, as viewed from the axial direction of the rotation operating part. This further facilitates the appropriate use of the rotation operating part and the tilt operating part. The arcuate part enlarged in diameter to a suitable extent is easy to operate, and, visually, the arcuate part can be intuitively understood as input mechanism of the turning mechanism. In addition, operations of the rotation operating part along the circumferential direction are facilitated.

A holding part that tiltably holds the tilt operating part may be provided with at least one input switch at a side surface portion thereof. This enhances operability of the at least one input switch.

The rotation operating part may be rotatable in normal and reverse directions from a predetermined reference position, and may be returned into the reference position by an elastic body when not operated. This permit the operator to intuitively understand the normal and reverse directions of the turning mechanism and the pivot axis mechanism.

When it is assumed that, in the plane containing both the direction in which the connector shaft extends and the direction in which the grip handle extends, the outward direction orthogonal to the axis of rotation of the rotation operating part is made that is the input unit outward direction, then the tilt operating part may have flat parts which are in left-right symmetry about the axis of rotation of the tilt operating part, as viewed from the input unit outward direction. This permits the operator to intuitively understand the operations in the normal and reverse directions of the pivot axis mechanism, and facilitates the tilting operation by pushing in with a finger.

The most distal end of the end effector shaft that performs a procedure may be actuated through an operation transmission unit by which a hand operation on a predetermined input unit is transmitted mechanically. With the driving member thus mechanically connected to the input unit which is operated by hand, the operator can sense assuredly and easily the external forces exerted on the end effector and the like. Besides, a driving motor for the end effector shaft is no longer necessary, whereby reductions in the number of motors and in weight are realized.

The medical manipulator may further include a trigger lever as an input unit for the end effector shaft provided at the most distal end in the end effector that performs a procedure, and the trigger lever may be provided on the side opposite to the tilt operating part and the rotation operating part with reference to the grip handle.

The medical manipulator may further include a misoperation preventive cover which covers at least a part of the rotation operating part so as to prevent the rotation operating part from being operated erroneously. This ensures that even when a part, near the rotation operating part, of an upper portion of the manipulator is gripped or held by an operator, the misoperation preventive cover hinders the operator's hand from unintentionally touching the rotation operating part, so that the rotation operating part is prevented from being operated erroneously.

The misoperation preventive cover may be so configured as to cover an upper portion of the rotation operating part or a part of the upper portion. When a part, near the rotation operating part, of the upper portion of the medical manipulator is gripped or held by the operator, the upper portion of the rotation operating part is most liable to come close to the operator's hand. Therefore, with a first cover configured so as to cover an upper portion of the rotation operating part or a part of the upper portion, touch on the rotation operating part by the operator's hand is inhibited effectively.

The finger holder may be provided at an upper end portion of the rotation operating part, and the misoperation preventive cover may be so configured as to cover those parts of an upper portion of the rotation operating part which are located on both sides in the turning direction of the rotation operating part, leaving exposed the finger holder provided at the upper end portion of the rotation operating part. With the misoperation preventive cover thus structured so as to leave the finger holder exposed, the misoperation preventive cover does not act as an obstacle when the operator put a finger on the finger holder. Accordingly, misoperation on the rotation operating part can be prevented, without lowering the operability of the rotation operating part.

The rotation operating part may have an operating element provided with the finger holder, and side parts provided on the lower side of the operating element and bulging to left and right outer sides relative to the operating element. In addition, the operating part may be provided with protuberant parts bulging to left and right outer sides, at front side surfaces of the above-mentioned lever, and the lever may be located on the inner side in the left-right direction relative to the protuberant parts. This ensures that, even where the rotation operating part has the side parts bulging in the left-right directions, there is little possibility of the operator's hand touching the side part when a part, near the rotation operating part, of an upper portion of the medical manipulator is gripped or held by the operator. Thus, the rotation operating part can be restrained from being operated erroneously.

The rotation operating part may have an operating element provided with the finger holder, and a lever provided on the lower side of the operating element and bulging to left and right outer sides relative to the operating element. Besides, the misoperation preventive cover may be so configured as to cover at least a part of the lever. As a result, even where the rotation operating part has the lever, the misoperation preventive cover inhibits the operator's hand from touching the lever, so that the rotation operating part is prevented from being operated erroneously.

The medical manipulator may further include a misoperation preventive mechanism that prevents the rotation operating part from being operated erroneously. In addition, the misoperation preventive mechanism may be so configured as to unable an operation of the turning mechanism by the rotation operating part when the rotation operating part is in a first state, and to enable the operation of the turning mechanism by the rotation operating part when the rotation operating part is in a second state. This ensures that the turning mechanism is not operated when the rotation operating part is in the first state, and that the operation of the turning mechanism by the rotation operating part remains impossible unless the rotation operating part is put into the second state. Accordingly, the rotation operating part is effectively prevented from being operated erroneously.

The operating part may have a tact switch which actuates the turning mechanism when depressed, and the rotation operating part may normally be elastically biased toward a position corresponding to the second state. Besides, the first state may be a state in which the rotation operating part is in a non-operating position on a retracted side of a position where the tact switch can be depressed. Further, the second state may be a state in which the rotation operating part is in an operating position where the tact switch can be depressed. This ensures that, when the rotation operating part is in the non-operating position, the tact switch would not be depressed by the rotation operating part even if the rotation operating part is operated, and that the tact switch would not be depressed unless the rotation operating part is intentionally moved into the operating position by the operator. Therefore, it is possible to securely prevent the rotation operating part from being operated erroneously.

The rotation operating part may be so configured that it can be displaced in the direction of rotation of the rotation operating part, it normally is elastically biased backwards, and it is moved into the operating position when pushed forwards by a hand. This configuration ensures that, by the simple operation of pushing the rotation operating part forwards, it is possible to move the rotation operating part into the operating position and thereby to establish a state in which the turning mechanism can be actuated.

The rotation operating part may be so configured that it can be displaced in a plane containing both the direction in which the connector shaft extends and the direction in which the grip handle extends, in the inward and outward directions orthogonal to the axis of rotation of the rotation operating part, it normally is elastically biased outwards, and it is moved into the operating position when pushed inwards by a hand. This configuration ensures that, by the simple operation of pushing the rotation operating part inwards, it is possible to move the rotation operating part into the operating position and thereby to establish a state in which the turning mechanism can be actuated.

The misoperation preventive mechanism may further include a rotation stopper which inhibits rotation of the rotation operating part when the rotation operating part is located in the non-operating position. This configuration ensures that when the rotation operating part is located in the non-rotating position, rotation of the rotation operating part is inhibited by the rotation stopper, so that the rotation operating part is prevented from being moved from a neutral position to the operating position while being in rotation.

This, in turn, prevents the tact switch from being depressed unexpectedly. In addition, the operator intending to operate the rotation operating part can recognize that the rotation operating part is in the non-operating position, from the fact that the rotation operating part would not be rotated. In such a situation, therefore, the operator can easily understand that it is necessary to push the rotation operating part inwards in order to obtain a state in which the turning mechanism can be actuated.

According to the medical manipulator pertaining to the present invention, both the motors that drive the end effector and the connector shaft are provided in parallel to each other, whereby the degree of freedom in layout is enhanced, so that they can be disposed near the grip handle, for example. As a result, mass concentration into the vicinity of the grip handle is realized, whereby the burden on the operator's hand is reduced, and operability of the manipulator is enhanced. Besides, the moment of inertia about the connector shaft is reduced, which also enhances the operability. The motors do not protrude sideways, and a compact structure is realized.

In addition, according to the medical manipulator pertaining to the present invention, the turning input part provided with a finger holder at an outer peripheral surface thereof is provided, whereby a turning operation about an axis of rotation is performed, which promises intuitive operability as to the turning mechanism. Besides, the finger holder is provided on the radially outer side relative to an end portion of the tilt operating part, whereby appropriate use of the turning input part and the tilt operating part according to the purpose is achieved easily. Here, the expression "finger holder" is used in a broadest sense, including a finger rest and the like. Further, due to the difference in operating method between turning along the circumferential direction and tilting by pushing-in, the respective correspondence of these operations with the turning mechanism and the pivot axis mechanism can be understood easily.

Figure 2:
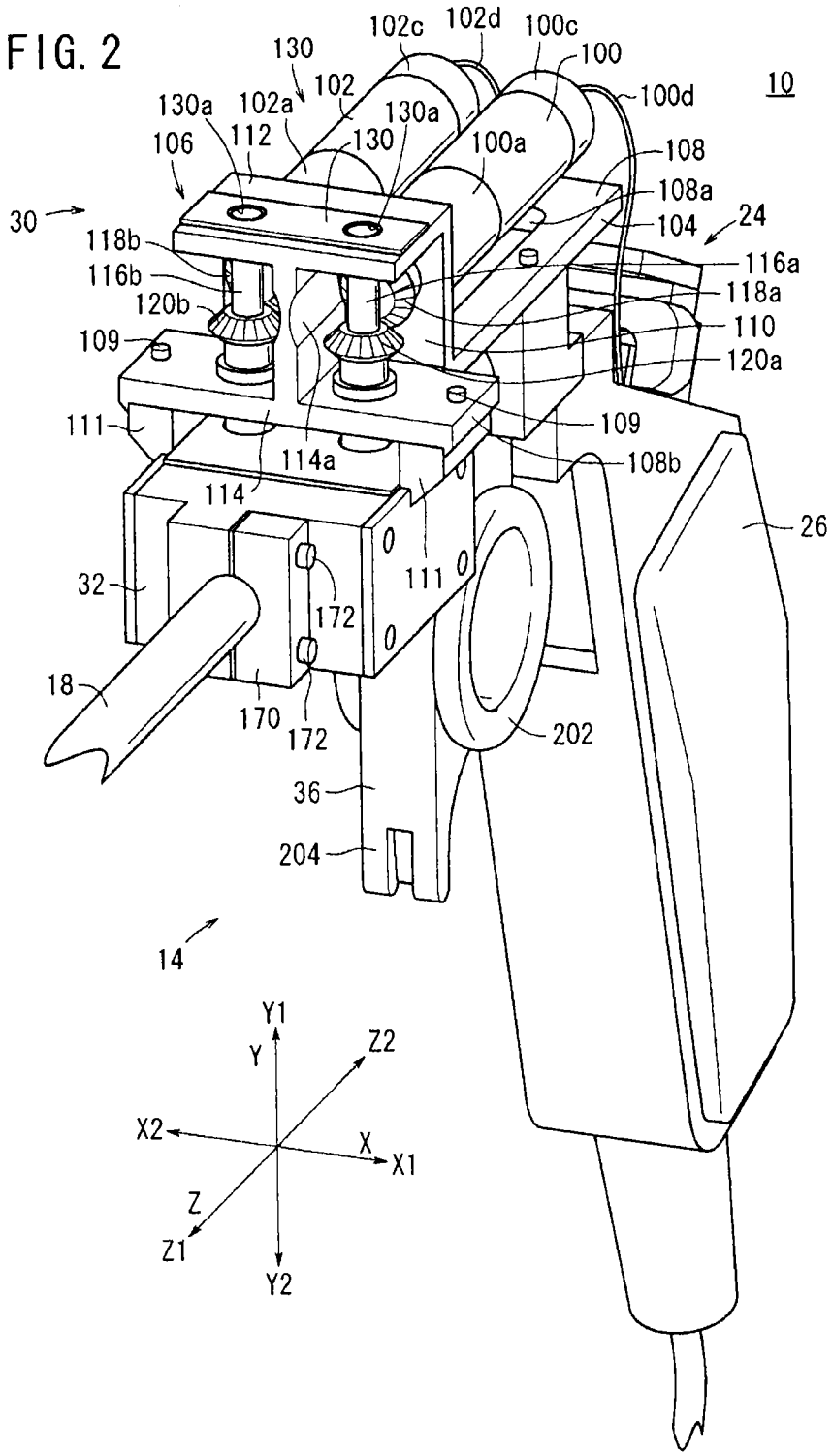
FIG. 2 is a partial enlarged perspective view of the medical manipulator.
Figure 3:
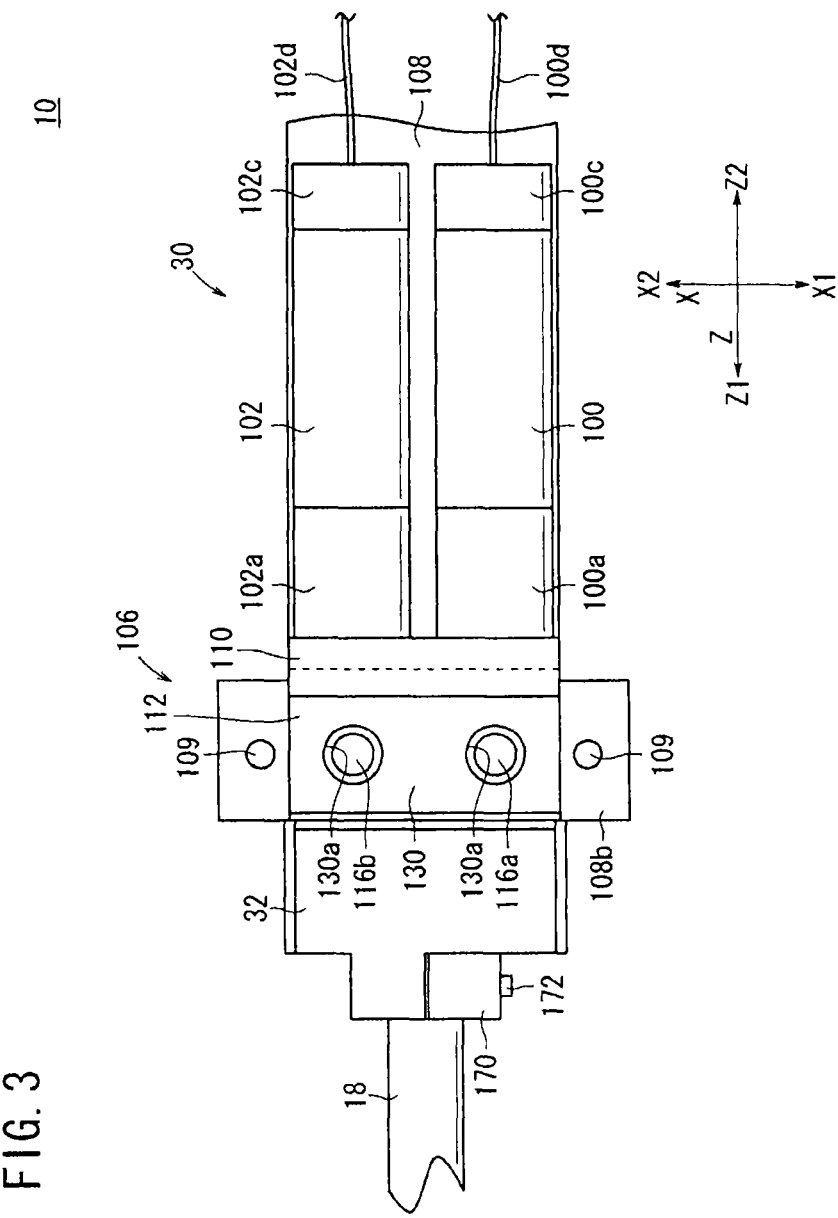
FIG. 3 is a partial enlarged plan view of the medical manipulator.

As shown in FIGS. 1, 2 and 3, the medical manipulator 10 (hereinafter referred to as the manipulator 10) according to this embodiment is an apparatus that grips a part of a living body or a curved needle or the like by an end effector 12 and performing a predetermined treatment, and is normally called also a gripping forceps, a needle driver (i.e., needle holder) and the like. The manipulator is a part of a manipulator system for medical use, and is controlled by a controller (not shown).

Incidentally, in FIGS. 1 to 3, a housing (i.e., cover) is omitted in the drawings so as to permit understanding of the inside structure, but, in practice, driving parts such as motors 100 and 102 are preferably accommodated in the inside of a housing (i.e., cover).

In the following description, the width direction in FIGS. 1 to 3 is defined as an X direction, the height direction is defined as a Y direction, and the direction in which a connector shaft 18 extends is defined as a Z direction. Besides, as viewed from the distal side, the rightward direction is defined as an X1 direction, the leftward direction as an X2 direction, the upward direction as a Y1 direction, the downward direction as a Y2 direction, the direction toward the viewer as a Z1 direction, and the direction away from the viewer as a Z2 direction. Further, unless otherwise specified, these directions are described based on the case where the manipulator 10 is laid in a neutral attitude. It should be noted here that these directions are for convenience of description and, naturally, the manipulator 10 may be used in arbitrary orientation (for instance, in the state of being set upside down).

As shown in FIGS. 1 to 3, the manipulator 10 has an operating unit 14 gripped and operated by a hand, and a working unit 16 fixed to the operating unit 14. The working unit 16 has an end effector 12 that performs work, and an elongated hollow connector shaft 18 interconnecting the end effector 12 and the operating unit 14. The end effector 12 and the connector shaft 18 are formed to be slender (small in diametral size), can be inserted into a body cavity 22 through a hollow cylindrical trocar 20 provided at a patient's abdominal part or the like, and can perform various procedures such as resection of an affected part, suture, ligation, etc. in the body cavity 22 in response to operations of a composite input unit 24. The operating unit 14 and the working unit 16 are united in this configuration, but they may be configured to be separable from each other according to the existing conditions.

The operating unit 14 includes a grip handle 26 to be gripped by a hand, a bridge 28 extending from an upper portion of the grip handle 26, and an actuator block 30 connected to the distal end of the bridge 28. The grip handle 26 has a length suitable for gripping by hand, and is provided with the composite input unit 24 on a slant surface 26a at an upper portion thereof. The grip handle 26 extends substantially in the Y2 direction from an end portion of the bridge 28; specifically, the grip handle 26 extends at an angle of about 75° with reference to the axis of the connector shaft 18. It has been confirmed that such an angle setting promises enhanced operability in moving the manipulator 10 as a whole and enhanced operability of the composite input unit 24.

The grip handle 26 is provided with a stepped engaging part 26b (see FIG. 1) in the inside of a hole formed at its end in the Z1 direction. The grip handle 26 is provided on both side surfaces thereof with grip plates 26g for enhancing holdability. The grip handle 26 is provided at its upper end portion with a left-right pair of joint pieces 26d that joins to the bridge 28.

The working unit 16 includes a pulley box 32 connected to the actuator block 30, the connector shaft 18 extending in the Z1 direction from the pulley box 32, the end effector 12 provided at the distal end of the connector shaft 18, a tubular part 34 extending in the Z2 direction from the pulley box 32, and a trigger lever 36 borne on the proximal side of the tubular part 34.

The end effector 12 can perform motions with respect to three axes, based on operations of the composite input unit 24 and the trigger lever 36. Specifically, these motions are yaw-axis motions of tilting with reference to the Y axis, roll-axis motions of rotating with reference to an axis oriented distally (the Z axis when the manipulator 10 is in the neutral attitude), and gripper-axis motions by which the end effector 12 can be opened and closed, in this order from the proximal side. The motions with respect to the yaw axis and the roll axis are electrically actuated based on operations on the composite input unit 24, while the motions with respect to the gripper axis are mechanically actuated based on operations on the trigger lever 36. The term "mechanically" here means a system of driving through wire, chain, timing belt, link, rod, gear or the like, principally, a system of driving through solid mechanical parts which are non-elastic in the direction in which motive power is transmitted. While wire, chain and the like may show some unavoidable elongation under tension, these are deemed as non-elastic solid mechanical parts here. A load limiter 212 to be described later is substantially free of elastic deformation during normal operation, and is essentially a non-elastic part.

Now, the components of the manipulator 10 will be described below, in the order of the composite input unit 24, the actuator block 30, the pulley box 32, the tubular part 34 and the trigger lever 36, and the end effector 12.

In the first place, the composite input unit 24 will be described. The composite input unit 24 has a structure which is symmetrical in the X1 direction and the X2 direction, with the Z axis as a center of symmetry, in plan view.

Figure 4:
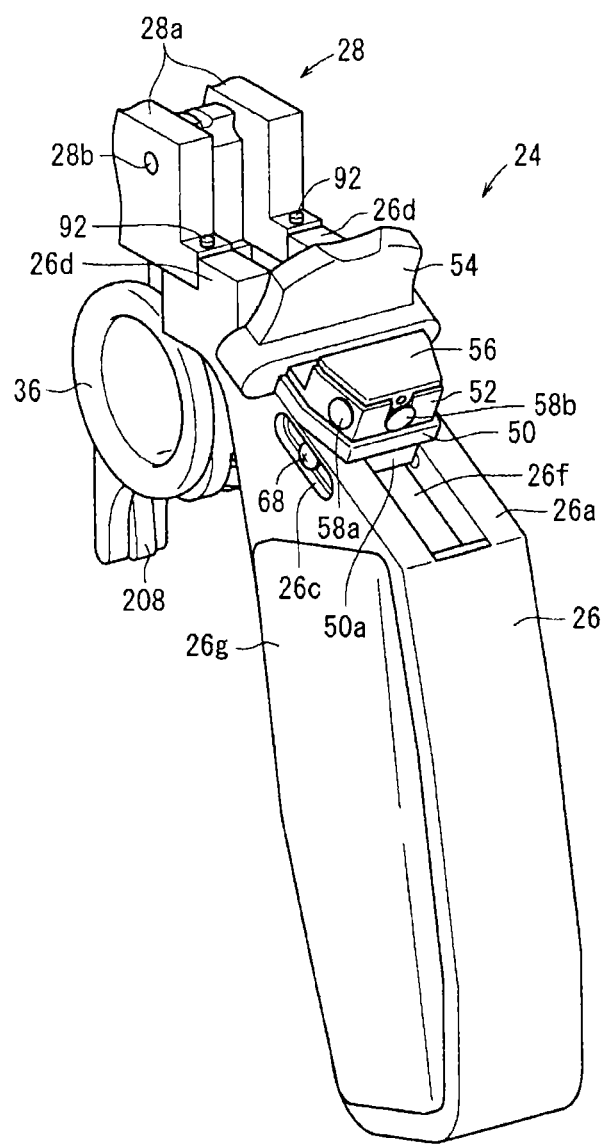
FIG. 4 is a perspective view of a grip handle, a composite input unit and the vicinity thereof in the medical manipulator.

As shown in FIG. 4, an upper surface of the grip handle 26 is a slant surface 26a rising in the Y1 direction toward the distal side, and the composite input unit 24 is provided on the slant surface 26a. The inclination angle θ1 of the slant surface 26a is an angle that permits easy operation of the composite input unit 24 by a thumb and/or an index finger when the grip handle 26 is gripped by a hand. Specifically, the inclination angle θ1 is preferably in the range of from 20° to 35° with respect to the Z direction.

For convenience of description, the inclination direction of the slant surface 26a (and an axis 70 and an axis 74, as well) will be referred to as J directions, of which the direction toward the distal side will be referred to as a J1 direction, and the direction toward the proximal side as a J2 direction. Besides, in the plane (ZY plane) containing the direction in which the connector shaft 18 extends and the direction in which the grip handle 26 extends, the direction orthogonal to the J directions will be referred to as K directions, of which the direction toward the outer side will be referred to as a K1 direction (input unit outward direction), and the direction toward the inner side as a K2 direction.

The slant surface 26a is provided in its central portion with a slide groove 26f extending in the Z directions in plan view. The grip handle 26 is provided, in both left-side and right-side surfaces of an upper portion thereof, with slots 26c which extend in the K directions and communicate with the slide groove 26f.

Figure 5:
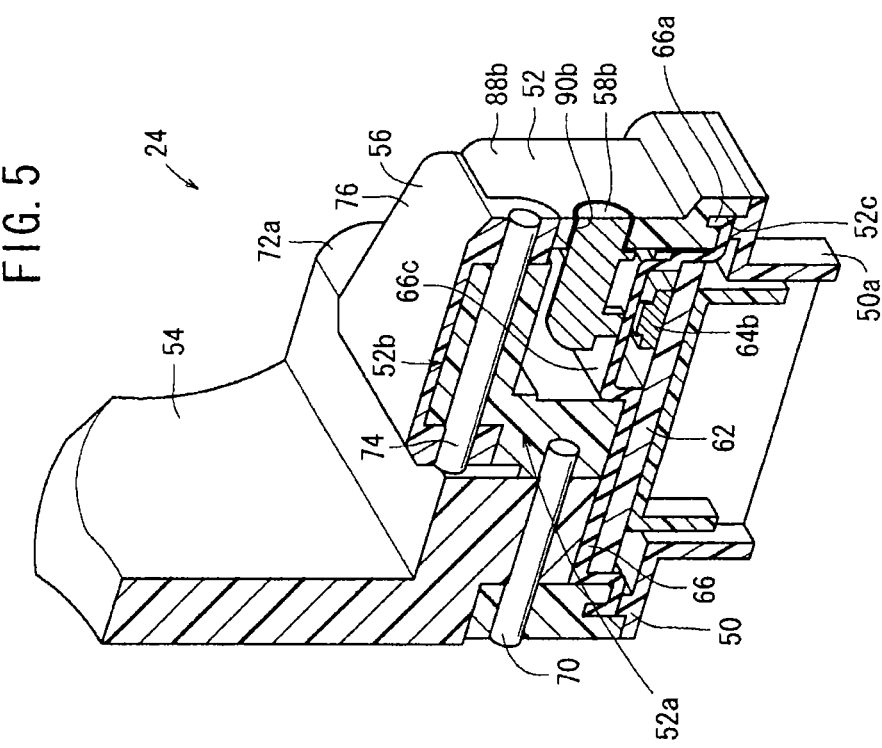
FIG. 5 is a partly sectional perspective view of the composite input unit.

As shown in FIGS. 4 and 5, the composite input unit 24 includes a base block 50 mounted on the slant surface 26a so as to be slidable in the J directions. In this example, the input unit 24 includes a lower portion 50a fitted in the slide groove 26f, a housing (holding part) 52 provided on the base block 50, a rotation operating part 54, a tilt operating part 56, and three switch operating elements (input switches) 58a, 58b and 58c. A switch board 62 and a silicone body 66 are provided inside the housing 52.

The switch operating element 58b can be used as a switch that changes over the rotation operating part 54 and the tilt operating part 56 between an effective state and an ineffective state, that returns a pivot axis mechanism into a predetermined initial attitude (when the switch operating element 58b is depressed once, the pivot axis mechanism is automatically moved into the initial attitude and stopped), or that moves the pivot axis mechanism toward the initial attitude (the pivot axis mechanism is moved toward the initial attitude only when the switch operating element 58b is being depressed, and the pivot axis mechanism is automatically stopped upon reaching the initial attitude).

Similarly, the switch operating elements 58a and 58c can be used as switches that return a rolling mechanism into a predetermined initial attitude, or that move the rolling mechanism toward the initial attitude. The switch operating elements 58a and 58c, as switches having quite the same functions, are disposed respectively on the left and right sides. This permits an operator to perform the same operations, without any problem, whether the operating unit 14 is gripped by a right hand or a left hand of the operator. Specifically, both in the case of a right-hand operation and in the case of a left-hand operation, the same operations can be performed by a thumb, for example. In addition, the operator can return the rolling mechanism into a predetermined initial attitude, or move the rolling mechanism toward the initial attitude, without being conscious of the current position (in a positive region or in a negative region) of the rolling mechanism.

Signals from these switches may be supplied to a controller independently as they are, or may be supplied as a serial signal together with other signals. It is preferable that at least one input switch is provided on each of side surfaces 88a, 88b and 88c of the housing 52.

Figure 9:
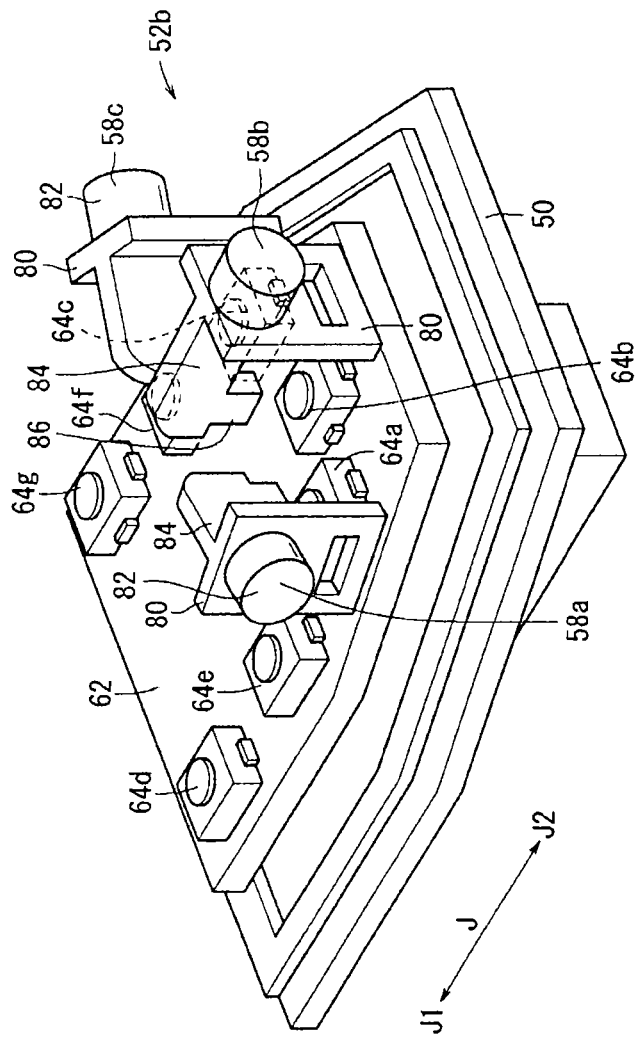
FIG. 9 is a perspective view of a switch board and switch operating elements in the composite input unit.

As shown in FIG. 9, the switch board 62 is fixed to an upper surface of the base block 50, and has seven tact switches 64a, 64b, 64c, 64d, 64e, 64f and 64g. The tact switches 64d and 64g are provided at left and right symmetrical positions on an end portion in the J1 direction of the switch board 62. The tact switches 64e and 64f are provided at left and right symmetrical positions, slightly on the J2 direction side relative to the tact switches 64d and 64g. The tact switches 64a and 64c are provided at left and right symmetrical positions, slightly on the J2 direction side relative to the tact switches 64e and 64g. The tact switch 64b is provided at a central position on the most J2 side. The switch board 62 has a pentagonal shape which is slightly narrowed on the J2 direction side, and the tact switches 64a to 64c are provided at mutually close positions according to the pentagonal shape.

The silicone body 66 is an elastic body, and has a dust-proofing and water-proofing function for the switch board 62 and a function that holds the rotation operating part 54 and the tilt operating part 56 in their neutral positions. The silicone body 66 covers an upper surface and side surfaces of the switch board 62, and has an upwardly warped flange 66a at its peripheral portion. The silicone body 66 has four individual bulging portions 66b corresponding respectively to the tact switches 64d, 64e, 64f and 64g, and a bulging portion 66c that covers the tact switches 64a to 64c collectively.

The flange 66a is fitted in a groove 52c provided in the lower surface of the housing 52 along a peripheral portion of the latter. Of the silicone body 66, the flange 66a and a portion on the inner side of the flange 66a are clamped and compressed between the base block 50 and the housing 52, whereby the water-proofing and dust-proofing actions are exhibited.

A lower portion 50a of the base block 50 is fixed by a screw 68 inserted through the slot 26c, and, when the screw 68 is untightened, the base block 50 can be moved along the slot 26c, that is, the position of the base block 50 can be adjusted. In this manner, the rotation operating part 54 and the tilt operating part 56 are unitized into the composite input unit, and the position of these parts as a whole can be adjusted along the direction in which a shaft 70 (or a shaft 74) extends. This configuration makes it possible to cope with individual differences in finger length and the like.

The housing 52 has a thin front portion 52a on the J1 direction side, and a thick rear portion 52b on the proximal side at which the switch operating elements 58a, 58b and 58c are provided. The rear portion 52b has a trapezoidal shape narrowed toward the J2 direction, in plan view.

The rotation operating part 54 is configured to be turnable about the shaft 70 provided in the front portion 52a. The shaft 70 is oriented in the J directions, and is positioned at the center of the composite input unit 24 with respect to the X directions. The rotation operating part 54 includes a lever 72a extending in the X1 direction and the X2 direction, a left-right pair of pressing protrusions 72*b* and 72*c* provided at a lower surface of the lever 72*a*, and a substantially semicircular, thin plate-like operating element 72*d* provided on the upper side of the lever 72*a*.

Figure 6:
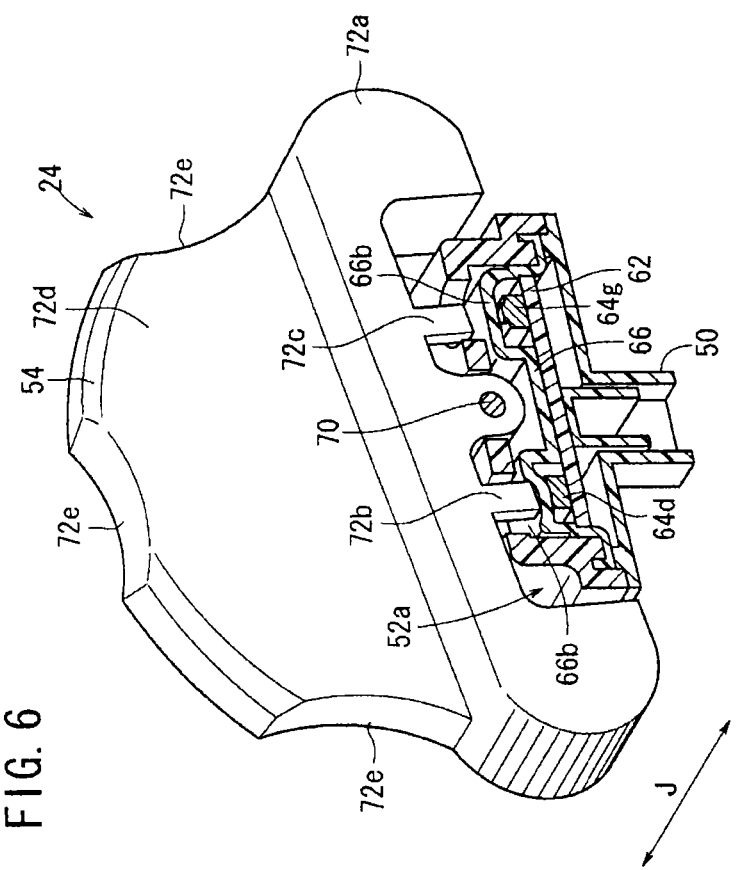
FIG. 6 is a longitudinal cross-sectional view of the pressing protrusions of a rotational operating part in the composite input unit.

As shown in FIG. 6, both left and right ends of the lever 72*a* are semicircular in shape and provided in the surfaces thereof with a multiplicity of anti-slip streaks. The outer peripheral surface of the operating element 72*d* is in the shape of an arc of a circle having a center substantially at the shaft 70 and a radius substantially equal to the distance from the shaft 70 to an end portion of the lever 72*a*, and is provided with shallow notches 72*e* that receive a finger thereon at an upper end and left and right ends thereof. The operating element 72*d* is protruding in a direction orthogonal to the J directions, in side view.

The rotation operating part 54 has a function of actuating a rolling mechanism when the operating element 72*d* is turned in the circumferential direction by a finger put in the notch 72*e*. According to the rotation operating part 54 thus provided with the finger holders at the outer peripheral surface thereof, a turning operation about the shaft 70 can be performed, and intuitive operability with respect to the rolling mechanism can be obtained. In addition, since the finger holders are provided on the radially outer side relative to the end portion of the tilt operating part 56, appropriate use of the rotation operating part 54 and the tilt operating part 56 according to the purpose can be realized easily.

The finger holders (or finger rests) of the rotation operating part 54 is not limited to notches in shape; the finger holder may be any one that includes a part which is provided in the outer peripheral surface at a position permitting a finger to be put thereon during supposed use and which has an area suitable that receives a finger thereon.

As shown in FIG. 6, tips of the pressing protrusions 72*b* and 72*c* are lightly touching the individual bulging portions 66*b* covering the tact switches 64*d* and 64*g*, respectively, whereby the rotation operating part 54 is held in a neutral position. When the rotation operating part 54 is turned in either direction by a finger operation, the pressing protrusion 72*b* or 72*c* can be lowered while elastically deforming the individual bulging portion 66*b*, to thereby turn on the tact switch 64*d* or 64*g*. The rotation operating part 54 is limited in rotational angle by its contact with an upper surface or a side surface of the front portion 52*a* of the housing 52, and, therefore, it would not excessively depress the tact switch 64*d* or the tact switch 64*g*. When the finger is released from the finger holder, the rotation operating part 54 is returned into the neutral position by the resilience of the individual bulging portion 66*b*, and the tact switch 64*d* or 64*g* is turned off.

Figure 7:
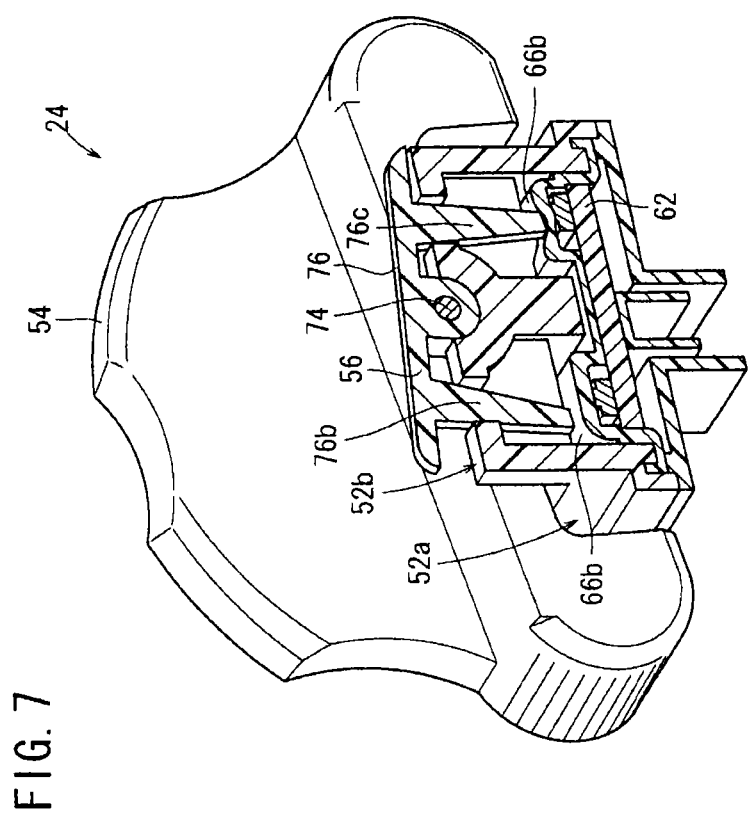
FIG. 7 is a longitudinal cross-sectional view of the pressing protrusions of a tilt operating part in the composite input unit.

As shown in FIGS. 5 and 7, the tilt operating part 56 is configured to be tiltable about the shaft 74 provided in the rear portion 52*b* of the housing 52. The shaft 74 is oriented in the J directions, and is positioned at the center of the composite input unit 24 with respect to the X directions. The shaft 74 is disposed to be slightly farther from the upper surface 26*a* (slant surface 26*a*) of the grip handle 26 than the shaft 70.

The tilt operating part 56 has a tilting plate 76 covering the upper side of the rear portion 52*b* of the housing 52, and a left-right pair of pressing protrusions 76*b* and 76*c* provided at a lower surface of the tilting plate 76. The gap between the lower surface of the tilting plate 76 and the upper surface of the rear portion 52*b* is small. The upper surface of the tilting plate 76 is provided with a multiplicity of anti-slipping streaks, and is trapezoidal in shape in plan view, like the rear portion 52*b*. The upper surface of the tilting plate 76 is slightly farther than from the upper surface 26*a* (slant surface 26*a*) of the grip handle 26 the lever 72*a*.

Tips of the pressing protrusions 76*b* and 76*c* are lightly touching the individual bulging portions 66*b* covering the tact switches 64*e* and 64*f*, respectively, whereby the tilt operating part 56 is held in a neutral position. When the tilt operating part 56 is turned in either direction by a finger operation, the pressing protrusion 76*b* or 76*c* can be lowered while elastically deforming the individual bulging portion 66*b*, to thereby turn on the tact switch 64*e* or 64*f*. The tilt operating part 56 is limited in tilt angle by its contact with an upper surface of the rear portion 52*b* of the housing 52, and, therefore, it would not excessively depress the tact switch 64*e* or the tact switch 64*f*. When the finger is released from the finger holder, the tilt operating part 56 is returned into the neutral position by the resilience of the individual bulging portion 66*b*, and the tact switch 64*e* or 64*f* is turned off.

The tilt operating part 56 has a function of actuating the pivot axis mechanism when a tilting operation is conducted by pushing in the tilting plate 76 by a finger.

The rotation operating part 54 is actuated by a turning operation along the circumferential direction of the rotation operating part 54, whereas the tilt operating part 56 is actuated by a tilting operation by pushing-in the tilt operating part 56. According to such a difference in operating method, the respective correspondence of the operations with the turning mechanism and the pivot axis mechanism can be understood easily.

In side view (see FIG. 1), the shaft 70 and the shaft 74 in the rotation operating part 54 and the tilt operating part 56 are oriented up toward the distal end (Z1 side), which permits the rotation operating part 54 and the tilt operating part 56 to be easily operated while gripping the grip handle 26. In addition, the shafts 70 and 74 are parallel to the J directions, and are at an angle of 20° to 35° with respect to the Z directions, which promises easy operation, particularly by a thumb.

Further, since the shaft 70 and the shaft 74 are parallel to each other, high operability is attained. In addition, where the angle θ2 (see FIG. 1) at which the shaft 70 and the shaft 74 are inclined with respect to the extending direction of the grip handle 26 is in the range of from 40° to 60°, a further enhanced operability is attained. Here, the extending direction of the grip handle 26 can be defined as the direction of an edge line 26*e* (an average line, in the case of a curved edge line) on the side (Z1 side) for facing the end effector.

Since the shaft 70, the shaft 74, and the tilting plate 76 as the operating surface for operating the tilt operating part 56 by a finger are arranged in this order along the K1 direction, the rotation operating part 54 and the tilt operating part 56 can be configured easily, and good operability is realized with respect to the tilt operating part 56. In addition, since the shaft 70 and the shaft 74 are mutually staggered, the rotation operating part 54 and the tilt operating part 56 give different feelings when operated, so that appropriate use of them according to the purpose can be realized easily.

The tilt operating part 56 is disposed on the proximal side of the rotation operating part 54, and the notches 72*e* as finger holders are provided in the operating element 72*d* having an arcuate shape which is greater in radius than the tilt operating part 56 as viewed in the J direction. This ensures that appropriate use of the rotation operating part 54 and the tilt operating part 56 according to the purpose can be realized more easily. The arcuate operating element 72*d* has an appropriately large radial size and, therefore, can be operated easily. Moreover, on a visual basis, the operating element 72d can be intuitively understood as input mechanism for the turning mechanism. In addition, operations of the rotation operating part 54 along the circumferential direction are easy to carry out.

Each of the rotation operating part 54 and the tilt operating part 56 can be rotated in normal and reverse directions from a predetermined reference position, and is returned into the reference position by the elastic body when not operated. This permits intuitive understanding of the operations of the rolling mechanism and the pivot axis mechanism in the normal and reverse directions.

Figure 8:
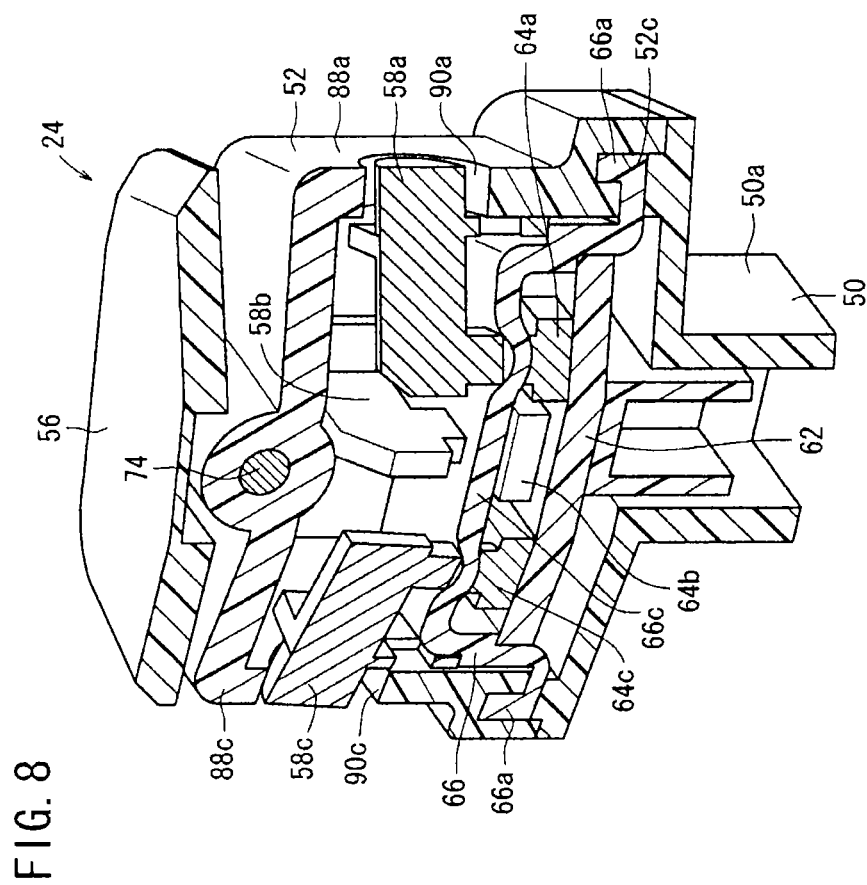
FIG. 8 is a sectional perspective view of a rear portion of the composite input unit.

As shown in FIGS. 8 and 9, switch operating elements 58a to 58c are accommodated in the rear portion 52b of the housing 52. The switch operating elements 58a to 58c are the same in configuration, and each have a quadrilateral frame 80 made of an elastic material, a cylindrical pusher 82 provided on one side of an upper portion of the quadrilateral frame 80, an arm 84 provided on the other side, and a protrusion 86 provided at the tip of the arm 84 and directed downwards.

A lower portion of the quadrilateral frame 80 is fixed by clamping (or by adhesion or the like) between the bulging portion 66c of the silicone body 60 and the inside wall of the housing 52. The respective protrusions 86 of the switch operating elements 58a to 58c are disposed on the upper side of the tact switches 64a, 64b and 64c, and are lightly touching the upper surface of the bulging portion 66c. The respective pushers 82 of the switch operating elements 58a to 58c protrude from holes 90a, 90b and 90c formed in side surfaces 88a, 88b and 88c on three sides (left and right side surfaces and a rear surface) of the rear portion 52b of the housing 51, in such an extent as to be pushable by a finger.

In this way, the switch operating elements 58a to 58c provided respectively at the left and right side surfaces and the rear surface of the housing 52 are high in operability, and they are oriented in different directions, which prevents them from being operated erroneously.

The side surface 88a on the X1 direction side and the side surface 88c on the X2 direction side are inclined so as to approach the center along the J2 direction, and the side surface 88b between them is a surface orthogonal to the J directions; in addition, these side surfaces are provided at such positions that they can each be easily operated by a thumb or an index finger when the grip handle 26 is gripped by a hand. The holes 90a to 90c are provided in substantially central portions of the side surfaces 88a to 88c, in order to permit easy operation.

When one of the pushers 82 protruding from the holes 90a to 90c is pushed by a finger, the quadrilateral frame 80 is elastically deformed, the arm 84 is tilted, and the protrusion 86 at the tip of the arm 84 is lowered while elastically deforming the bulging portion 66c, whereby the corresponding one of the tact switches 64a to 64c can be turned on. When the finger is released from the pusher 82, the corresponding one of the switch elements 58a to 58c is returned into its original position by resilience of the bulging portion 66c and the quadrilateral frame 80, whereby the relevant one of the tact switches 64a to 64c is turned off.

Incidentally, in FIG. 9, for ease of understanding, the silicone body 66 and the housing 52 are omitted, and the switch operating elements 58a to 58c are also shown in the state of floating in the air.

Figure 10:
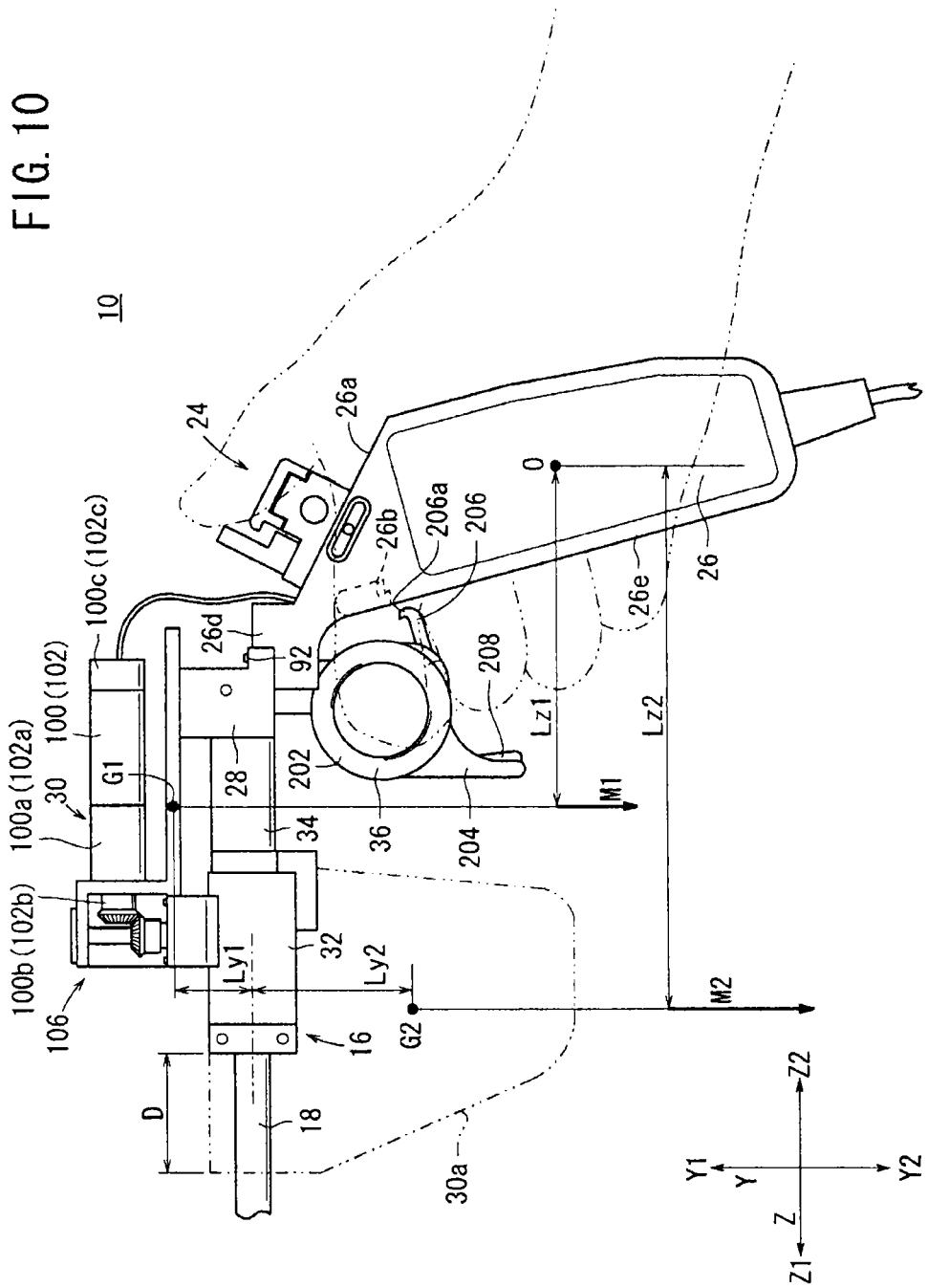
FIG. 10 is a side view of the medical manipulator in the condition where the grip handle is gripped by a hand.

The composite input unit 24 configured as above is set in such position and orientation as to permit easy operation by a thumb, in the condition where the grip handle 26 is gripped by a hand, as shown in FIG. 10. This permits respective operations of the rotation operating part 54, the tilt operating part 56, and the switch operating elements 58a, 58b and 58c to be carried out easily. Besides, in this condition, the trigger lever 36 can be naturally pushed and pulled by an index finger.

As is clear from FIG. 10, the trigger lever 36 is provided on the side opposite to the composite input unit 24 provided with the tilt operating part 56 and the rotation operating part 54, with reference to the grip handle 26. This permits the operator to operate the trigger lever 36 and the composite input unit 24 with different fingers while gripping the grip handle 26.

Figure 11:
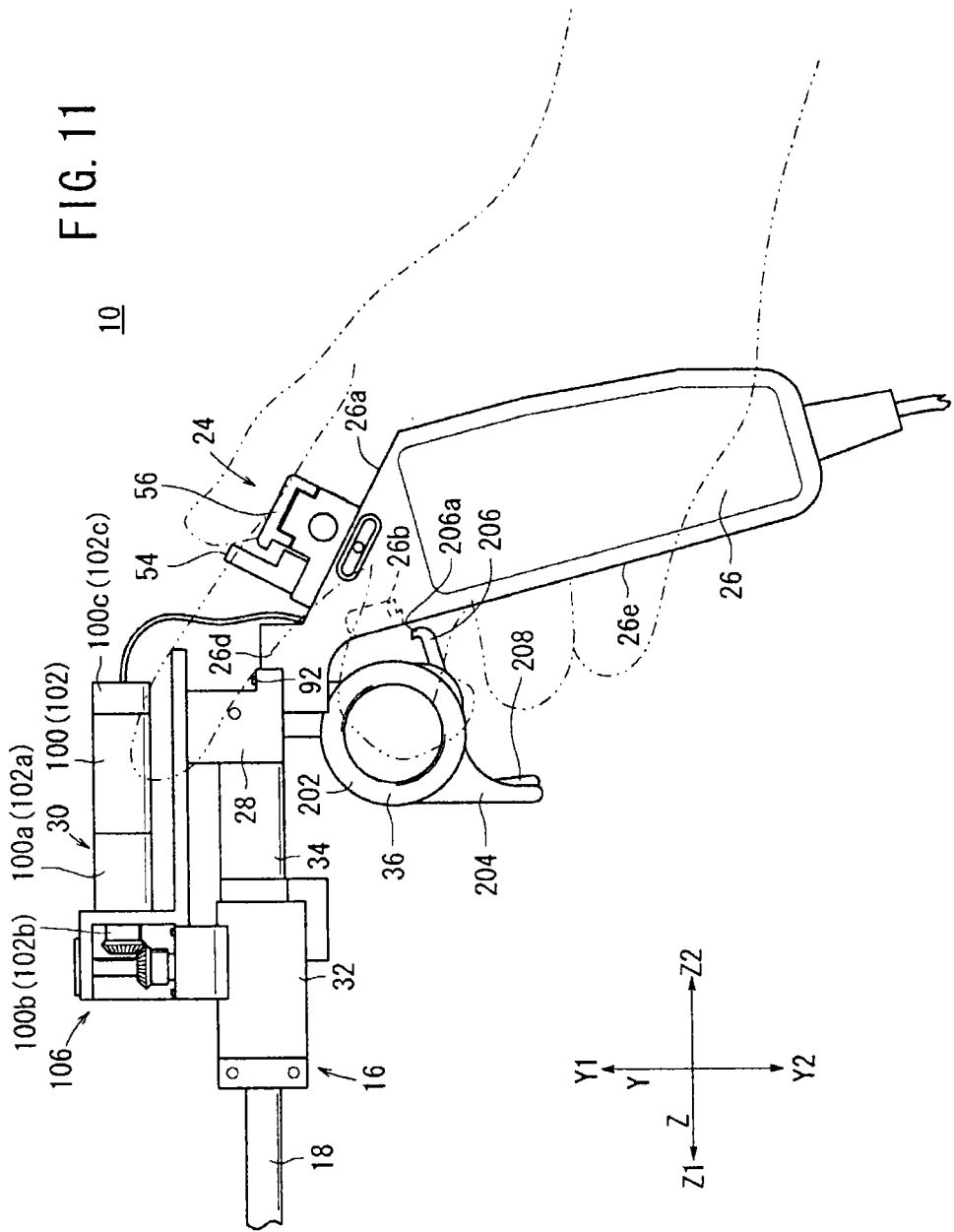
FIG. 11 is a side view of the medical manipulator in the condition where the grip handle is gripped by a hand so that simultaneous operations with respect to three axes can be performed.

In addition, for example, as shown in FIG. 11, an operating mode may be adopted in which the rotation operating part 54 is operated by an intermediate portion of an index finger, the tilt operating part 56 is operated by a thumb, and the trigger lever 36 is operated by an intermediate portion of the middle finger. In this operating mode, motions of the end effector 12 with respect to three axes can be actuated simultaneously and in harmony. While FIGS. 10 and 11 show an operation example in which the manipulator 10 is operated by a left hand, the manipulator 10 can also be operated by a right hand in substantially the same manner.

With respect to the rotation operating part 54, several modifications can be considered.

Figure 12:
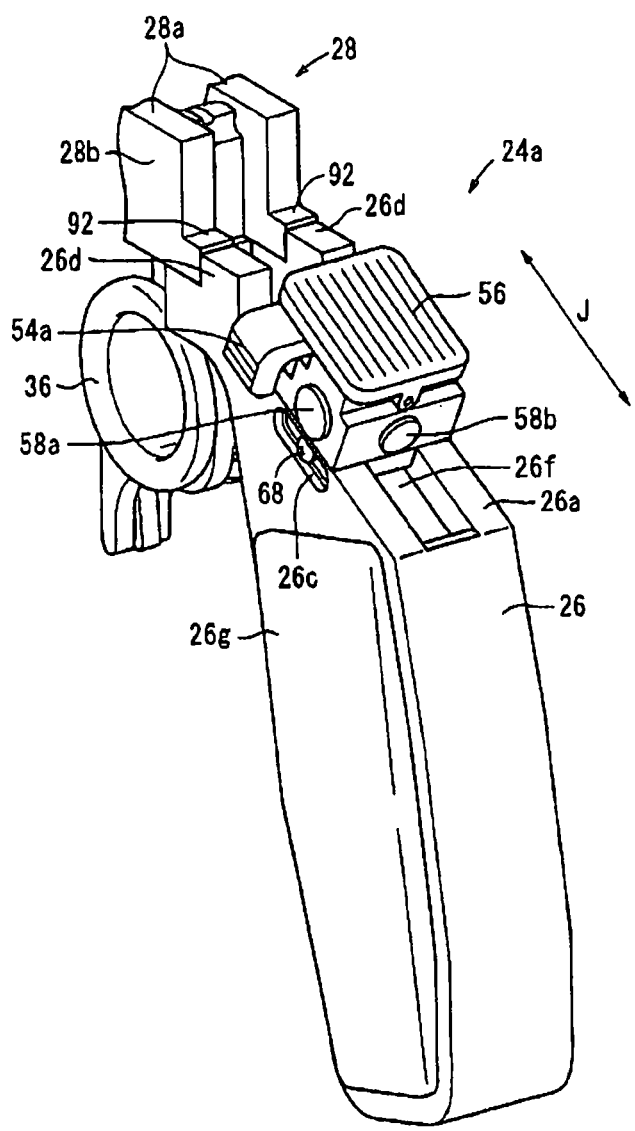
FIG. 12 is a perspective view of the grip handle, a composite input unit according to a first modification, and the vicinity thereof in the medical manipulator.

For instance, FIG. 12 shows a rotation operating part 54a of a composite input unit 24a according to a first modification. As shown in the figure, the rotation operating part may be of a lever system in which a lever extends in the left-right directions on the lower side of the tilt operating part 56. In this case, also, the rotation operating part 54a has a finger holder provided on the radially outer side relative to an end portion of the tilt operating part 56. This ensures that appropriate use of the rotation operating part 54a and the tilt operating part 56 according to the purpose can be easily realized, and operations of the rotation operating part 54a along the circumferential direction can be easily carried out. In addition, the tilt operating part 56 is so provided as to cover the upper side of a part of the rotation operating part 54a. As a result, the rotation operating part 54a and the tilt operating part 56 are collectively arranged in a compact form, which permits easy operation. The surfaces of the finger holder of the rotation operating part 54a and the tilting plate 76 are provided with a multiplicity of narrow grooves extending in the J directions, that function as finger holders.

Figure 13:
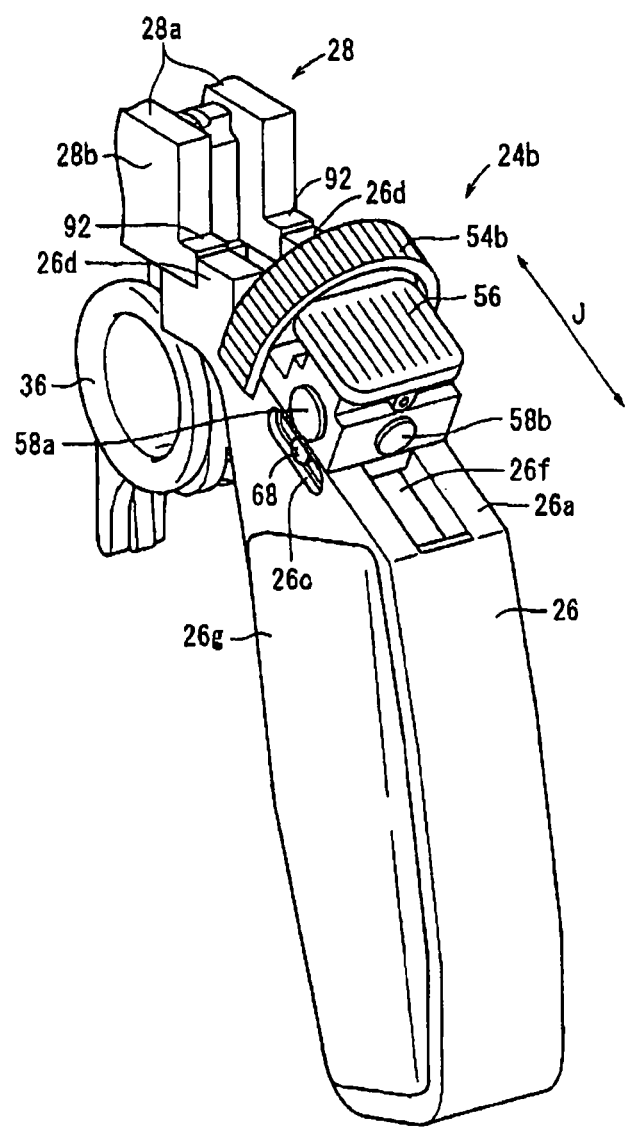
FIG. 13 is a perspective view of the grip handle, a composite input unit according to a second modification, and the vicinity thereof in the medical manipulator.

FIG. 13 shows a rotation operating part 54b of a composite input unit according to a second modification. As shown in the figure, the rotation operating part may have a semicircular shape in which the above-mentioned notches 72e are omitted. In this case, the outer peripheral surface of the rotation operating part 54b has an area suitable for receiving a finger thereon, and is provided with a multiplicity of narrow grooves extending in the J directions, that function as a finger holder.

Figure 14:
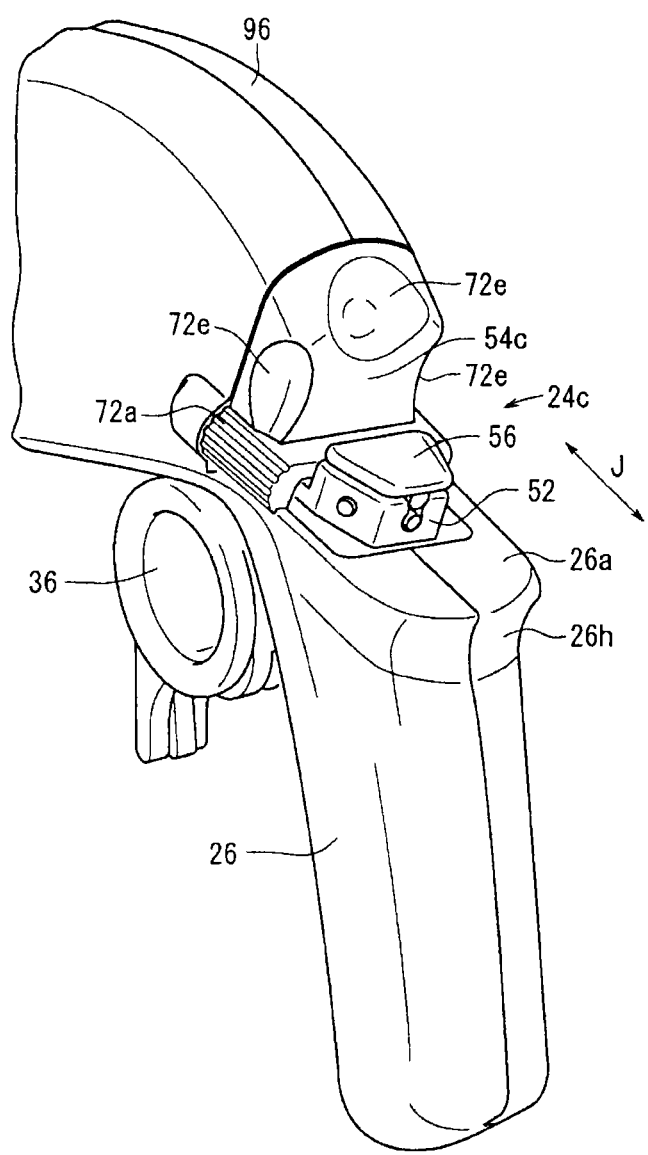
FIG. 14 is a perspective view of the grip handle, a composite input unit according to a third modification, and the vicinity thereof in the medical manipulator.

FIG. 14 shows a composite input unit 24c according to a third modification. As is shown, a rotation operating part 54c may be thickened in the J directions to a certain extent, and notches 72e may correspondingly be broadened to such an extent that a finger can be put thereon stably. In the case where a cover 96 that covers motors 100 and 102 is provided, it is preferable for the rotation operating part 54c to form a surface (flat surface or a curved surface) continuous with the cover 96 when it is in an initial position. This ensures that there is no useless protrusion or step or the like, so that preferable appearance is obtained, and easy operation can be realized.

An upper portion of the grip handle 26 may be so configured that the slant surface 26a has a somewhat broad roughly semi-elliptic shape, and a lower portion thereof is a smoothly curved surface. As a result, a roughly U-shaped convex curved surface portion 26h is formed, which is easy to grip with a thumb and an index finger and restrains the grip handle 26 from slipping off the fingers.

Figure 15:
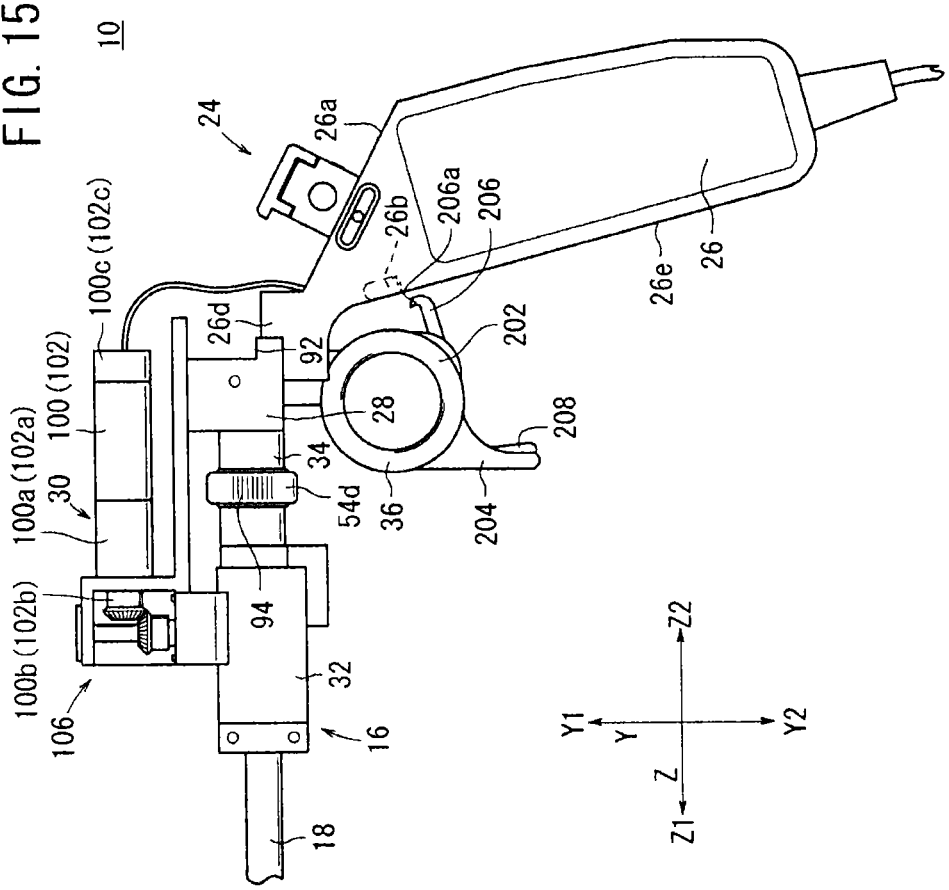
FIG. 15 is a side view of the grip handle, a rotation operating part according to a modification, and the vicinity thereof in the medical manipulator.

FIG. 15 shows a rotation operating part 54d as a modification of the rotation operating part 54. As shown in the figure, the rotation operating part 54 may be so configured that the tubular part 34 is located at its center, it is coaxial with the connector shaft 18, and it can be turned. The rotation operating part 54d is an input mechanism that actuates the rolling mechanism for the end effector 12. Therefore, where the rotation operating part 54d is coaxial with the connector shaft 18 and provided as close as possible to the end effector 12, it becomes easy to understand the operating method. Both surfaces, on both sides in the X directions, of the rotation operating part 54d are each provided with a finger holder 94.

Now, the actuator block 30 will be described below. The actuator block 30 is connected to the distal end of the bridge 28. The bridge 28 is composed of a left-right pair of wall bodies 28a, which are fixed to the joint pieces 26d of the grip handle 26 by screws 92. A trigger shaft 28b serving as a center of rotation of the trigger lever 36 is provided in the wall bodies 28a.

As shown in FIGS. 1 to 3, the actuator block 30 includes the two motors 100 and 102, an actuator bracket 104 that supports the motors 100 and 102, and a gear mechanism unit 106 by which rotation is transmitted from the motors 100 and 102 to the working unit 16 through a change in rotational direction.

The motors 100 and 102 each have a cylindrical shape with a diameter-to-length ratio of about 1:4, and respectively include reduction gears 100a and 102a provided on the Z1 direction side, output shafts 100b and 102b reduced in speed by the reduction gears 100a and 102a, and angle sensors 100c and 102c provided on the Z2 direction side. Each of the motors 100 and 102 is, for example, a DC motor. The reduction gears 100a and 102a are, for example, of a planetary gear system, with a reduction gear ratio in the range of from about 1:100 to about 1:300. As the angle sensors 100c and 102c, for example, rotary encoders may be used, and angle signals obtained upon angle detection are supplied to a controller. The motors 100 and 102 are slightly different in length, depending on differences in reduction gear ratio and the like.

The actuator bracket 104 has a first plate 108, a second plate (motor plate) 110, a third plate (bearing member) 112, and a fourth plate (reinforcement plate) 114, and is obtained by cutting or welding or the like.

The first plate 108 extends in the Z directions, has a length of about 1.3 times the whole lengths of the motors 100 and 102, has its end on the Z1 direction side connected to the pulley box 32 of the working unit 16, and is connected to the bridge 28 in the vicinity of its end on the Z2 direction side. The first plate 108 is provided in its central portion with a hole 108a for reduction in weight. In plan view (see FIG. 3), the width of the first plate 108 in the X directions, at its portion on the Z2 side relative to the second plate 110, is slightly greater than two times the diameter of the motors 100 and 102, and a gear mechanism base plate (bearing member) 108b on the Z1 side is further wider. Both ends of the gear mechanism base plate 108b are fixed to the pulley box 32 through a bracket 111 by a pair of screws 109.

The second plate 110 has a height of about 1.5 times the diameter of the motors 100 and 102, and protrudes in the Y1 direction from a position deviated from the Z1-side end of the first plate 108 by a distance of about 0.3 times the whole length of the first plate 108. The motors 100 and 102 are supported on the second plate 110 by a plurality of screws 115 (see FIG. 16) oriented to extend in the Z2 direction, and their output shafts 100b and 102b pass through holes 117 (see FIG. 16), to protrude to the Z1 direction side. The motor 100 and the motor 102 are arranged at symmetrical positions in the X directions, with little gap therebetween. With reference to the diameter R of the motors 100 and 102, the distance between the center axis of the connector shaft 18 and each of the center axes of the motors 100 and 102 in side view is about 2R, and there is a little gap between each of the lower surfaces of the motors 100 and 102 and the upper surface of the first plate 108. With respect to the Z directions, the Z2-side ends of the motors 100 and 102 are each located substantially the same position as the Z1-side end of the grip handle 26. Cables 100d and 102d (inclusive of connection lines for the angle sensors 100c and 102c) for the motors 100 and 102 extend respectively from Z2-side ends of the motors 100 and 102, and are led into the grip handle 26.

The third plate 112 protrudes in the Z1 direction from an end portion of the second plate 110. The first plate 108 and the third plate 112 are parallel to each other, and their Z1-side ends are located at the same position. The fourth plate 114 is so provided that it is connected to the first plate 108, the second plate 110 and the third plate 112 on three sides, and it forms a YZ plane at a central portion with respect to the X directions. The fourth plate 114 functions as a reinforcement plate, whereby the first plate 108, the second plate 110 and the third plate 112 are stabilized.

The gear mechanism unit 106 is provided in a space surrounded by the first plate 108, the second plate 110 and the third plate 112, as a structure which is symmetrical in the X directions with reference to the fourth plate 114.

Figure 16:
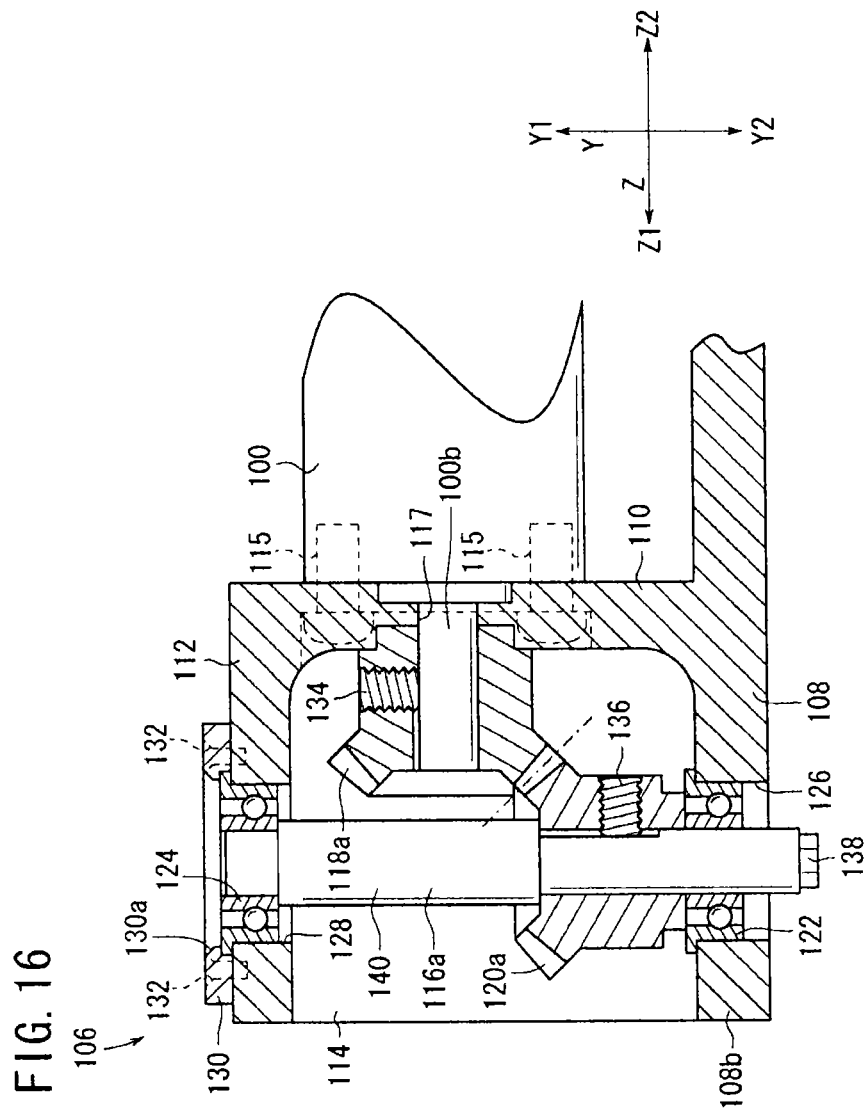
FIG. 16 is a sectional side view of a gear mechanism unit.

As shown in FIGS. 2 and 16, the gear mechanism unit 106 has two drive shafts (rotator) 116a and 116b, two drive bevel gears 118a and 118b, and two driven bevel gears 120a and 120b.

The gear mechanism base plate 108b and the second plate 110 are provided with shaft holes 126 and 128 in which to dispose bearings 122 and 124 that bear the drive shafts 116a and 116b, respectively. The bearings 122 and 124 are positioned by a structure in which parts of their outer rings make contact with end surfaces of the gear mechanism base plate 108b and the second plate 110, respectively. A lock plate 130 that locks the outer ring of the bearing 124 is secured to the upper surface of the second plate 110 by a plurality of screws 132. The lock plate 130 is provided with two holes 130a that exposes end portions of the drive shafts 116a and 116b.

The output shaft 100b extends in the Z directions into the vicinity of the drive shaft 116a by passing through a hole 117, and the drive bevel gear 118a is secured thereto by a set screw 134. The fourth plate 114 is provided in both left and right side surface thereof with arcuate recesses 114 in order to avoid the drive bevel gear 118a.

The drive shaft 116a extends in the Y directions in such a manner that its upper end is borne by the bearing 124 whereas its lower end penetrates the bearing 122 in the shaft hole 126, to protrude by a predetermined amount. The drive shaft 116a is provided at its lower end face with a t-shaped protuberant part 138.

The driven bevel gear 120a is secured to the drive shaft 116a by a set screw 136. The drive bevel gear 118a and the driven bevel gear 120a are meshed with each other so as to transmit the rotation of the output shaft 100b to the drive shaft 116a, with a 90° change in the rotational direction.

The drive shaft 116a is positioned by a structure in which the upper end of a middle large-diameter portion 140 thereof makes contact with the inner ring of the bearing 124 whereas the lower end makes contact with the inner ring of the bearing 122 through the driven bevel gear 120a.

In plan view (see FIG. 3), the drive shafts 116a and 116b are disposed on the extension lines of the axes of the motors 100 and 102, respectively.

According to the gear mechanism unit 106 including the drive bevel gears 118a and 118b, the driven bevel gears 120a and 120b, and the drive shafts 116a and 116b as above-mentioned, the motors 100 and 102 can be juxtaposed even if they are larger in diameter as compared with the connector shaft 18. Consequently, the degree of freedom as to motor layout is enhanced.

The motors 100 and 102 are located symmetrically in the Y directions, and the drive shafts 116a and 116b are located symmetrically in the Y directions, with reference to the connector shaft 18. This layout provides good balance.

In the gear mechanism unit 106, the gear mechanism base plate 108b and the second plate 110 act as bearing members that bear the drive shafts 116a and 116b through the driven bevel gears 120a and 120b therebetween. In addition, the third plate 112 acts as a motor plate that fixes the motors 110 and 102, and interconnects the gear mechanism base plate 108b and the second plate 110. This structure, though simple, provides high rigidity, and can stably hold the motors 100 and 102 and the drive shafts 116a and 116b. Besides, since the fourth plate 114 that interconnects the gear mechanism base plate 108b, the second plate 110 and the third plate 112 is provided between the drive shafts 116a and 116b, a further higher rigidity can be obtained.

Now, the pulley box 32 will be described below. The pulley box 32 has a first function of relaying the rotations of the drive shafts 116a and 116b to the connector shaft 18 while being in connection with the gear mechanism unit 106 in the operating unit 14. A second function of the pulley box 32 is to relay an operation on the trigger lever 36 to the connector shaft 18 while being in connection with the tubular part 34. A third function of the pulley box 32 is to maintain the inside of the connector shaft 18 in an air-tight state.

Figure 17:
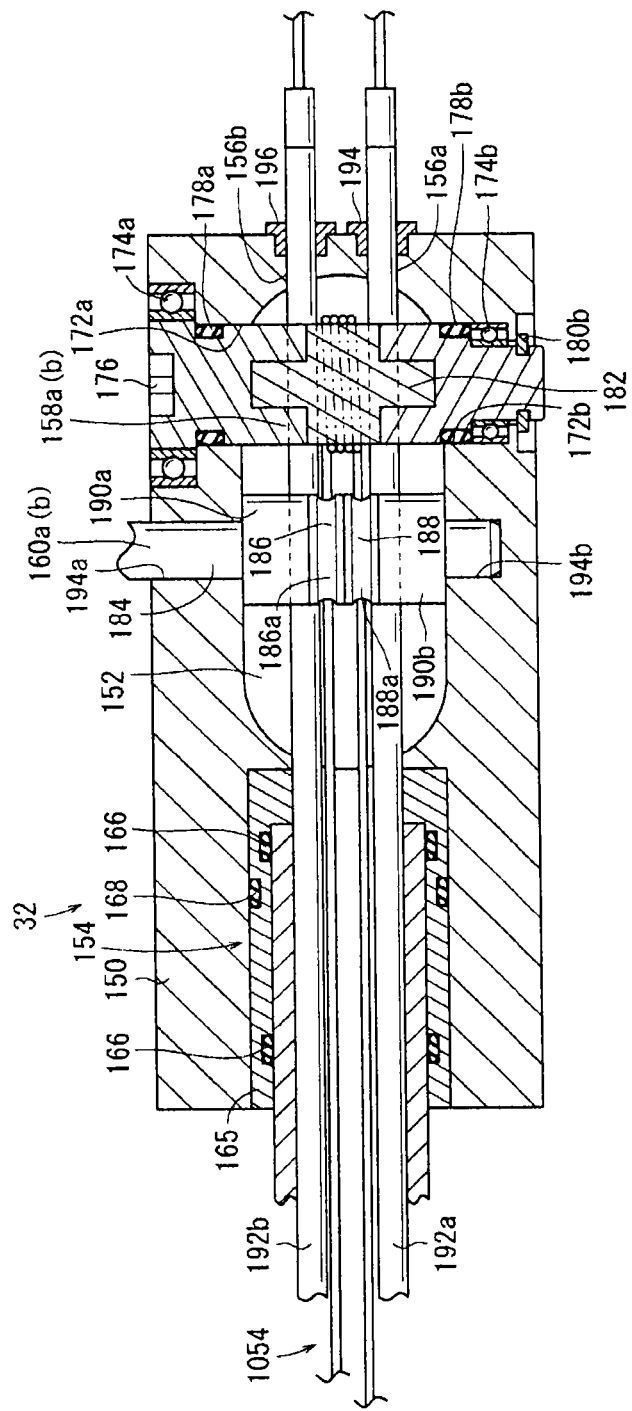
FIG. 17 is a sectional side view of a pulley box.
Figure 18:
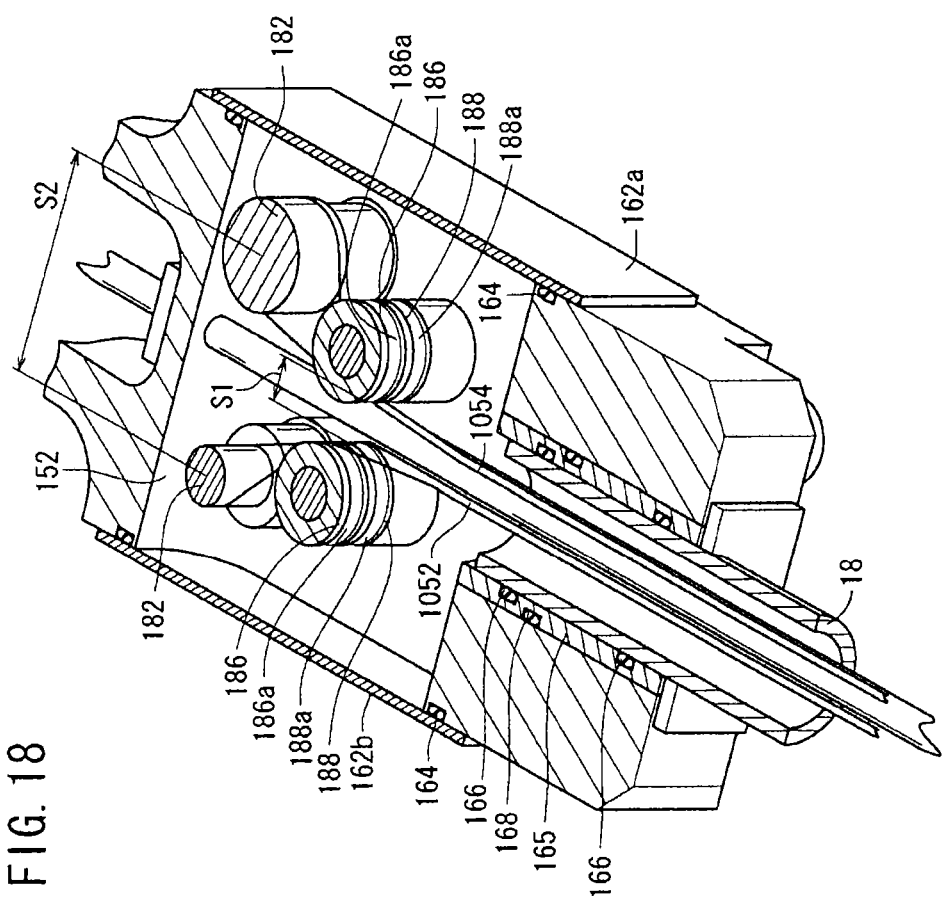
FIG. 18 is a sectional perspective view of the pulley box.

As shown in FIGS. 17 and 18, the pulley box 32 is configured by using a box main body 150 as a base. Besides, the pulley box 32 includes: a cavity 152, a shaft support part 154 and rod holes 156a and 156b which are provided in the box main body 150; pulleys (rotators) 158a and 158b; wire guide parts 160a and 160b; and side plates 162a and 162b that cover the cavity 152 at both side surfaces on the X1 and X2 sides.

The cavity 152 is a hole through which the side surfaces on the X1 and X2 sides communicate with each other. In side view (see FIG. 17), the cavity 152 is provided in an area ranging toward the Z2 direction side and away from a substantially middle portion of the pulley box 32. Both the Z1-side and Z2-side ends of the cavity 152 are semicircular in shape in side view. O-rings 164 that surround the cavity 152 are provided at both X1-side and X2-side surfaces of the pulley box 32. The O-rings 164 are compressed to an appropriate extent upon mounting the side plates 162a and 162b.

The shaft support part 154 is a hole communicating with a Z1-side end face while extending from the cavity 152, and supports the connector shaft 18 therein. A hollow cylindrical coupler 165 is provided at the Z2-side end of the connector shaft 18, and the shaft support part 154 supports the connector shaft 18 through the coupler 165 therebetween. Two O-rings 166 are provided between the coupler 165 and the connector shaft 18, and an O-ring 168 is provided between the coupler 165 and the shaft support part 154. The connector shaft 18 is fixed by a structure in which a fixture piece 170 (see FIG. 2) is fastened to a distal portion of the box main body 150 from an X1-side surface by two screws 172 (see FIG. 2).

In the cavity 152, bearings 174a and 174b are provided in two pairs of coaxial holes 172a (on the Y1 side) and 172b (on the Y2 side) aligned in the Y direction, and pulleys 158a and 158b are rotatably borne by the bearings 174a and 174b, respectively. The pulleys 158a and 158b are coaxial with the drive shafts 116a and 116b, and a t-shaped recessed part 176 at a Y1-side end face is engaged with the above-mentioned protuberant part 138. According to the protuberant part 138 and the recessed part 176, the drive shafts 116a and 116b and the pulleys 158a and 158b can be engaged only at mutually corresponding angles.

The gap between the pulley 158a and the pulley 158b is equal to the gap between the drive shaft 116a and the drive shaft 116b, and is larger than the diameter of the connector shaft 18.

The pulleys 158a and 158b are rotatably sealed air-tight in relation to the coaxial hole 172a by an O-ring 178a, and are sealed in relation to the coaxial hole 172b by an O-ring 178b. The pulleys 158a and 158b are each prevented from slipping off, by an E-ring 180 at a Y2-side end portion. A diameter adjusting member 182 is interposed at central portions of the pulleys 158a and 158b. By the diameter adjusting member 182, the wrapping diameters of wires 1052 and 1054 which will be described later can be adjusted (see FIG. 18).

A wire guide unit 160a includes a press-fit shaft 184, two layers of cylindrical idlers 186 and 188 rotatably borne adjacently to the press-fit shaft 184, and positioning tubes 190a and 190b that position the cylindrical idlers 186 and 188. The press-fit shaft 184 extends in the Y direction, passes through a through-hole 194a formed on the Y1 side relative to the box main body 150, is inserted in a bottomed hole 194b formed on the Y2 side, and is press fitted in these holes. The press-fit shaft 184 is equipped with the positioning tube 190a, the cylindrical idler 186, the cylindrical idler 188 and the positioning tube 190b in this order from the Y1 side toward the Y2 side, in the cavity 152. The cylindrical idlers 186 and 188 are pulleys that can be rotated independently.

The gap S1 between the two cylindrical idlers 186 (the same applies to the gap between the cylindrical idlers 188) is set to be smaller than the inside diameter of the connector shaft 18, specifically, to be not more than ½ times the inside diameter. The cylindrical idlers 186 and 188 are freely rotatable, and are provided in their circumferential surfaces with grooves 186a and 188a in which to dispose the wire 1054. The cylindrical idlers 186 and 188 may not necessarily be rotatable, if appropriate lubricity is secured thereon.

Where such wire guide units 160a and 160b are used, the connector shaft 18 can be sufficiently reduced in diameter independently of the diameter of the motors 100 and 102 or the inter-axial distance S2 between the pulley 158a and the pulley 158b; for example, the diameter of the connector shaft 18 is set at a value of about 5 to 10 mm, which is suitable for insertion into the trocar 20. In addition, the degree of freedom in laying out the motors 100 and 102 accompanied by the gear mechanism unit 106 is enhanced. While the forward line and the return line of the wire 1054 are moved in opposite directions, the two layers of cylindrical idlers 186 and 188 are so arranged as to correspond to these movements, so that the lines can perform frictionless motions.

Two rods 192a and 192b penetrate the cavity 152 in the Z direction, in the state of being juxtaposed in the Y direction. The rods 192a and 192b are stainless steel pipes or solid rods which are sufficiently strong and small in diameter. The rods 192a and 192b penetrate in the Z1 direction, and pass through the rod holes 156a and 156b in the Z2 direction.

The rods 192a and 192b are held in the rod holes 156a and 156b through seal members 194 and 196 therebetween. The seal members 194 and 196 make contact with the rods 192a and 192b in a gapless manner, to secure air-tight seal such that the rods 192a and 192b can advance and retract in the Z directions within the cavity 152 and the connector shaft 18.

The cavity 152 is sealed relative to the rods 192a and 192b by the seal members 194 and 196, relative to the pulleys 158a and 158b by the O-rings 178a and 178b, relative to the connector shaft 18 by the O-rings 166 and 168, and relative to the side plates 162a and 162b by the O-rings 164, and the press-fit shaft 184 is press fitted in the through-hole 194a. As a result, the cavity 152 is maintained in an air-tight state. Incidentally, an O-ring may be provided in the periphery of the press-fit shaft 184 to thereby enhance the sealing performance. The outer peripheral surface of the connector shaft 18 is supported air-tight by the trocar 20 (see FIG. 1), and, therefore, a gas supplied into the body cavity 22 would not leak.

Figure 19:
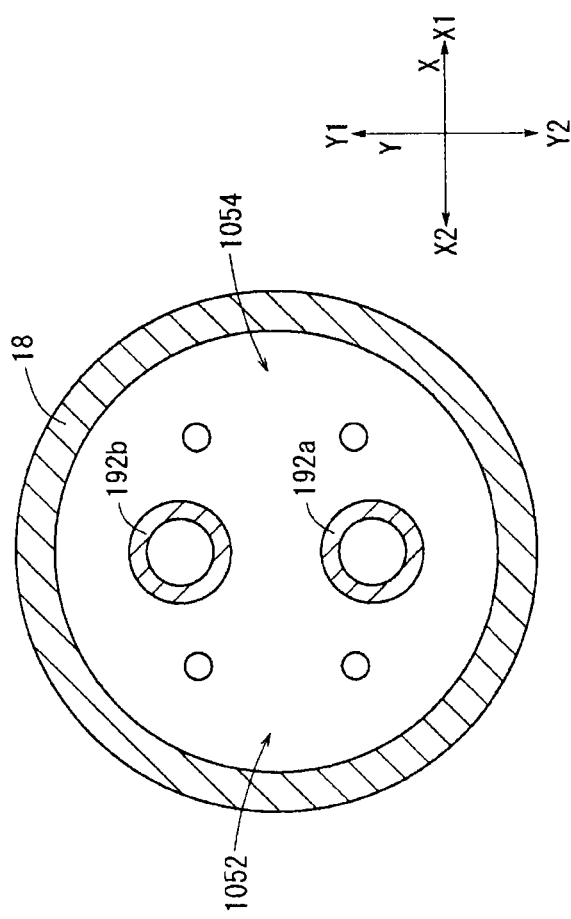
FIG. 19 is a sectional front view of a connector shaft.

As shown in FIG. 19, in the shaft support part 154, the rods 192a and 192b are juxtaposed in the Y direction, the respective forward and return lines of the wire 1052 and the wire 1054 are closely juxtaposed in the Y direction, and the wire 1052 and the wire 1054 are juxtaposed in the X direction. Thus, these components are arranged in good balance.

Now, configurations of the tubular part 34 and the trigger lever 36 will be described below.

Figure 20:
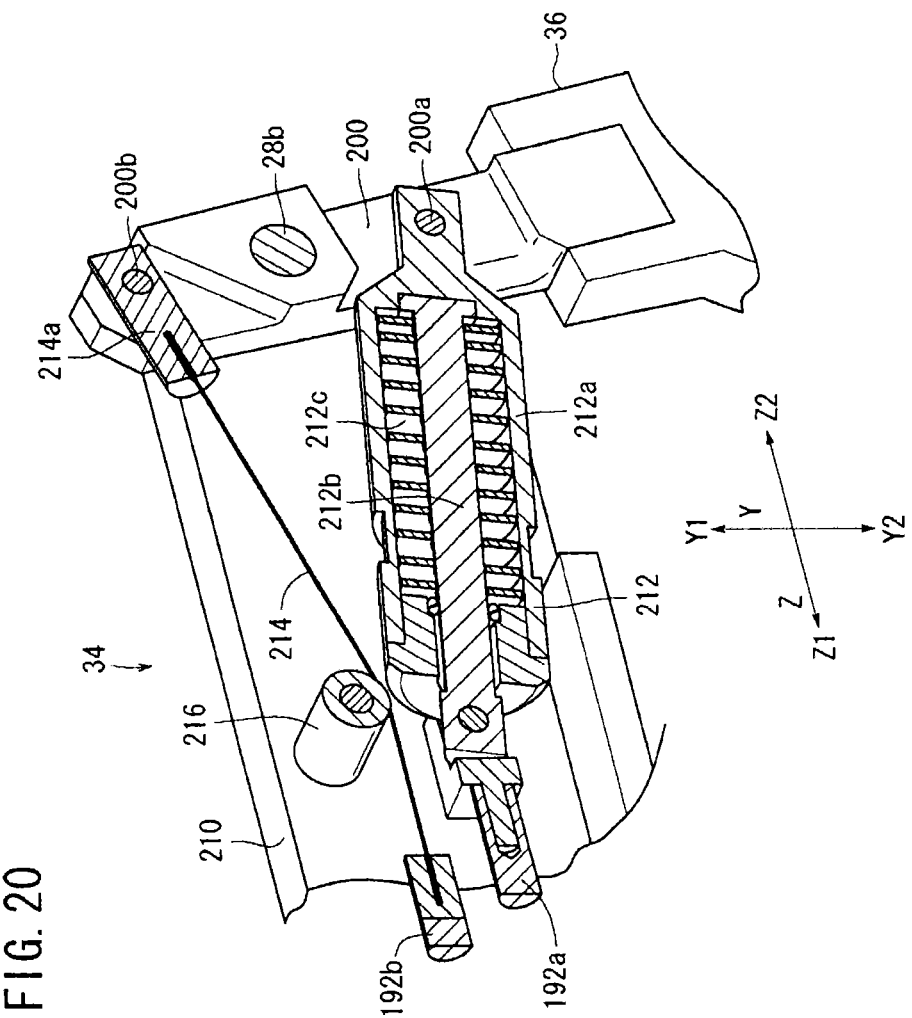
FIG. 20 is a partially sectional perspective view of a tubular part and a trigger lever.

As shown in FIGS. 1 and 20, the trigger lever 36 is turnably borne on a trigger shaft 28b in the bridge 28. The trigger lever 36 includes an arm part 200 turnably borne on the trigger shaft 28b, a finger ring part 202 provided on the Y2 side of the arm part 200, a finger holder protrusion 204 provided on the Y2 side, and a ratchet pawl 206 protruding toward the Z2 direction side. The index finger is mainly inserted into the finger ring part 202, and the finger holder protrusion 204 is suitable for receiving mainly the middle finger and the third finger thereon.

The ratchet pawl 206 is integral with a ratchet release 208, and a pawl 206a at the tip thereof is biased upward by an elastic body (not shown). When the trigger lever 36 is largely displaced in the Z2 direction, the pawl 206a of the ratchet pawl 206 is engaged with the stepped engaging part 26b inside the grip handle 26, whereby the position of the trigger lever 36 is held, and end effector elements 1300 (see FIG. 1) can be locked in a closed state. It is preferable that the stepped engaging part 26b is provided in the form of two steps, for example, so that the lock position of the trigger lever 36 or the grip force can be adjusted.

The ratchet release 208 is disposed inside the finger holder protrusion 204 in the state of being partly exposed. With the exposed portion depressed, the pawl 206a is lowered against resilience, whereby the trigger lever 36 can be unlocked.

The tubular part 34 has a tube 210 provided between the pulley box 32 and the trigger lever 36, and a load limiter 212 and a trigger wire 214 which are provided inside the tube 210. The tube 210, substantially coaxial with the connector shaft 18, is a base member of the tubular part 34, and functions also as a cover that covers the load limiter 212 and the trigger wire 214. The tube 210 may be provided, for example, with a slit in its Y2 side surface so as to permit its inside to be monitored. Incidentally, the outside diameter portion of the tube 210 may not necessarily be in a cylindrical shape, and may be in any shape insofar as it can support the trigger shaft 28b and the pulley 216.

The load limiter 212 has a hollow cylindrical shape, and has an outer cylinder 212a, an inner rod 212b, and a coil spring 212c. The inner rod 212b at the Z1-side end of the load limiter 212 is rotatably borne on an end portion of the rod 192a, and the outer cylinder 212a at the Z2-side end is rotatably borne on a shaft 200a of the arm part 200. The coil spring 212c is hard to an appropriate extent, and is interposed between the outer cylinder 212a and the inner rod 212b. Normally, the load limiter 212 as an essentially rigid body is interconnecting the rod 192a and the trigger lever 36. When an excessive load is exerted, that is, when a load in excess of a preload is exerted on the load limiter 212 due to pinching of something by the end effector elements 1300 or in other similar situations, the coil spring 212c is further compressed and the inner rod 212b is extended. This results in that, even if the trigger lever 36 is pulled excessively strongly, the acting force is limited by the load limiter 212, whereby the end effector elements 1300 (see FIG. 1) and the actuating mechanism therefor can be protected.

Incidentally, a maximum load for the load limiter 212 is desirably so set that even in the case where the trigger lever 36 is pulled most to the proximal side when the end effector elements 1300 are opened to the full, the acting force is not more than the allowable strength of the actuating mechanism such as wires.

The trigger wire 214 is connected at its Z1-side end to an end portion of the rod 192b, and is supported at its Z2-side end on a shaft 200b of the arm part 200 through a pin 214a. The trigger wire 214 is guided by the pulley 216, and its portion on the Z1 side relative to the pulley 216 is substantially coaxial with the rod 192b.

The shaft 200a is disposed on the Y1 side of the trigger shaft 28b, while the shaft 200b is disposed on the Y2 side of the trigger shaft 28b, and these shafts 200a and 200b are substantially equidistant from the trigger shaft 28b. Accordingly, with the trigger lever 36 operated, the shaft 200a and the shaft 200b are displaced in opposite directions but by substantially equal distances, and, attendant on this, the rod 192a and the rod 192b are displaced in opposite directions (in the Z1 and Z2 directions) but by substantially equal distances.

Figure 21:
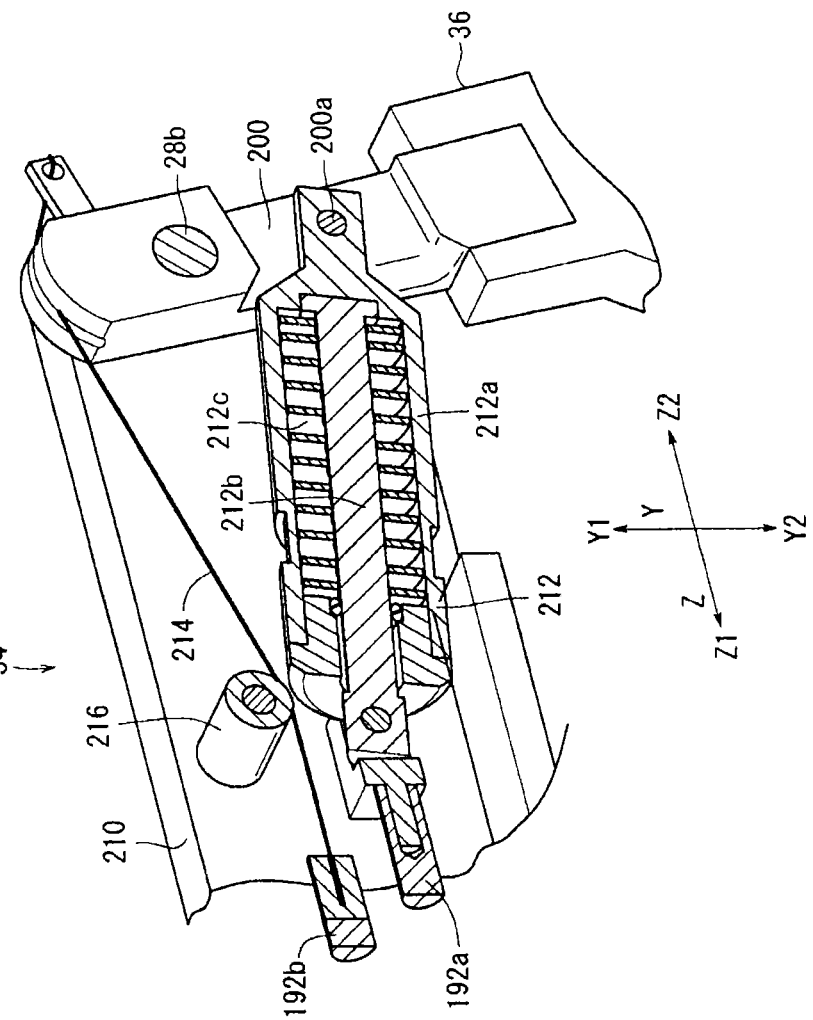
FIG. 21 is a partially sectional perspective view of a trigger lever of which an upper end is arcuate in shape.

As shown in FIG. 21, a Y1-side end portion of the arm part 200 may be in the shape of a circular arc, with the center of the circle located substantially at the trigger shaft 28b, that takes up the trigger wire 214. This ensures that the trigger wire 214 can be taken up in a uniform manner, irrespectively of the inclination angle of the arm part 200.

In the manipulator 10 configured as above-described, as shown in FIG. 10, the center of gravity G1 of the actuator block 30 is located at a comparatively short distance Lz1 in the Z direction from the center O of grip by hand (the grip center O is assumed to be at a central part of the grip handle 26, for convenience of description) and at a comparatively short distance Ly1 in the Y direction from the axis of the connector shaft 18. In addition, since the actuator has only two motors 100 and 102, the moment M1 (=G1×Lz1) exerted on the hand is sufficiently small, so that the load on the operator's hand is small.

In contrast, in the manipulator as described, for example, in U.S. 2008/0103491, as indicated by imaginary lines in FIG. 10, the actuator block 30a is considerably deviated toward the Z1 side relative to the grip hand 26, is protruding toward the Y2 side, and has three motors. The center of gravity G2 of the actuator block 30a is located at a comparatively long distance Lz2 in the Z direction from the grip center O and at a comparatively long distance Ly2 in the Y direction from the axis of the connector shaft 18. Therefore, the moment M2 (=G2×Lz2) exerted on the hand is comparatively large.

Besides, in an actual procedure, the manipulator 10 as a whole may be rotated about the connector shaft 18, in order to change the orientation of the end effector 12. For instance, where the manipulator 10 is rotated by 90° so that the X direction becomes the vertical direction, the moment M1 due to the actuator block 30 is M1=G1×Ly1, which is considerably small, so that the rotation is easy to carry out. On the other hand, in the manipulator described in U.S. 2008/0103491, the moment M2 is M2=G2×Ly2, which is considerably large.

Naturally, the manipulator 10 is advantageous over the manipulator described in U.S. 2008/0103491, in that the moment of inertia about the connector shaft 18 is smaller and the dynamic operability is higher.

Further, in the manipulator described in U.S. 2008/0103491, the actuator block 30a is considerably deviated toward the Z1 side relative to the grip handle 26, and the three motors are juxtaposed in the Z direction. Accordingly, a distal portion of the actuator block 30a is also deviated toward the Z1 direction, resulting in the difference of distance D between the distal portion and an end portion of the manipulator 10, as shown in FIG. 10. Accordingly, the connector shaft 18 in the manipulator 10 can be elongated by a length corresponding to the distance D. Consequently, interference of the manipulator 10 with the body surface or trocar 20 can be obviated, and operability is thereby enhanced.

Or, in the case where a conventional laparoscope and the medical manipulator 10 are used by gripping them by left and right hands respectively, the lengths of the left and right devices can be well balanced, resulting in enhanced operability.

In addition, since the motors 100 and 102 are not protruding sideways from the connector shaft 18, the manipulator 10 does not interfere with other device, so that operability is not lowered.

Owing to the above-mentioned features, the manipulator 10 can be used, with little sense of discomfort, by an operator who is accustomed only to conventional lightweight forceps.

Now, configuration of the end effector 12 will be described.

Figure 22:
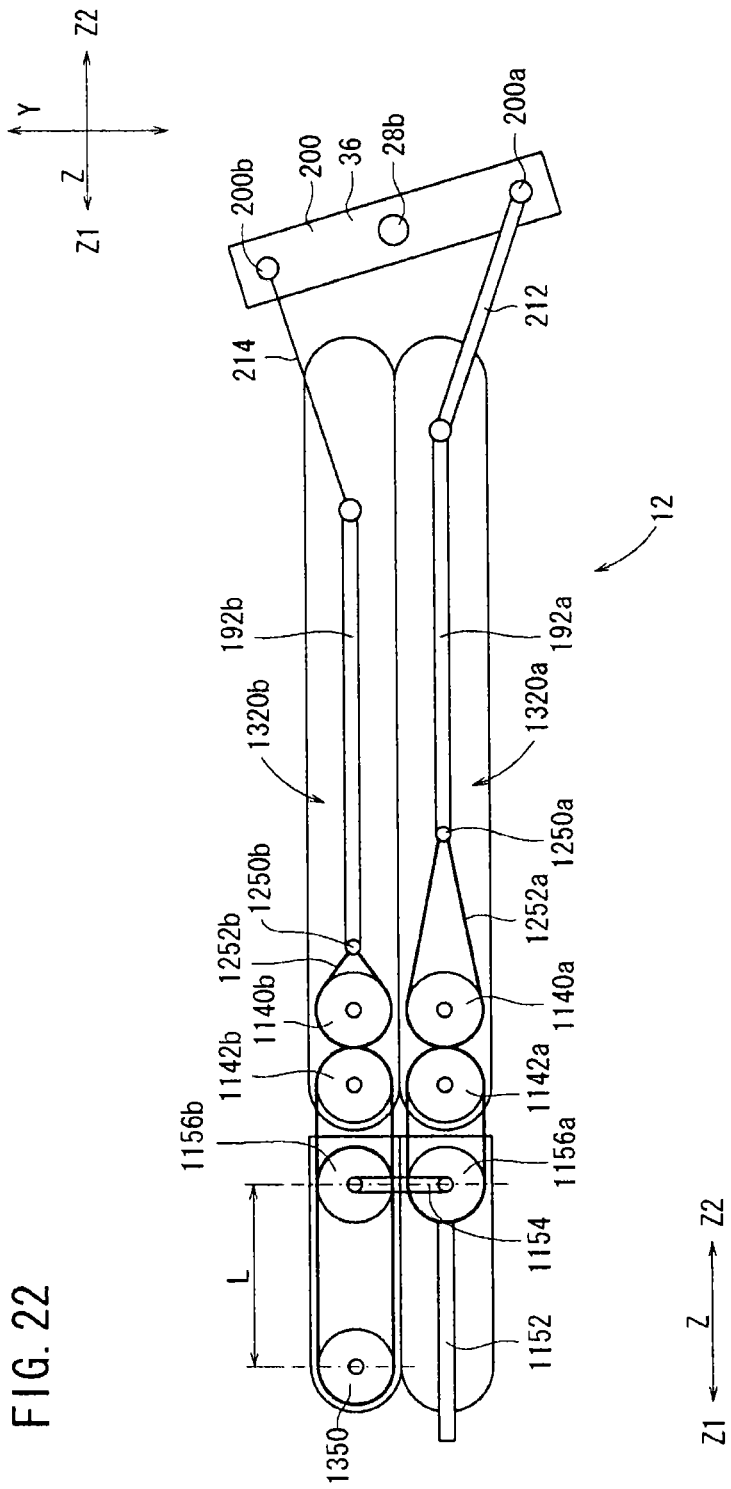
FIG. 22 is a schematic side view of an end effector when the trigger lever is pulled sufficiently.

As shown in FIG. 22, the end effector 12 is provided with a first end effector driving mechanism 1320a which includes a rod 192a, a passive wire 1252a, an idle pulley 1140a, a guide pulley 1142a, and a passive pulley 1156a, and a second end effector driving mechanism 1320b corresponding to the first end effector driving mechanism 1320a. The first end effector driving mechanism 1320a and the second end effector driving mechanism 1320b constitute a basic configuration for opening and closing the end effector elements 1300.

Components of the first end effector driving mechanism 1320a are denoted by reference numerals with a suffix a, while components of the second end effector driving mechanism 1320b are denoted by reference numerals with a suffix b, in order to distinguish the components. As to the components of the first end effector driving mechanism 1320a and the components of the second end effector driving mechanism 1320b which are the same in function, description may be made only of the components of the first end effector driving mechanism 1320a representatively, in order to avoid complication of description.

Figure 23:
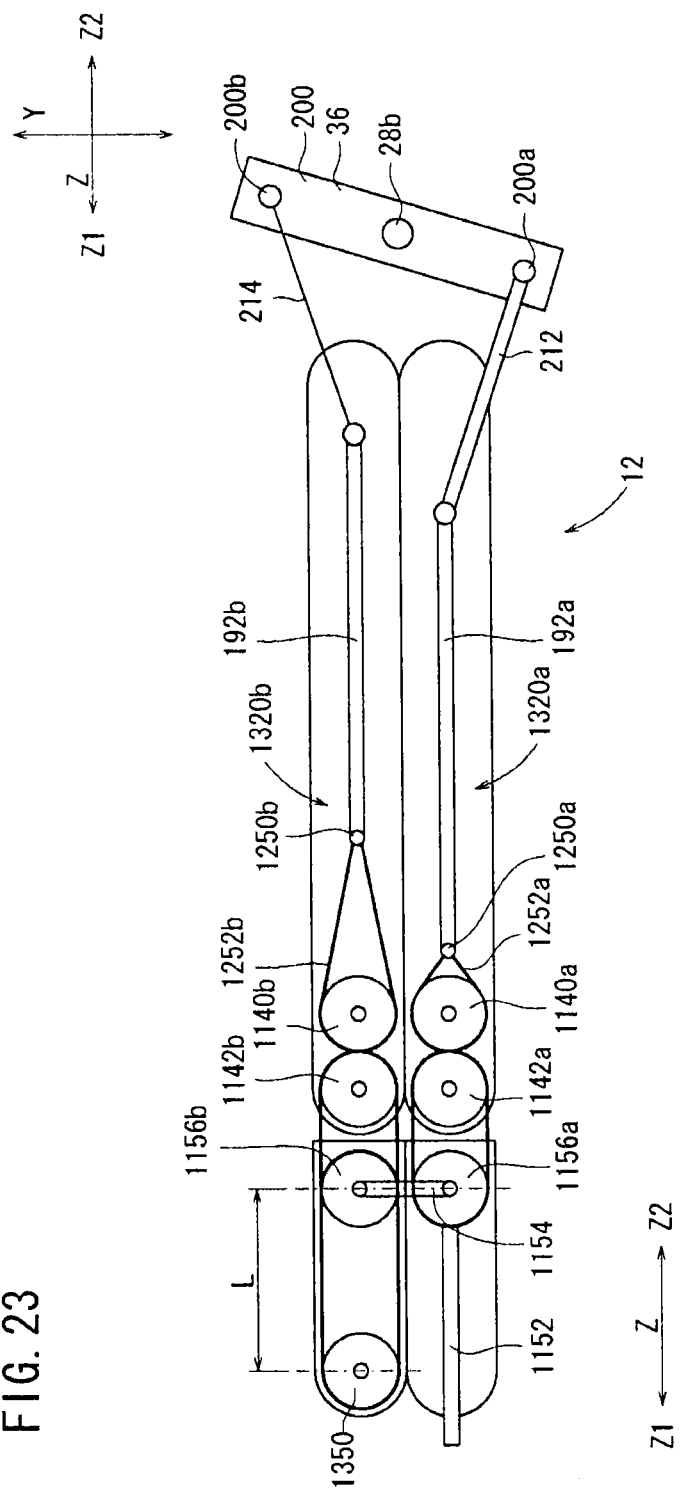
FIG. 23 is a schematic side view of the end effector when the trigger lever is pushed forwards.

In FIGS. 22 and 23, for ease of understanding, the first end effector driving mechanism 1320a and the second end effector driving mechanism 1320b are shown in a juxtaposed relation on the drawing. When these mechanisms are applied to the manipulator 10 in practice, however, the mechanisms are preferably juxtaposed in the axial direction of the pulleys (namely, in the Y direction), idle pulleys (cylindrical members; transmission members) 1140a and 1140b are preferably disposed coaxially, and guide pulleys (cylindrical members; transmission members) 1142a and 1142b are preferably disposed coaxially. Specifically, the idle pulleys 1140a and 1140b can be rotatably borne in common on a shaft 1110 (see FIG. 24), and the guide pulleys 1142a and 1142b can be rotatably borne in common on a shaft 1112. With the guide pulley 1142a and the guide pulley 1142b thus arranged coaxially, a yaw axis working mechanism is simplified in structure.

As shown in FIGS. 25, 26, 27 and 28, the end effector 12 includes a wire passive part 1100, a composite mechanism part 1102, and the end effector elements 1300. The end effector 12 has a total of three degrees of freedom consisting of a first degree of freedom for a part on the distal side of a first rotational axis Oy in the Y direction to be turned in yaw directions about the first rotational axis Oy, a second degree of freedom for the part to be turned in roll directions about a second rotational axis Or, and a third degree of freedom for the end effector elements 1300 at the distal end to be opened and closed about a third rotational axis Og.

The first rotational axis Oy as a mechanism of the first degree of freedom (pivot rotation mechanism) is preferably set to be turnable in non-parallel to an axis C extending from the proximal side toward the distal side of the connector shaft 18. The second rotational axis O4 as a mechanism of the second degree of freedom (turning mechanism) is preferably so set that it can be turned about an axis coinciding with the extending direction of the distal portion of the end effector 12 (namely, the end effector elements 1300), and its distal portion can be rolled.

The mechanism of the first degree of freedom (namely, the yaw directions) is a tilting mechanism (or a bending mechanism) having an operating range of, for example, ±90° or more. The mechanism of the second degree of freedom (namely, the roll directions) is a turning mechanism having an operating range of, for example, ±180° or more. The mechanism of the third degree of freedom (namely, the end effector elements 1300) is an opening and closing mechanism which can be opened to an angle of, for example, 40° or more.

The end effector elements 1300 are a part that performs actual work in a surgical operation. The first rotational axis Oy and the second rotational axis Or are attitude axes constituting an attitude change mechanism that changes the attitude of the end effector elements 1300 so as to facilitate the works. In general, the mechanism part pertaining to the third degree of freedom that opens and closes the end effector elements 1300 are called also a gripper (or a gripper axis), the mechanism part pertaining to the first degree of freedom that turns in the yaw directions is called also a yaw axis, and the mechanism part pertaining to the third degree of freedom that turns in the roll directions is called also a roll axis.

The wire passive part 1100 is provided between a pair of tongue parts 1058, as a part that converts forward and return motions of the wire 1052 and the wire 1054 into rotational motions and transmitting the rotational motions to the composite mechanism part 1102. The wire passive part 1100 has a shaft 1110 inserted in shaft holes 1060a, 1060a, and a shaft 1112 inserted in shaft holes 1060b, 1060b. The shaft 1110 and 1112 are fixed to the shaft holes 1060a and 1060b by, for example, press fit or welding. The shaft 1112 is disposed on the first rotational axis Oy.

A gear body 1126 and a gear body 1130 which are shaped symmetrically in the Y direction are provided at Y1-side and Y2-side ends of the shaft 1112. The gear body 1126 has a tube 1132, and a gear 1134 provided concentrically at an upper portion of the tube 1132. The gear body 1130 is substantially the same in shape as the gear body 1126, and is disposed on the Y2 side relative to the gear body 1126. The gear body 1130 has a tube 1136, and a gear 1138 provided concentrically at a lower portion of the tube 1136. The gear 1134 and the gear 1138 are meshed respectively with an upper end portion and a lower end portion of a face gear 1165 of a gear body 1146 which will be described later.

The tube 1136 is substantially the same as the tube 1132 in diameter and shape. The wires 1052 and 1054 are wrapped around the tube 1132 and the tube 1136, in the state of being partly fixed by predetermined fixing mechanism. The angle of wrapping of the wires 1052 and 1054 is, for example, 1.5 revolutions (540°).

With the wires 1052 and 1054 (see FIG. 25) operated for rotation, the gear body 1126 and the gear body 1130 can be rotated relative to the shaft 1112. When the gear body 1126 and the gear body 1130 are rotated in the same direction at the same speed, the gear body 1146 is oscillated with reference to the shaft 1112, whereby a yaw-direction motion is performed. When the gear body 1126 and the gear body 1130 are rotated in opposite directions at the same speed, the gear body 1146 is rotated with reference to the second rotational axis Or, whereby a rolling motion is performed. When the gear body 1126 and the gear body 1130 are rotated at different speeds, the gear body 1146 is put into a composite motion of a yaw-direction motion and a rolling motion. In short, the gear body 1126, the gear body 1130 and the gear body 1146 constitute a differential mechanism (corresponding, for example, to a configuration shown in FIG. 23 in U.S. 2008/0245175).

The mechanism of the end effector 12 is not limited to the differential mechanism. For example, a system may be adopted in which the wire 1052 drives the face gear 1165 through the gear 1134, whereas the wire 1054 directly drives a main shaft member 1144 to rotate (corresponding, for example, to a configuration shown in FIG. 7 in U.S. 2008/0245175).

The idle pulley (cylindrical member; transmission member) 1140a is rotatably borne on a substantially central portion of the shaft 1110, and the guide pulley (cylindrical member; transmission member) 1142a is rotatably borne on a substantially central portion of the shaft 1112. The idle pulley 1140a is provided in order to keep the wrapping angle constant (about 180° in total on both sides) of a passive wire (flexible member; transmission member) 1252a wrapped around the guide pulley 1142a. In place of using the idle pulley 1140, the passive wire 1252a may be wrapped around the guide pulley 1142a more than one wrap-around. The idle pulley 1140a and the guide pulley 1142a are preferably treated to make their surfaces smooth or formed from a low-friction material, that prevents them from being worn due to slipping or friction of the passive wire 1252a (see FIG. 30) thereon. The guide pulley 1142a is provided on the yaw axis Oy in an attitude changing mechanism.

On the shaft 1112, the main shaft member 1144 is rotatably borne between the gear body 1126 and the guide pulley 1142a and between the guide pulley 1142a and the gear body 1130. The main shaft member 1144 has a tubular part protruding toward the composite mechanism part 1102. The main shaft member 1144 is provided with a rectangular hole 1144a in its axial center portion. At a Z2-side end portion of the main shaft member 1144, two auxiliary plates 1144b are provided which hold both Y1-side and Y2-side surfaces of the guide pulley 1142a and which each have a hole permitting the shaft 1112 to pass therethrough. The auxiliary plates 1144b are mountain-shaped to be broadened along the Z1 direction, and prevent penetration of foreign matter such as thread.

The composite mechanism part 1102 includes an opening and closing mechanism for the end effector elements 1300, and an attitude changing mechanism that changes the attitude of the end effector elements 1300.

The composite mechanism part 1102 includes the gear body 1146 rotatably fitted over the peripheral surface of the tubular part of the main shaft member 1144, a nut body 1148 provided at the tip of the main shaft member 1144, a transmission member 1152 which is quadrilateral in shape and a Z2-side end portion of which is inserted in the hole 1144a, a passive pulley (cylindrical member; transmission member) 1156a rotatably borne on the Z2-side end portion of the transmission member 1152, a passive plate (transmission member) 1158, and a hollow cylindrical cover 1160.

That portion of the main shaft member 1144 which makes contact with the gear body 1146 is provided with a resin-made thrust bearing member 1144c. That portion of the nut body 1148 which makes contact with the gear body 1146 is provided with a resin-made thrust bearing member 1148a. The thrust bearing members 1144c and 1148a are low-friction members, which reduce friction and torque at the contact portions and prevent a load from being exerted directly on the face gear 1165. While the thrust bearing members 1144c and 1148a are so-called slide bearings, rolling bearings may be provided alternatively. This ensures that even in the cases where the end effector elements 1300 are firmly closed or opened, namely, where the gear body 1146 collides on the main shaft member 1144 strongly, the roll-axis motions can be performed smoothly.

The gear body 1146 has a stepped tubular shape, and includes a large-diameter part 1162 on the Z2 side, a small-diameter part 1164 on the Z1 side, and the face gear 1165 provided at the Z2-side end face of the large-diameter part 1162. The face gear 1165 is meshed with the gear 1134 and the gear 1138. The gear body 1146 prevents the nut body 1148 from slipping off the main shaft member 1144. The large-diameter part 1162 is provided with a screw at the outer periphery thereof.

The passive plate 1158 includes a recess 1166 on the Z2 side, an engaging part 1168 provided at a bottom surface of the recess 1166, ribs 1170 which are provided on both surfaces extending in the Y direction and which extend in the axial direction, and link holes 1172. The engaging part 1168 is so shaped as to be engaged with a mushroom-shaped protrusion 1174 provided at the distal end of the transmission member 1152. This engagement permits the passive plate 1158 and the transmission member 1152 to be relatively rotated about the roll axis. The width of the passive plate 1158 is approximately equal to the inside diameter of the cover 1160.

The cover 1160 is so sized as to cover substantially the whole of the composite mechanism part 1102, whereby penetration of foreign matter (living tissue, drug, thread, etc.) into the composite mechanism part 1102 or the end effector elements 1300 are prevented. The cover 1160 is provided in its inside surface with two axially extending grooves 1175 which face each other and in which the two ribs 1170 of the passive plate 1158 are fitted. With the ribs 1170 fitted in the grooves 1175, the passive plate 1158 is guided in the axial direction. Since the engaging part 1168 of the passive plate 1158 is engaged with the protrusion 1174, the passive pulley 1156a can be advanced and retracted in the axial direction within the hole 1144a together with the passive plate 1158 and the transmission member 1152, and rolling with reference to the transmission member 1152 is possible. The cover 1160 is fixed to the large-diameter part 1162 of the gear body 1146 by, for example, screwing, press fit, etc.

The cover 1160 is coupled (by screwing, press fit, welding or the like) to the gear body 1146 on the proximal side, so that the cover 1160 and the end effector elements 1300 are put into a roll axis motion, attendant on rotation of the gear body 1146.

Lever parts 1310 and the passive plate 1158 are interlinked by gripper links 1220. Specifically, a pin 1222 is inserted in a hole 1220a at one end of the each gripper link 1220 and in a hole 1218, and a pin 1224 is inserted in a hole 1220b at the other end of each gripper link 1220 and in the link hole 1172 in the passive plate 1158, whereby the lever parts 1310 and the passive plate 1158 are interlinked.

Figure 29:
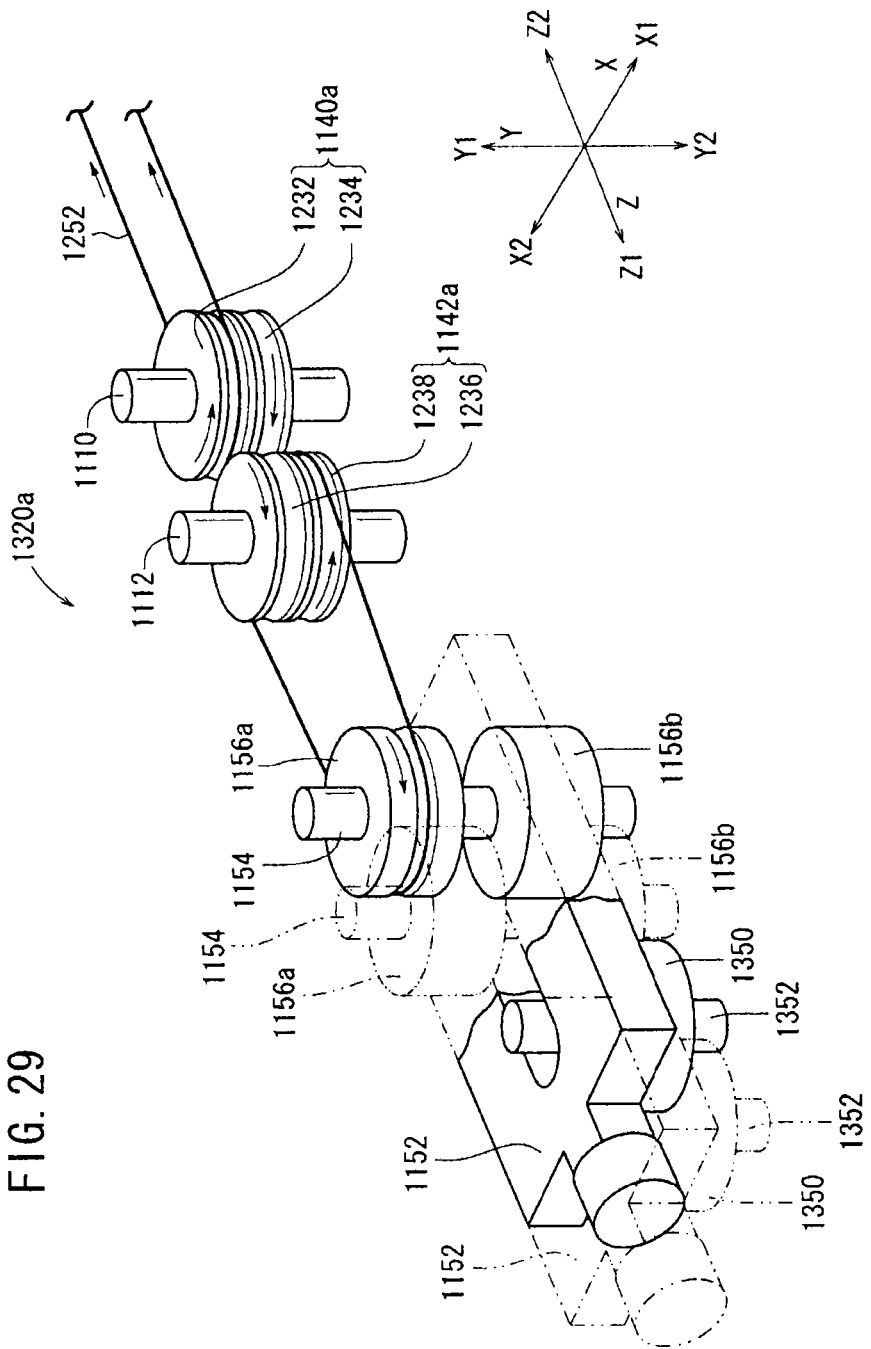
FIG. 29 is a schematic structural view of a part of an end effector driving mechanism.

As shown in FIG. 29, the idle pulley 1140a has a structure in which a first-layer idle pulley (first-layer idle cylindrical body) 1232 and a second-layer pulley (second-layer idle cylindrical body) 1234 on the same axis are juxtaposed. Similarly, the guide pulley 1142a has a structure in which a first-layer guide pulley (first-layer guide cylindrical body) 1236 and a second-layer guide pulley (second-layer guide cylindrical body) 1233 on the same axis are juxtaposed.

Figure 30:
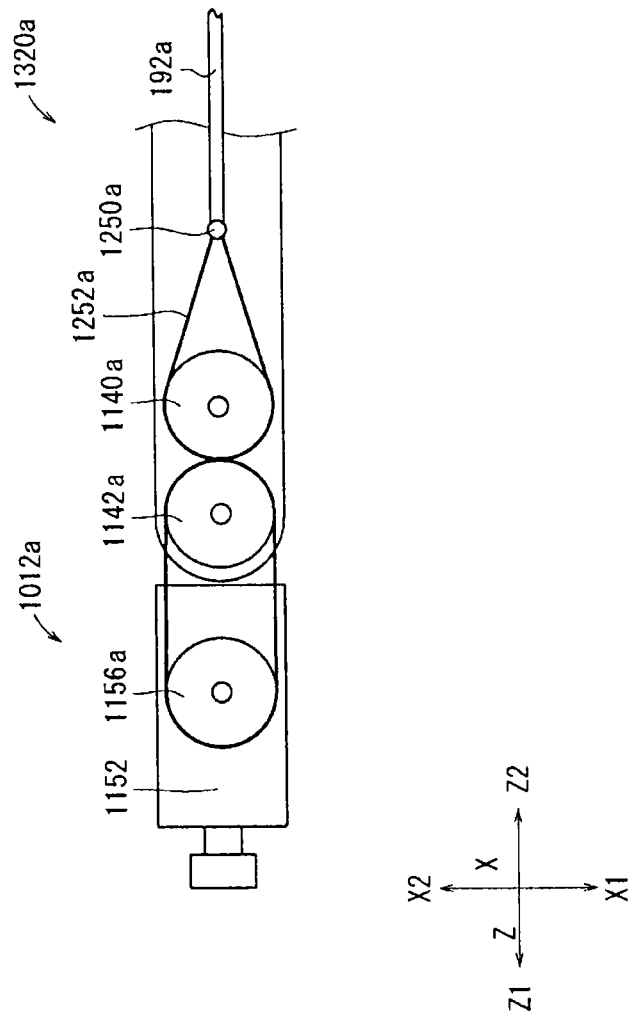
FIG. 30 is a schematic side view of the end effector driving mechanism when the trigger lever is not operated.

As shown in FIG. 30, a Z1-side end portion of the rod 192a is connected to both end portions of the passive wire (flexible member) 1252a by a wire engaging part 1250a.

Figure 31:
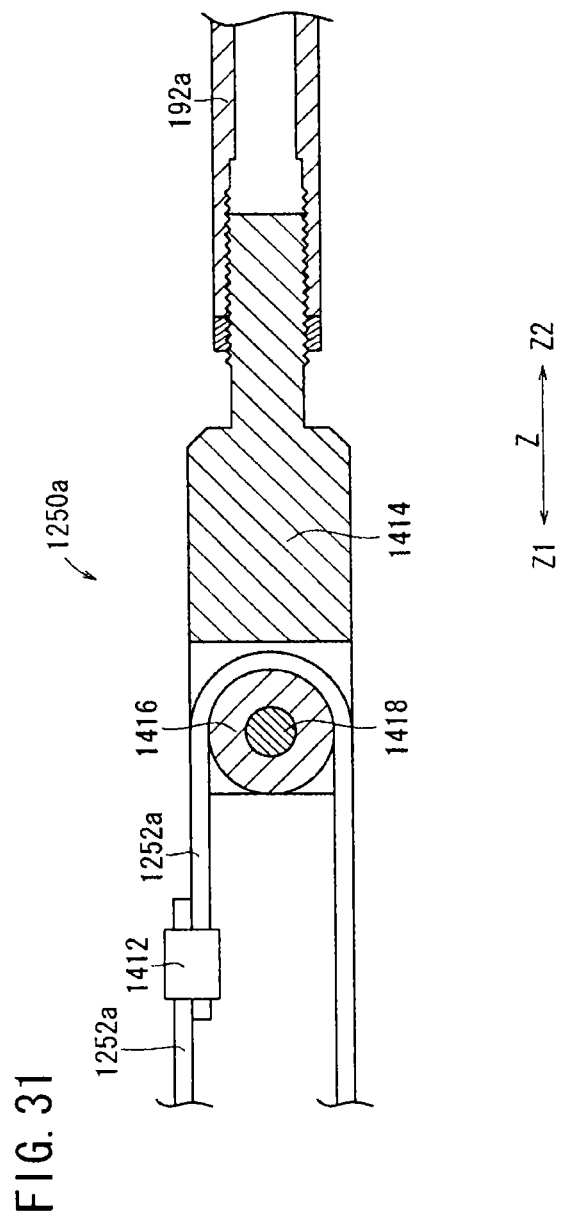
FIG. 31 is a schematic sectional plan view of a joint at an end portion of a passive wire.
Figure 32:
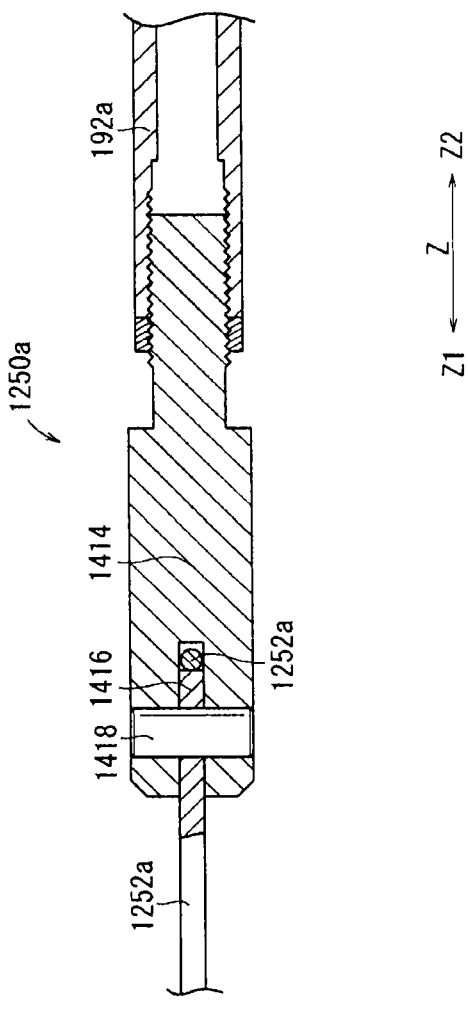
FIG. 32 is a schematic sectional side view of the joint at the end portion of the passive wire.

As shown in FIGS. 31 and 32, the wire engaging part 1250a is so configured that a roller 1416 is provided at a distal portion 1414 of the rod 192a, and the passive wire 1252a is wrapped around the roller 1416. The roller 1416 is rotatably borne on a pin 1418, and is rotatable. This ensures that the passive wire 1252a is advanced and retracted in an appropriate manner while being wrapped around the roller 1416. In addition, when the rod 192a is pulled in the Z2 direction, the passive wire 1252a can be pulled with good balance in the X direction, particularly, even in the condition where the yaw axis is not bent. The distal portion 1414 is screwed to the rod 192a. In this fourth modification, the tensions on a pair of Y-direction portions of the passive wire 1252a are uniform, so that a long useful life can be attained, and the pair of Y-direction portions on both the upper and lower side can be enhanced in parallelism.

Returning to FIGS. 29 and 30, the passive wire 1252a is a looped flexible member which is partly connected to the wire engaging part 1250a, and may not necessarily be a wire; for example, a rope, a resin string, a piano wire, a chain and the like can also be used. Here, the term "looped" is used in its broadest, and the flexible member may not necessarily be applied to the whole length of the looped member. It suffices that at least the portion which is wrapped around each pulley is a flexible member, and, naturally, a rectilinear portion may be connected by a rigid body.

The passive wire 1252a extends from the rod 192a as the driving member to pass in the X1 side (a first side) of the idle pulley 1140 toward the X2 side (a second side), passes along the X2-side surface of the guide pulley 1142a, and reaches the X2 side of the passive pulley 1156a. Further, the passive wire 1252a is wrapped by half a circumference around the Z1-side surface of the passive pulley 1156a to reach the X1-side surface of the passive pulley 1156a, passes along the X1-side surface of the guide pulley 1142a toward the X2 side, and passes along the X2 side of the idle pulley 1140a, to reach the wire engaging part 1250a.

Thus, the passive wire 1252a constitutes a round route with the wire engaging part 1250a as a start point and as an end point. Specifically, the passive wire 1252a passes on both sides of the idle pulley 1140a, is wrapped around the passive pulley 1156a, and intersects itself between the idle pulley 1140a and the guide pulley 1142a, thereby forming a substantially 8-shaped path. As a result, the wire engaging part 1250a and the passive wire 1252a are mechanically connected to the trigger lever 36 through the rod 192a.

The idle pulley 1140a, the guide pulley 1142a and the passive pulley 1156a are substantially equal in diameter, and formed to have an appropriately large diameter, within an allowable layout range, so that the passive wire 1252a is not bent considerably. The wire engaging part 1250a is provided at an appropriate distance from the idle pulley 1140a so that the passive wire 1252a is not bent excessively. Both end portions of the passive wire 1252a are forming an acute angle, with the wire engaging part 1250a as a vertex. The space between the idle pulley 1140a and the guide pulley 1142a is narrow; for example, a gap approximately equal to the width of the passive wire 1252a is formed between these pulleys.

The idle pulley 1140a, the guide pulley 1142a and the passive pulley 1156a may be equipped with small flanges at their upper and lower surfaces, or their side surfaces may be recessed in shape, that prevents the passive wire 1252a from slipping off these pulleys.

As is clear from FIG. 30, in the first end effector driving mechanism 1320a, the passive wire 1252a, the idle pulley 1140a, the guide pulley 1142a and the passive pulley 1156a are arranged along a center line in this order from the proximal side toward the distal side. The end effector elements 1300 are connected to the passive pulley 1156a through the transmission member 1152 and the like.

In the first end effector driving mechanism 1320a configured as above-described, when the rod 192a (see FIG. 30) is pulled in the Z2 direction, the first-layer idle pulley 1232 and the second-layer guide pulley 1238 are rotated counterclockwise in plan view, whereas the second-layer idle pulley 1234 and the first-layer guide pulley 1236 are rotated clockwise. Thus, the idle pulley 1140a and the guide pulley 1142a are coaxially arranged so that two layers of pulleys are juxtaposed; therefore, they can be rotated in opposite directions following the movement of the passive wire 1252a in contact with them. Consequently, smooth motions can be achieved.

The end effector elements 1300 are of a so-called both side opening type in which a pair of grippers 1302 are put into motion. The end effector elements 1300 include a gripper base 1304 formed integral with the cover 1160, a pair of end effector members 1308 operable with reference to a pin 1196 provided at the gripper base 1304, and the pair of gripper links 1220.

Each of the end effector members 1308 is L-shaped, and has the gripper 1302 extending in the Z1 direction, and the lever part 1310 extending while being curved at about 35° relative to the gripper 1302. The L-shaped bent portion is provided with a hole 1216, and the lever part 1310 is provided with a hole 1218 in the vicinity of an end portion thereof. With the pin 1196 inserted in the holes 1216, the pair of end effector members 1308 can be oscillated about the third rotational axis Og.

Each of the end effector members 1308 is linked to the pin 1224 at the passive plate 1158 by one gripper link 1220 on a lateral side. In the passive plate 1158 of the end effector elements 1300, the two link holes 1172 are provided at positions symmetrical in the Y direction in FIG. 26, and the pair of gripper links 1220 are disposed to intersect in side view.

As shown in FIGS. 25, 26, 27 and 28, the second end effector driving mechanism 1320*b* basically has a configuration obtained by adding a turnaround pulley 1350 (cylindrical member; transmission member) to the first end effector driving mechanism 1320*a* (see FIG. 30). The passive pulley 1156*a* and a passive pulley 1156*b* are coaxial with each other.

The main shaft member 1144 is provided with a shaft hole 1354 which is formed in a radial direction and in which a pin 1352 is inserted and fixed. The shaft hole 1354 penetrates the tubular portion of the main shaft member 1144 by way of the hole 1144*a*.

The transmission member 1152 is provided with a slot 1356 extending in the axial direction in such a width as to permit the pin 1352 to be inserted therethrough. While the transmission member 1152 is located with a slight offset in the Y1 direction from the axis of the working unit 1016, only the protrusion 1174 at the distal end is desirably located on the axis (see FIG. 30). Naturally, the transmission member 1152 may be disposed at the center.

A pin 1154 passes through the transmission member 1152 to protrude in the Y2 direction, and rotatably bear the passive pulley 1156*b*. The passive pulley 1156*b* has such a width as to permit the passive wire 1252*b* to be wrapped around the passive pulley 1156*b* twice. The hole 1144*a* has such a height that the passive pulleys 1156*a* and 1156*b* and the transmission member 1152 can be inserted therein. The passive pulleys 1156*a* and 1156*b* are rotatably borne coaxially inside the hole 1144*a* by the pin 1154, and can be rotated independently.

The pin 1352 extends from the Y1 side toward the Y2 side within the hole 1144*a*, and is inserted in the slot 1356 and a center hole in the turnaround pulley 1350, whereby the transmission member 1152 and the passive pulleys 1156*a* and 1156*b* can be advanced and retracted in the axial direction. The turnaround pulley 1350 is rotatably borne on the pin 1352, is therefore rotatable, but is fixed on a positional basis. The turnaround pulley 1350 has such a width that the passive wire 1252*b* can be wrapped around the turnaround pulley 1350 twice. In addition, with the turnaround pulley 1350 formed in a two-layer structure, the two layers can be rotated in opposite directions at the time of opening and closing motions, and friction between the passive wire 1252*b* and the pulley can be reduced.

Figure 33:
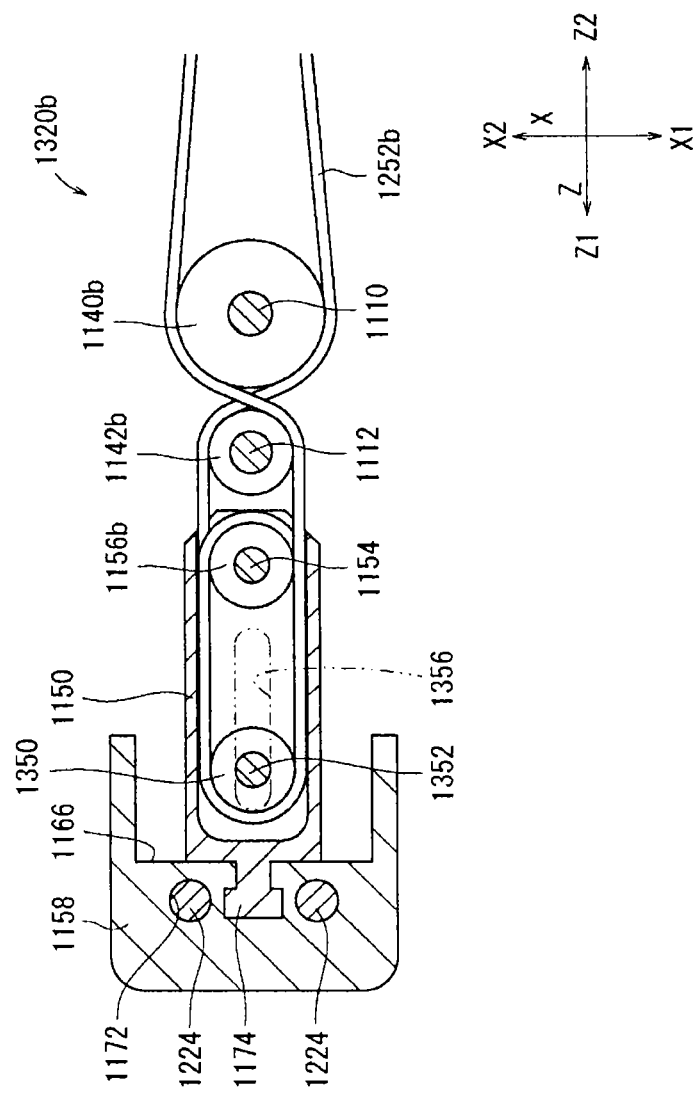
FIG. 33 is a partially sectional plan view of a second end effector driving mechanism when the trigger lever is pushed forwards.
Figure 34:
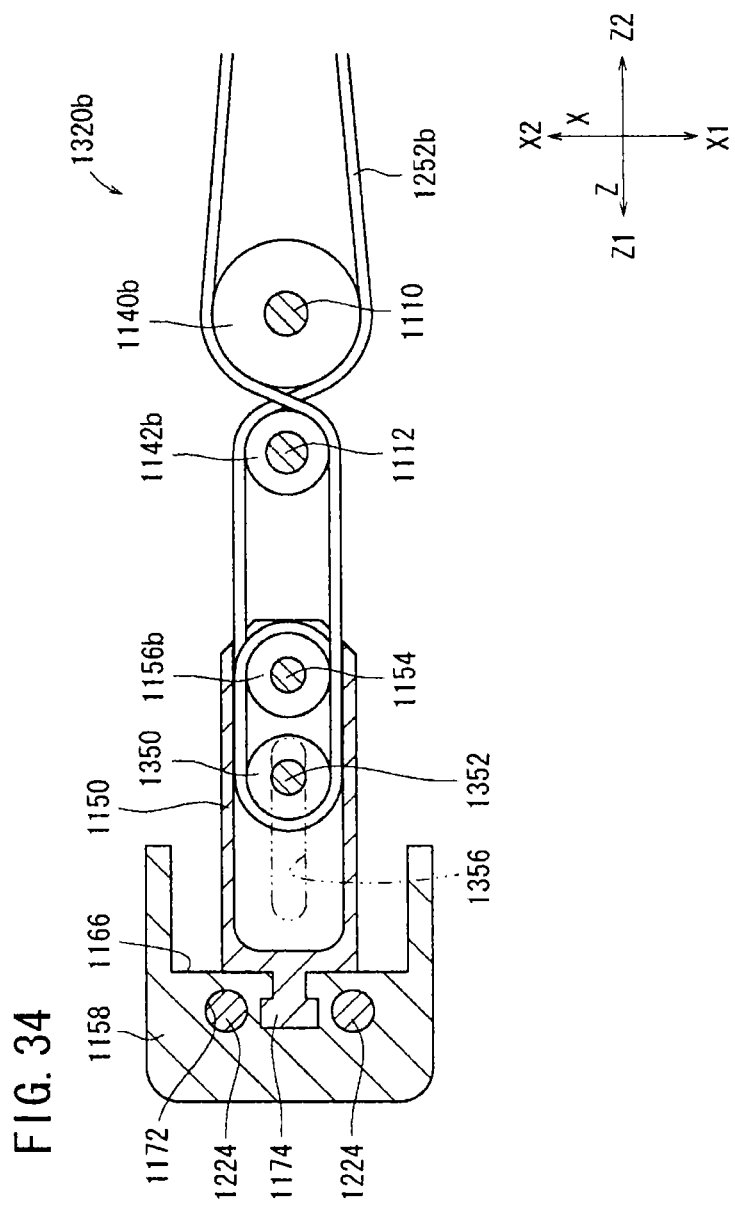
FIG. 34 is a partially sectional plan view of the second end effector driving mechanism when the trigger lever is pulled sufficiently.
Figure 35:
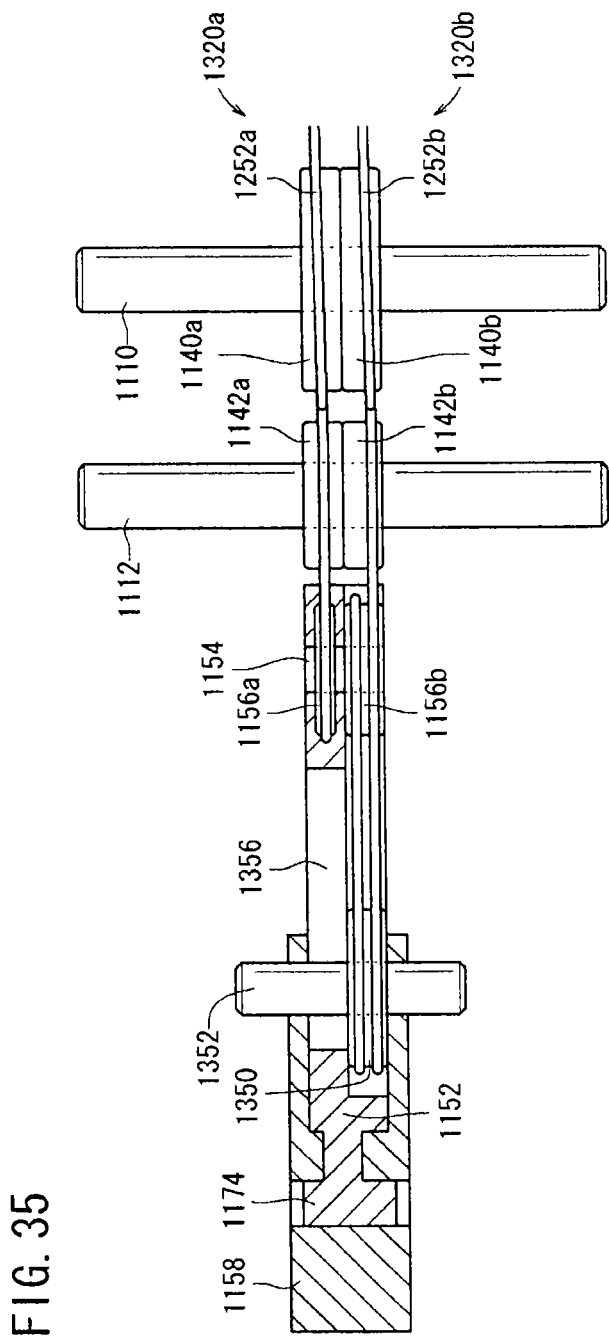
FIG. 35 is a partially sectional side view of the second end effector driving mechanism when the trigger lever is pushed forwards.

As shown in FIGS. 33, 34 and 35, in the second end effector driving mechanism 1320*b*, the turnaround pulley 1350 is provided on the distal side relative to the passive pulley 1156*b*, and the passive wire 1252*b* is wrapped around both the passive pulley 1156*b* and the turnaround pulley 1350. Specifically, the passive wire 1252*b* extends from a wire engaging part 1250*b* of the rod 192*b* of the driving member, passes on the X1 side of an idle pulley 1140*b* toward the X2 side, and passes on the X2 side of a guide pulley 1142*b*, to reach an X2-side surface of the passive pulley 1156*b*. Then, the passive wire 1252*b* extends as it is in the Z1 direction, reaches an X2-side surface of the turnaround pulley 1350, is wrapped half turn around a Z1-side surface of the turnaround pulley 1350, and turns around toward the Z2 side.

The passive wire 1252*b* is wrapped half turn around a Z2-side surface of the passive pulley 1156*b*, passes on the X2 side to again reach the turnaround pulley 1350, is again wrapped half turn around the Z1-side surface of the turnaround pulley 1350, and turns around toward the Z2 side. Thereafter, the passive wire 1252*b* extends from the X1 side of the guide pulley 1142*b* to reach the X2 side of the idle pulley 1140*b*, and is connected to the wire engaging part 1250*b* of the rod 192*b*. Consequently, the wire engaging part 1250*a* and the passive wire 1252*b* are mechanically connected to the trigger lever 36 through the rod 192*b*.

Figure 24:
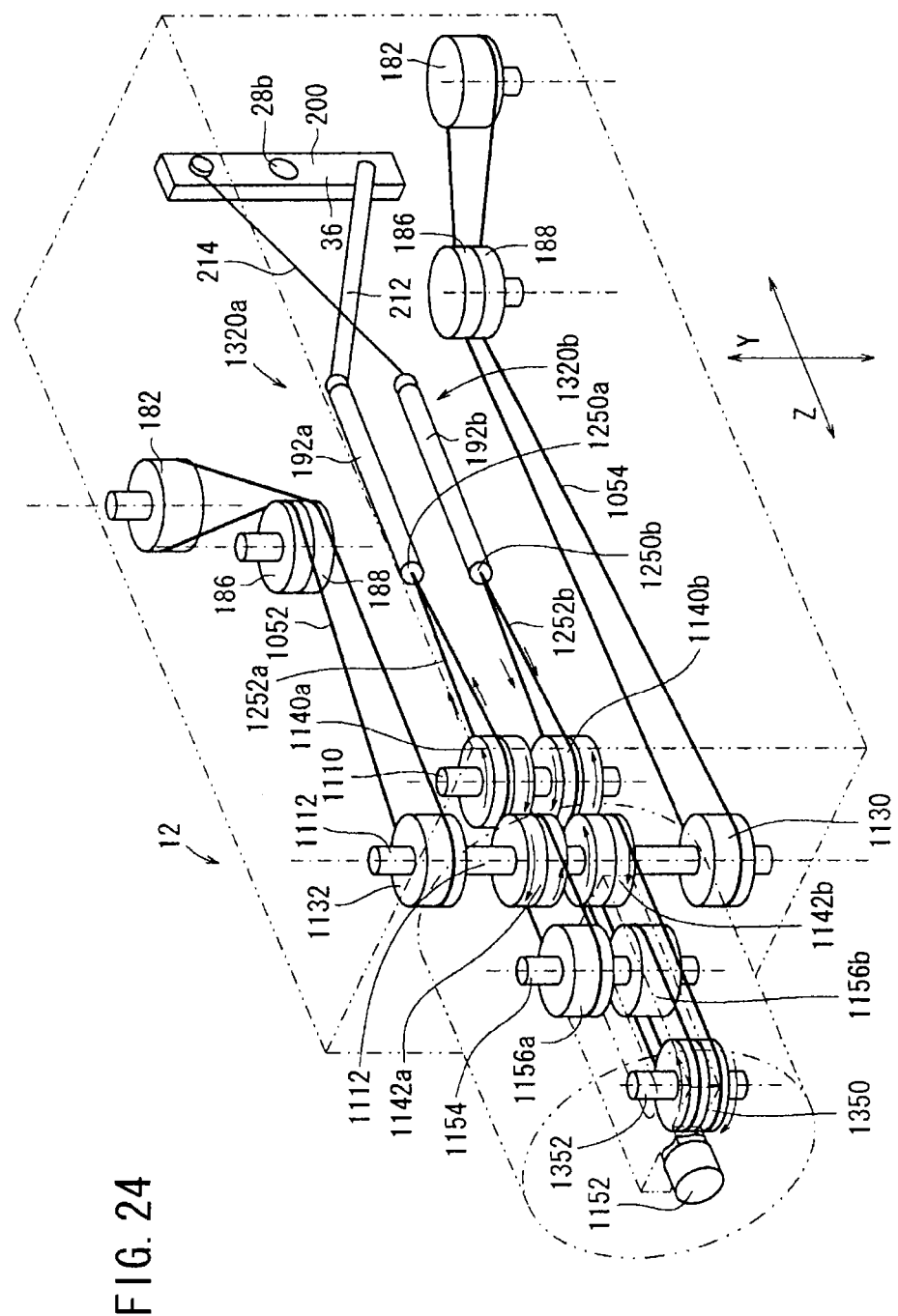
FIG. 24 is a schematic structural view of the end effector.
Figure 25:
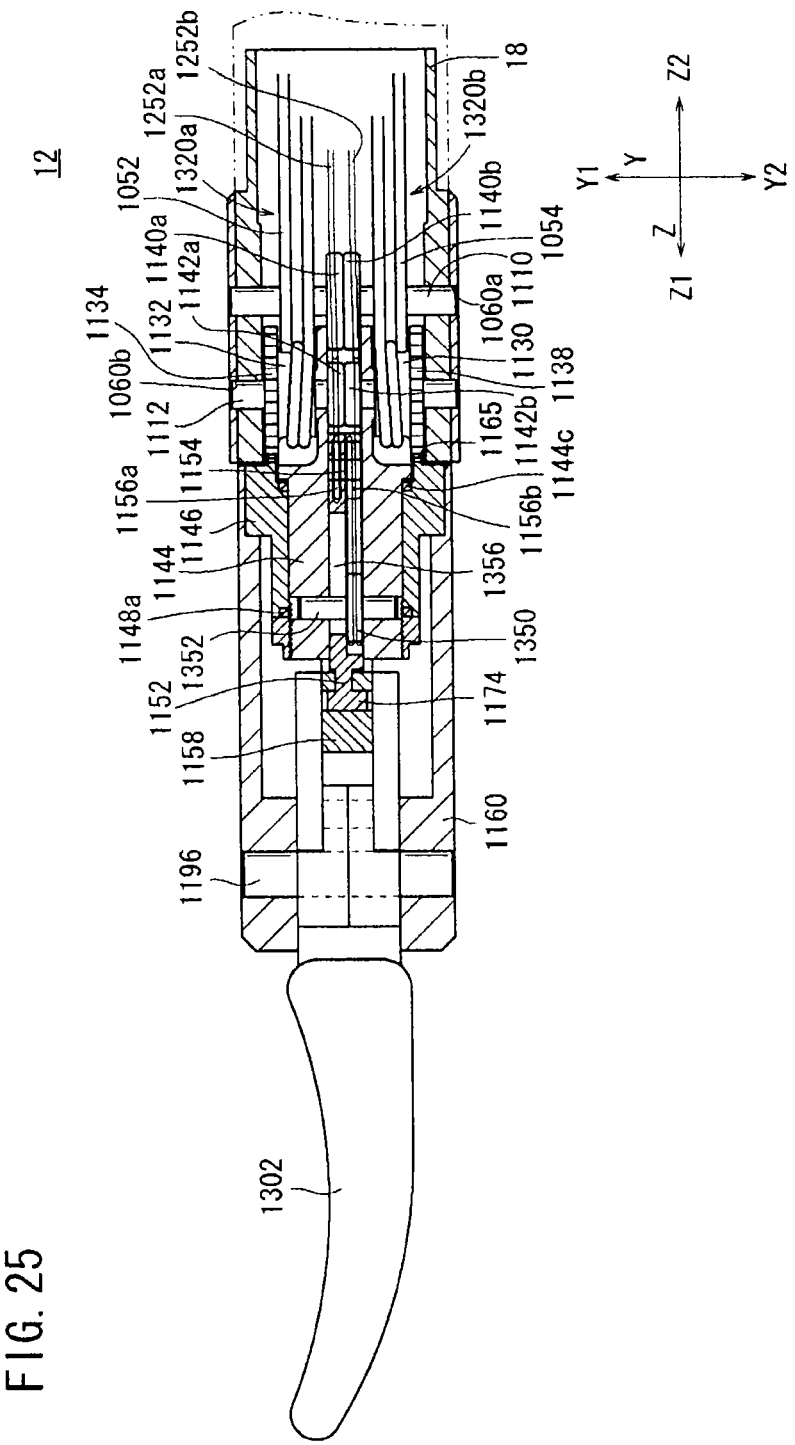
FIG. 25 is a sectional side view of the end effector.
Figure 26:
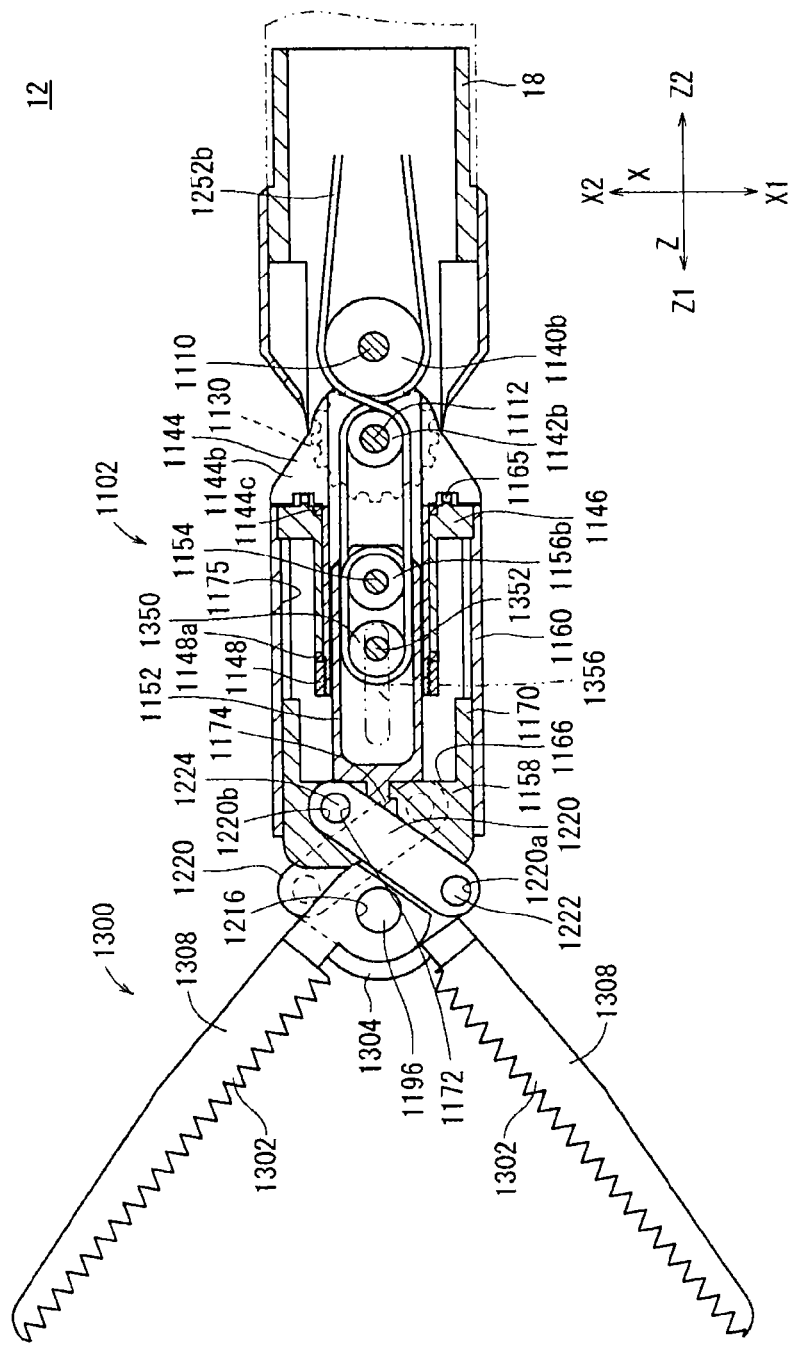
FIG. 26 is a sectional plan view of the end effector.

For ease of understanding of the structure of the end effector 12, a schematic view thereof is shown in FIG. 24.

In the end effector 12 configured as above, as shown in FIG. 22, when the trigger lever 36 is sufficiently pulsed by a hand, the rod 192*a* draws the passive wire 1252*a*, whereby the passive pulley 1156*a* and the transmission member 1152 are moved in the Z2 direction, so that the end effector elements 1300 can be closed. Thus, the end effector elements 1300 are closed by traction of the transmission members such as the rod 192*a*, the passive wire 1252*a*, the passive pulley 1156*a*, etc.

In this case, with respect to the second end effector driving mechanism 1320*b*, the rod 192*b* is disposed to be pushed forward and, therefore, motions of the transmission member 1152 are not hampered.

In addition, as shown in FIG. 23, when the trigger lever 36 is sufficiently pushed forward by a hand, the transmission member 1152 and the passive pulley 1156*a* are moved toward the distal side, namely, in the Z1 direction, whereby the end effector elements 1300 can be opened.

Since the force with which the trigger lever 36 is pushed forward by the hand is transmitted mechanically and directly to the end effector elements 1300 by the second end effector driving mechanism 1320*b*, the end effectors element 1300 can be opened by an arbitrary strong force, instead of a predetermined force as in the case of an elastic body. Accordingly, this configuration can be preferably applied to such procedures as stripping a living tissue, or opening a hole part wider, by use of an outside surface of the end effector elements 1300.

Besides, in the case where an object (target matter) comes into contact with the outside surface of the end effector elements 1300, the passive wire 1252*b*, the rod 192*b* and the trigger lever 36 also would not be moved further in the Z1 direction. Therefore, the operator can recognize the contact of the outside surface of the end effector elements 1300 with the object, the hardness of the object, etc. through tactile sensation at fingertips.

The end effector 12 is capable of performing yaw-axis motions and roll-axis motions. Although not illustrated in the drawings, in the case where the end effector 12 performs yaw-axis motions, the composite mechanism part 1102 and the end effector elements 1300 which are located on the distal side relative to the shaft of the guide pulley 1142*a* and the guide pulley 1142*b* (see FIG. 24) are oscillated in the yaw direction about the shaft. Since the end effector 12 is a non-interference mechanism, even upon a yaw-axis motion, the opening of the end effector elements 1300 is not changed. On the other hand, a change in the opening of the end effector element 1300 does not cause a yaw-axis motion. The same applies also to the relationship between the end effector elements 1300 and the roll-axis motions.

Figure 27:
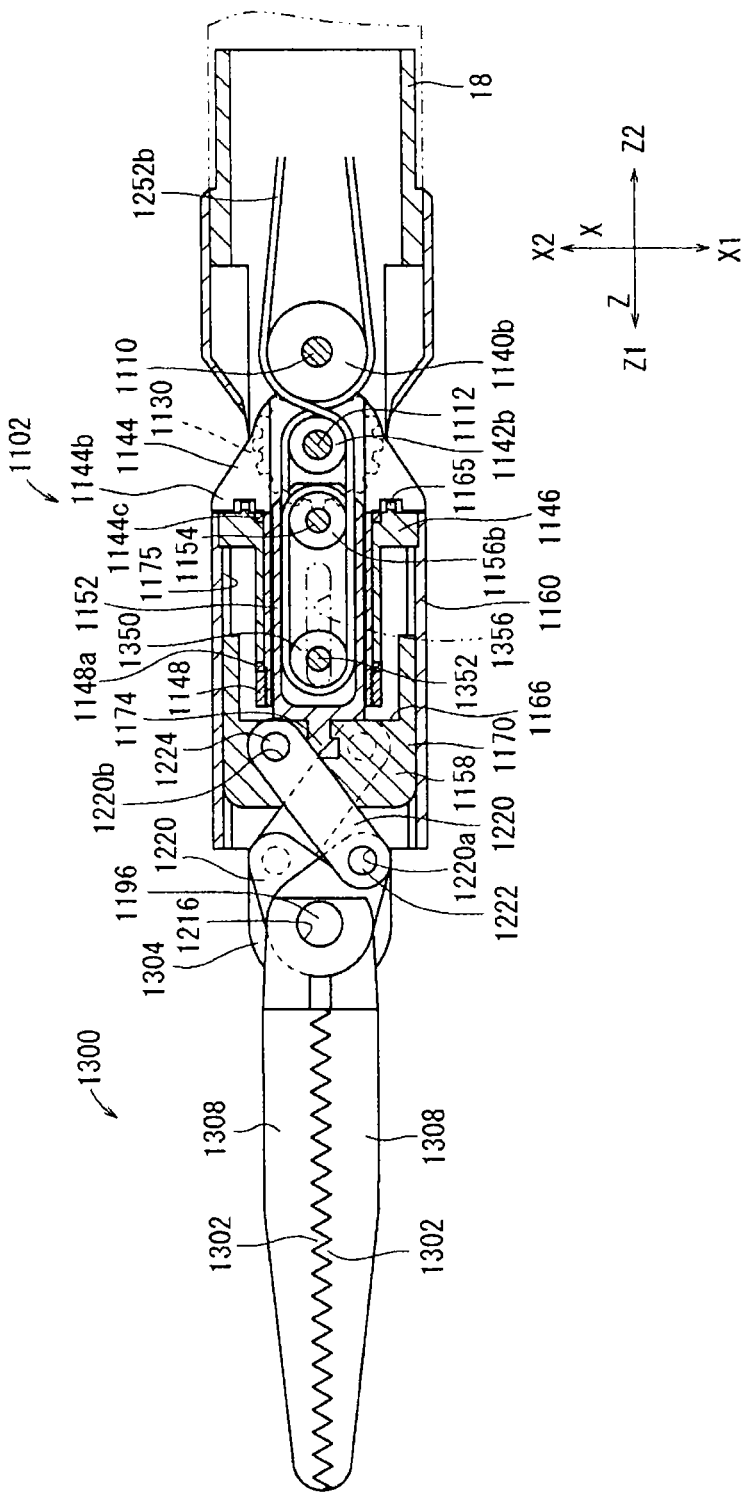
FIG. 27 is a sectional side view of the end effector in the condition where a gripper is closed.
Figure 28:
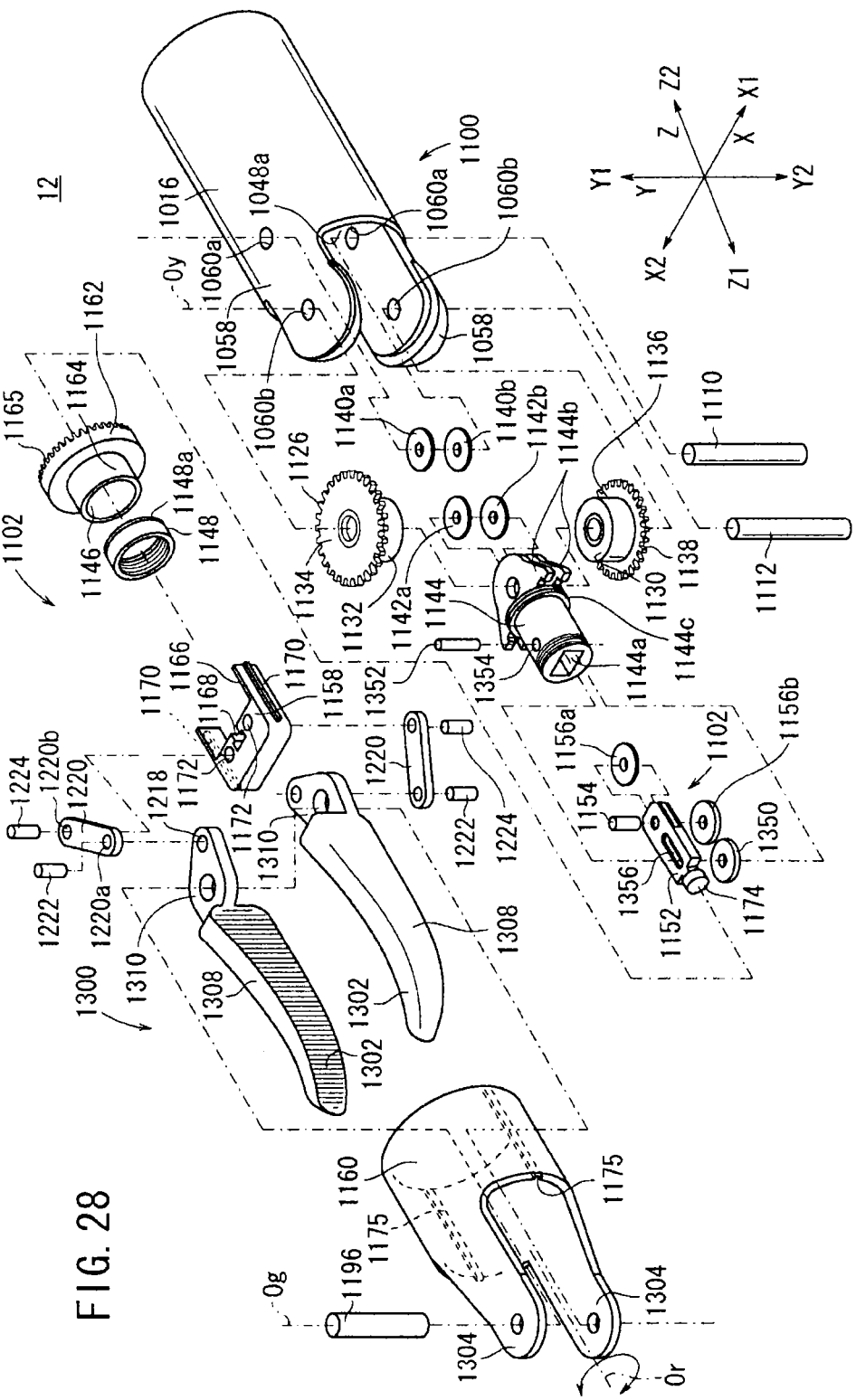
FIG. 28 is an exploded perspective view of the end effector.

As understood from FIGS. 24 and 27, in the end effector 12, under the action of the wires 1052 and 1054, the gears 1134 and 1138 are rotated to drive the face gear 1165. When the gears 1134 and the 1138 are rotated in the same direction at the same speed, a yaw-axis motion is realized. When the gears 1134 and 1138 are rotated in opposite directions at the same speed, a roll-axis motion is obtained. When the rotating speeds of the gears 1134 and 1138 are different, a composite motion relating to both the yaw axis and the roll axis is caused. In short, the mechanism of the end effector 12 is a differential mechanism that performs motions according to the difference in rotation between the gear 1134 and the gear 1138.

The mechanism of the end effector 12 is not limited to such a differential mechanism. For instance, a mechanism may be adopted in which the wire 1052 drives the face gear 1165 through the gear 1134, whereas the wire 1054 directly drives the main shaft member 1144 to rotate.

Now, an end effector 12a as a modification of the end effector 12 will be described below referring to FIG. 36.

Figure 36:
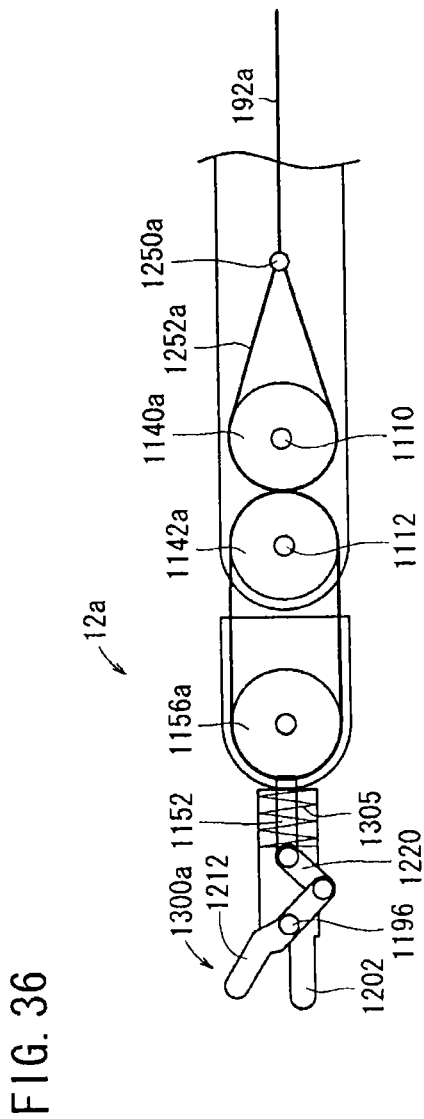
FIG. 36 is a schematic structural view of an end effector according to a modification.

As shown in FIG. 36, the end effector 12a is the same as the end effector 12 (see FIG. 23) in that the first end effector driving mechanism 1320a is provided, but is different from the end effector 12 in that the second end effector driving mechanism 1320b is omitted. The same components of the end effector 12a as those of the end effector 12 above are denoted by the same reference symbols as used above, and detailed descriptions of them will be omitted in the following.

The end effector 12a has end effector elements 1300a of a one side opening type in place of the above-mentioned end effector elements 1300 of the both side opening type. The end effector element 1300a has a stationary gripper 1202, a gripper 1212 capable of opening and closing motions with a pin 1196 as a center axis, and a spring 1305 that elastically biasesa transmission member 1152 in the Z1 direction. As the transmission member 1152 is advanced and retracted, the gripper 1212 is driven through a gripper link 1220 to open and close. Specifically, when the trigger lever 36 is pulsed in the Z2 direction, the transmission member 1152 is also displaced in the Z2 direction by the first end effector driving mechanism 1320a, and the gripper 1212 is turned counterclockwise in FIG. 36, whereby the end effector elements 1300 are put into a closing motion. On the other hand, when the trigger lever 36 is released, the transmission member 1152 is displaced in the Z1 direction under the biasing by the spring 1305, whereby the end effector elements 1300 are returned into an open state. Besides, the trigger lever 36 is returned in the Z1 direction.

As has been described above, according to the manipulator 10 in this embodiment, the rotation operating part 54 is provided with the finger holder at the outer peripheral surface thereof, and is operated to turn in the circumferential direction, whereas the tilt operating part 56 is operated to tilt by pushing-in of the tilting plate 76. This ensures that respective intuitive operability can be obtained as to the rolling mechanism and the pivot axis mechanism. In addition, the finger holder of the rotation operating part 54 is provided on the radially outer side relative to an end portion of the tilt operating part 56. As a result, appropriate use of the rotation operating part 54 and the tilt operating part 56 according to the purpose can be realized easily, so that even an operator accustomed to conventional forceps can easily use the manipulator 10.

Meanwhile, during a surgical procedure conducted using the manipulator 10, the operator may grip or hold an upper portion of the manipulator 10 with a hand opposite to the hand with which the handle grip 26 has been gripped, in order to re-grip the handle grip 26 or for momentarily putting the hand off the handle grip 26. In such a situation, there is a risk that the operator's hand may touch the rotation operating part, resulting in that the turning mechanism is operated unintentionally. Upon the occurrence of such a misoperation of the rotation operating part, it may be impossible to carry out a smooth procedure.

Now, in consideration of this problem, some configuration examples for preventing the rotation operating part from being operated erroneously will be described below. Incidentally, the left-right direction, with respect to the manipulator 10 pertaining to the embodiment, means the direction orthogonal to the plane containing the direction in which the connector shaft 18 extends and the direction in which the grip handle 26 extends.

First, referring to FIGS. 37 and 38, description will be made of a mechanism that partly covers the rotation operating part to thereby inhibit a hand from touching the rotation operating part and to prevent the rotation operating part from being operated erroneously.

Figure 37:
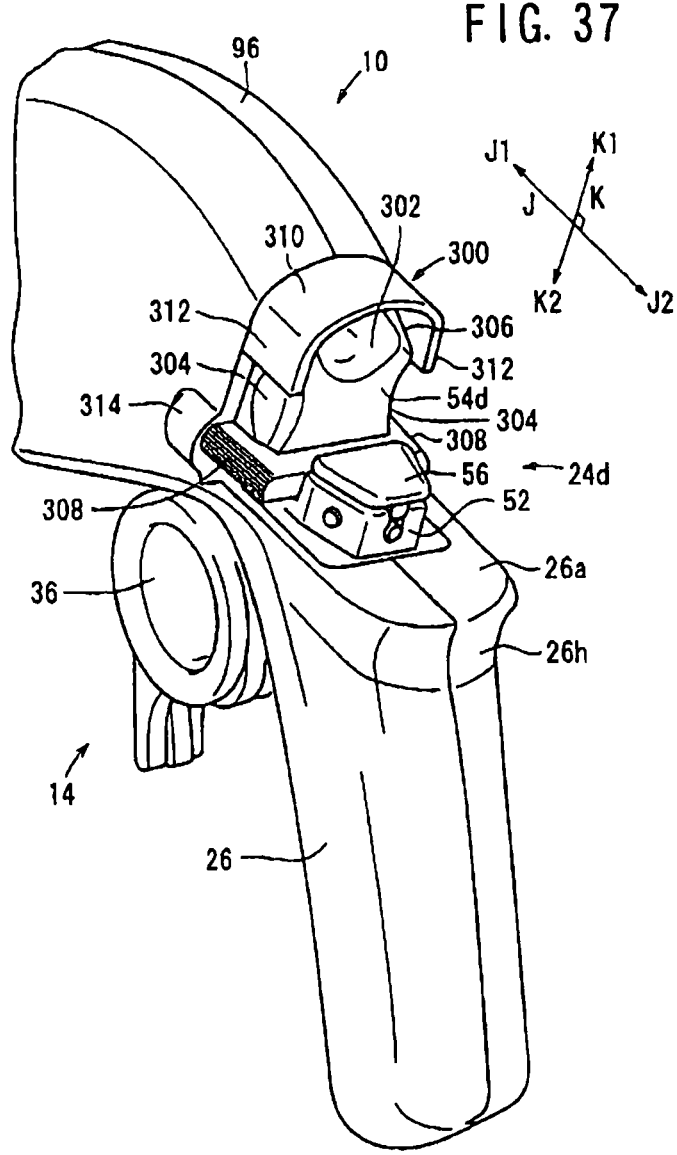
FIG. 37 is a perspective view of a misoperation preventive cover according to a first configuration example and the vicinity thereof.

FIG. 37 is a perspective view of a composite input unit 24d and a misoperation preventive cover 300 according to a fourth modification and the vicinity thereof. A rotation operating part 54d in the composite input unit 24d according to the fourth modification is about a size smaller than the rotation operating part 54c shown in FIG. 14. The rotation operating part 54d has an operating element 306 formed in an arcuate shape at its upper portion, and side parts 308 provided on the lower side of the operating element 306 and bulging to left and right outer sides.

The operating element 306 is provided at an upper end portion and both left and right sides thereof with notches 302 and 304 formed in a recessed form. The upper end portion of the operating element 306 is located at substantially the same position as or on the inner side (K2 side) of an outside surface of a cover 96, and, at least, it does not protrude to the outer side (K1 side) of the outside surface of the cover 96.

As shown in FIG. 37, in order to prevent the rotation operating part 54d from being operated erroneously, the manipulator 10 is provided with a misoperation preventive cover 300 according to a first configuration example which covers at least a part of the rotation operating part 54d. The misoperation preventive cover 300 according to the first configuration example is formed to cover an upper portion of the rotation operating part 54d.

Specifically, the misoperation preventive cover 300 in the first configuration example is provided at a proximal portion (a J2-side end portion) of the cover 96 disposed on the front side of the rotation operating part 54d. In the example shown, the misoperation preventive cover 300 is a member attached to the cover 96, but it may be formed integral with the cover 96.

In addition, the misoperation preventive cover 300 has an upper wall part 310 extending in the left-right direction so as to face and cover the notch 302 which is a finger holder provided at an upper end portion of the rotation operating part 54d, and side wall parts 312 facing and covering those portions of an upper portion of the rotation operating part 54*d* which are located on both sides (both left and right sides) in the turning direction of the rotation operating part 54*d*.

The upper wall part 310 is formed in an arcuate shape along the shape of an upper portion of the operating element 306. The length (height) of the side wall parts 312 in the K direction is so set that left and right side surfaces, exclusive of an upper portion, of the rotation operating part 54*d* are exposed. The lengths of the upper wall part 310 and the side wall parts 312 in the J direction are preferably so set that J2-side end portions of the upper wall part 310 and the side wall parts 312 are located at substantially the same positions as, or on the J2 side relative to, a J2-side surface (front surface) of the operating element 306.

Where the misoperation preventive cover 300 configured as above is provided, even when that upper portion of the manipulator 10 which is near the rotation operating part 54*d* (for example, a proximal portion of the cover 96) is gripped or held by an operator, the operator's hand is inhibited from touching the rotation operating part 54*d*, since the upper side of the rotation operating part 54*d* is covered by the misoperation preventive cover 300. Consequently, the rotation operating part 54*d* is prevented from being operated erroneously.

In addition, when that upper portion of the manipulator 10 which is near the rotation operating part 54*d* is gripped or held by the operator, an upper portion of the rotation operating part 54*d* is most liable to come close to the operator's hand. However, the operator's hand is effectively inhibited from touching the rotation operating part 54*d*, since the misoperation preventive cover 300 is so formed as to cover the upper portion of the rotation operating part 54*d*.

Incidentally, the left and right side surfaces exclusive of an upper portion of the rotation operating part 54*d* are not covered by the misoperation preventive cover 300 but are exposed to the outside. Therefore, the operator can depress these exposed portions with a finger, so that a lowering in operability of the rotation operating part 54*d* is obviated.

As shown in FIG. 37, the operating unit 14 is provided, on front side surfaces of the side parts 308, with protuberant parts 314 bulging to the left and right outer sides. The side parts 308 are located on the inner side in the left-right direction relative to the protuberant parts 314. Specifically, the left and right outer ends of the side parts 308 are located on the inner side relative to the left and right outer ends of the protuberant parts 314.

Thus, even where the rotation operating part 54*d* has the side parts 308 bulging in the left-right directions, the operator's hand is less liable to touch the side part 308 when that upper portion of the manipulator 10 which is near the rotation operating part 54*d* is gripped or held by the operator, since the side parts 308 are located on the inner side in the left-right direction relative to the protuberant parts 314. Therefore, the rotation operating part 54*d* is restrained from being operated erroneously.

Figure 38:
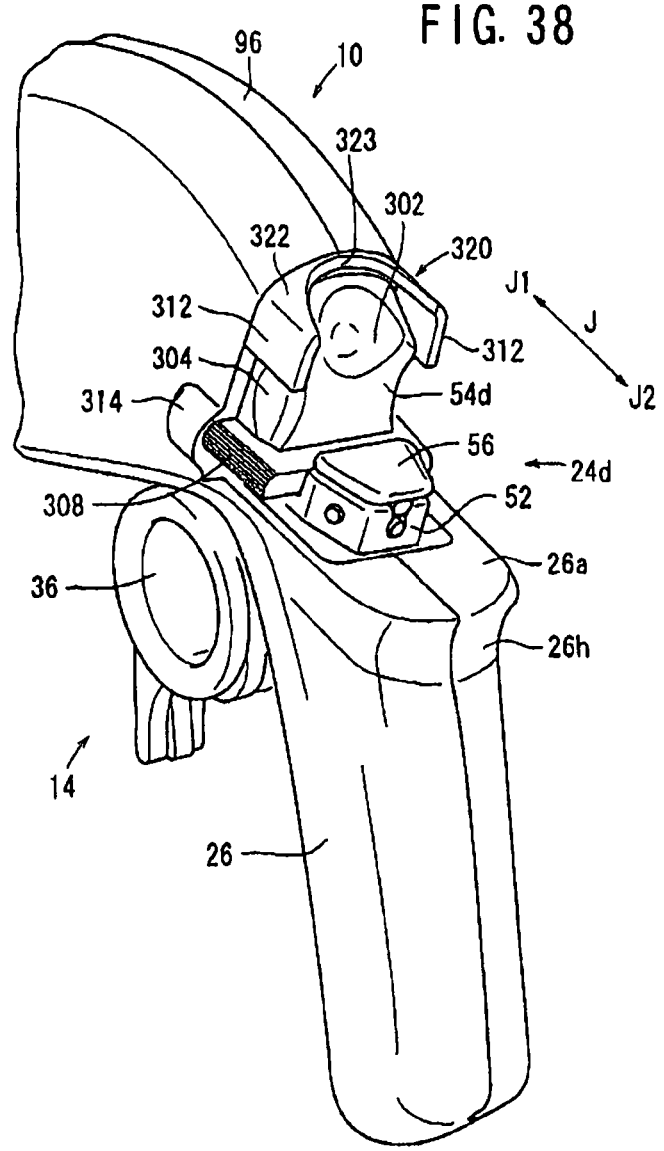
FIG. 38 is a perspective view of a misoperation preventive cover according to a second configuration example and the vicinity thereof.

FIG. 38 is a perspective view of a misoperation preventive cover 320 according to a second configuration example and the vicinity thereof. The misoperation preventive cover 300 in the first configuration example described above is so formed as to cover not only the left and right side surfaces of the upper portion of the rotation operating part 54*d* but also the upper end portion of the upper portion. On the other hand, as shown in FIG. 38, the misoperation preventive cover 320 in the second configuration example is so structured as to cover left and right side surfaces of an upper portion of the rotation operating part 54*d* and to expose the notch 302 which is a finger holder provided at an upper end portion of the rotation operating part 54*d*. Specifically, the misoperation preventive cover 320 has an upper wall part 322 formed with a cutout 323 that exposes the notch 302 provided at the upper end portion of the rotation operating part 54*d*.

Thus, the misoperation preventive cover 320 in the second configuration example is so formed as to expose the notch 302 which is a finger holder, so that the misoperation preventive cover 320 does not obstruct the operator when the operator puts a finger on the finger holder. Therefore, misoperation of the rotation operating part 54*d* can be prevented, without lowering the operability of the rotation operating part 54*d*.

FIG. 39 is a perspective view of a misoperation preventive cover 330 according to a third configuration example and the vicinity thereof. In FIG. 39, the configurations other than the misoperation preventive cover 330 are the same as the configurations of the composite input unit 24*c* according to the third modification and the vicinity thereof as shown in FIG. 14.

The rotation operating part 54*c* has an operating element 71 provided with notches 72*e* as finger holders, and levers 72*a* provided on the lower side of the operating element 71 and bulging to the left and right outer sides relative to the operating element 71. The operating unit 14 is provided, at J1-side positions of the levers 72*a* (at parts of a cover 96) with protuberant parts 331 bulging in the left-right directions.

In the manipulator 10 shown in FIG. 39, misoperation preventive covers 330 each covering at least a part of the lever 72*a* are provided, that prevents the rotation operating part 54*d* from being operated erroneously. The misoperation preventive cover 330 is a member extending in the J direction, and is attached to the protuberant part 331.

The misoperation preventive cover 330 extends in the J2 direction from the protuberant part 331, and, in the example shown, is so sized as to cover roughly a lower half of the lever 72*a*. The position of the J2-side end of the misoperation preventive cover 330 is preferably at the same position as, or on the J2 side of, the center position of the lever 72*a* in the J2 direction. In other words, the misoperation preventive cover 330 is preferably so sized as to cover at least a former half, along the J2 direction, of the lever 72*a*.

Where the misoperation preventive covers 330 configured as above are provided, the misoperation preventive covers 330 covering the levers 72*a* inhibit the operator's hand from touching the levers 72*a* and, hence, the rotation operating part 54*c* is prevented from being operated erroneously, even in the case where the rotation operating part 54*c* has the levers 72*a* bulging in the left-right directions.

Figure 40A:
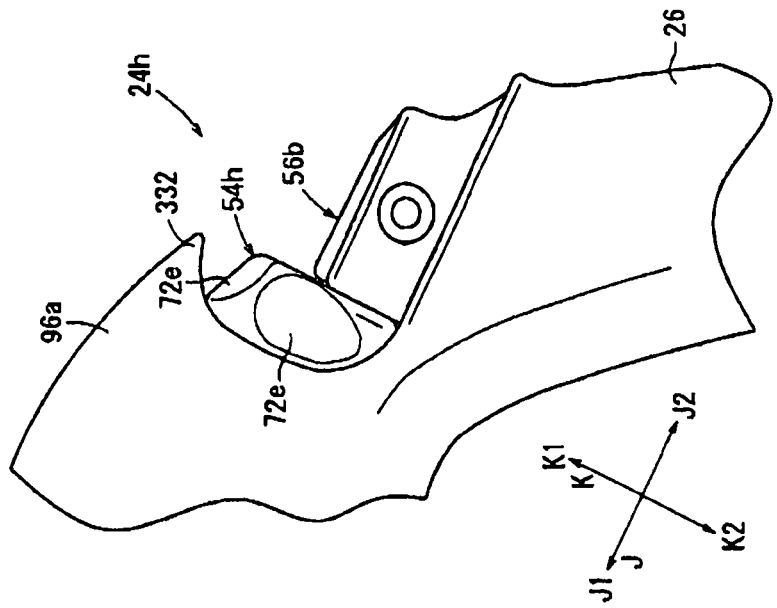
FIG. 40A is a perspective view of a composite input unit according to a fifth modification and a misoperation preventive cover according to a fourth configuration example and the vicinity thereof.
Figure 40B:
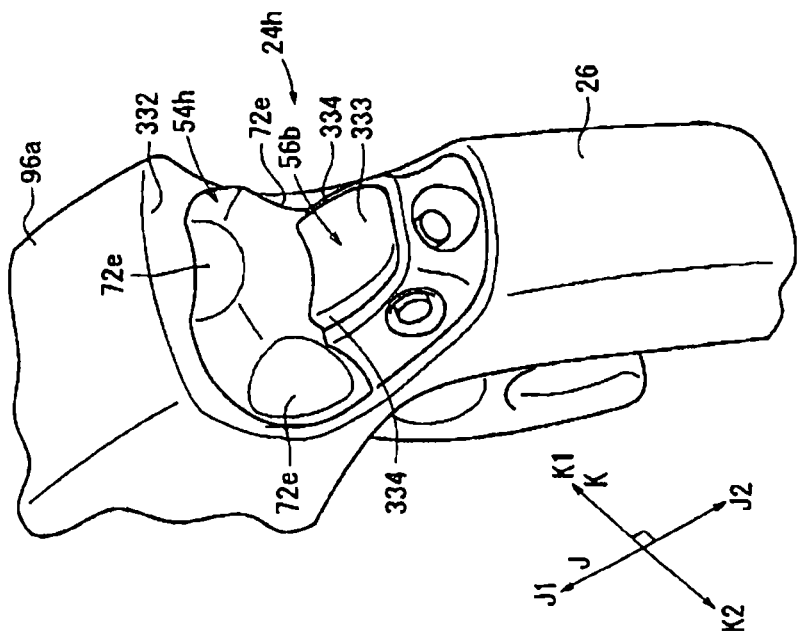
FIG. 40B is a side view of a composite input unit according to a fifth modification and a misoperation preventive cover according to a fourth configuration example and the vicinity thereof.

FIG. 40A is a perspective view of a composite input unit 24*h* according to a fifth modification and a misoperation preventive cover 332 according to a third configuration example and the vicinity thereof. FIG. 40B is a side view of a composite input unit 24*h* according to a fifth modification and a misoperation preventive cover 332 according to a third configuration example and the vicinity thereof.

The rotation operating part 54*h* of the composite input unit 24*h* is constructed to be size smaller than the rotation operating part 54*c* illustrated in FIG. 14 and has notches 72*e* as finger holders operating element 71 at the upper, right and left sides of the rotation operating part 54*h*.

An outer circumference of the rotation operating part 54*h* is located in medially in an outer circumference of a cover 96*a*. In the other words, the horizontal width of the cover 96*a* is wider than the horizontal width of the rotation operating part 54h and the top of the cover 96a is located in higher position than the top of the rotation operating part 54h.

As shown in FIGS. 40A and 40B, the misoperation preventive cover 332 is protruded to J2 direction at the upper portion of the rotation operating part 54h. In the illustrated embodiment, the misoperation preventive cover 332 is integrally constructed with the cover 96a at the upper part of the proximal portion of the cover 96a and extended to the horizontal direction. The protruded end of the misoperation preventive cover 332 is located in J2 direction from the distal end (i.e., J1 side end) of the rotation operating part 54h.

Where the misoperation preventive cover 332 configured as above is provided, even when that upper portion of the manipulator 10 which is near the rotation operating part 54h (for example, a proximal portion of the cover 96a) is gripped or held by an operator, the operator's hand is inhibited from touching the rotation operating part 54h, since the upper side of the rotation operating part 54h is covered by the protruded end of the misoperation preventive cover 332.

A tilt operating part 56b which is a part of the composite input unit 24e comprises a concave 333 at a central portion of the upper side and protruded portions 334 at the both side of the concave 333. The protruded portions 334 protrude to K1 direction. An operator's finger on the concave 333 is stabilized by this structure. Furthermore, the protruded portions 334 make it easy to push the tilt operating part 56b by the operator.

Figure 41:
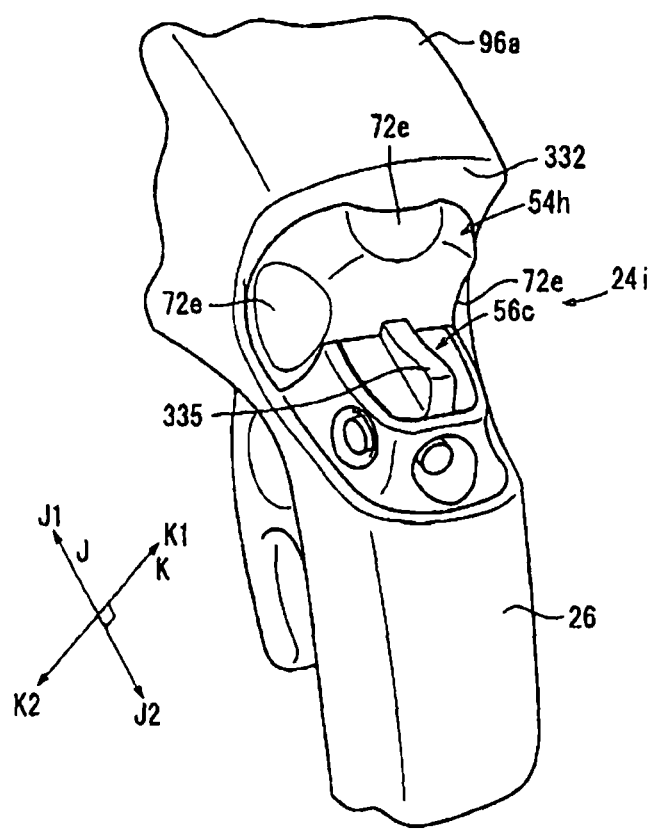
FIG. 41 is a perspective view of a composite input unit according to a sixth modification, and the vicinity thereof.

FIG. 41 is a perspective view of a composite input unit 24i according to a sixth modification, and the vicinity. The composite input unit 24i comprises a tilt operating part 56c which is an alternative structure of the tilt operating part 56b of fifth modification. The tilt operating part 56c comprises a protruded portion 335 which is protruded to an opposite side of the grip handle 56 (i.e., K1 direction) and extended to J direction. The protruded portions 334 make it easy to incline the tilt operating part 56c to right and left directions by the operator.

Now, referring to FIGS. 42 to 46, a mechanism that prevents misoperation of the rotation operating part by a mechanical action will be described below.

Figure 42:
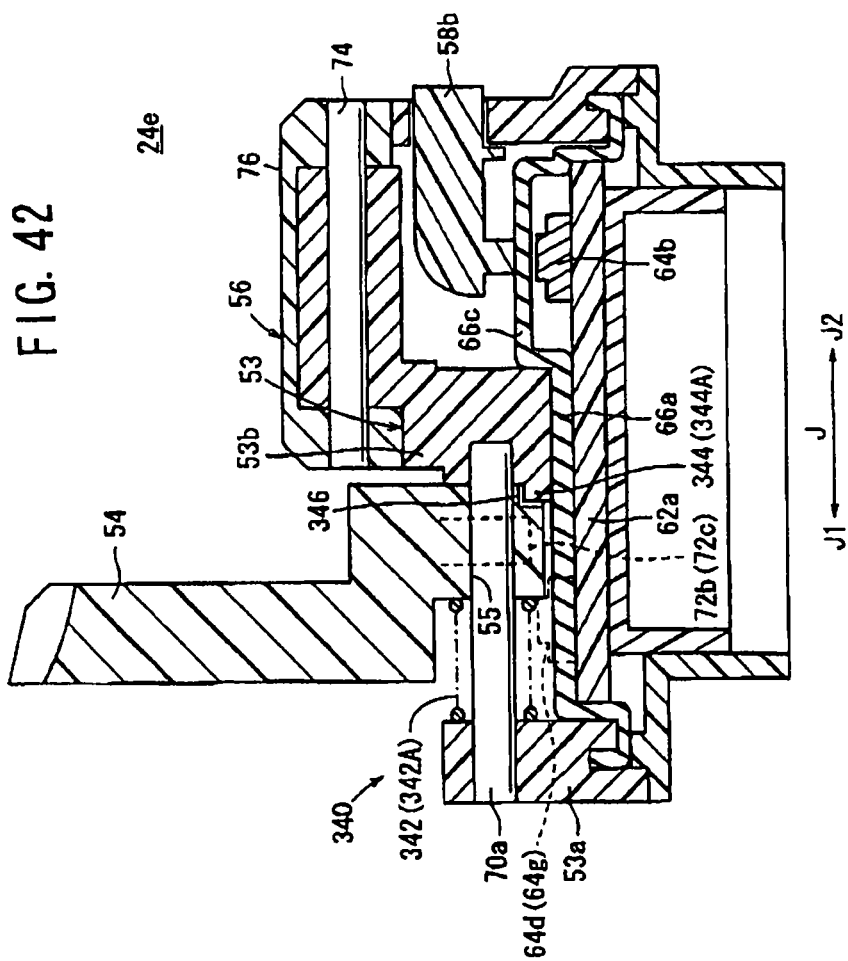
FIG. 42 is a sectional view of a composite input unit according to a seventh modification when the rotation operating part is in a non-operating position.

FIG. 42 is a sectional view of a composite input unit 24e according to a seventh modification when a rotation operating part 54 is in a non-operating position. FIG. 42 is a sectional view of the composite input unit 24e in the seventh modification when the rotation operating part 54 is in an operating position. Incidentally, in FIGS. 42 and 43, the same reference symbols as those in FIG. 5 basically denote the components which are the same as or similar to the above-described ones and which are deemed as exhibiting functions and effects the same as or similar to the above-described ones; therefore, detailed description of these components will be omitted.

The composite input unit 24e is provided with a misoperation preventive mechanism 340 that prevents the rotation operating part 54 from being operated erroneously. The misoperation preventive mechanism 340 is so configured as to cause a motion of a turning mechanism by the rotation operating time 54 to be impossible when the rotation operating part 54 is in a first state (the state shown in FIG. 42) and as to cause the motion of the turning mechanism by the rotation operating part 54 to be possible when the rotation operating part 54 is in a second state (the state shown in FIG. 43).

The misoperation preventive mechanism 340 has a rotating shaft 70a that supports the rotation operating part 54 turnably in the left-right directions and that guide it movably in the axial direction (J direction), and a spring (in the example shown, a coil spring) 342A as biasing mechanism 342 that constantly biases the rotation operating part 54 in the J2 direction.

The rotating shaft 70 is secured to a housing 53 by fixing a distal portion (J1-side end portion) to a front-side wall part 53a of the housing 53 and fixing a rear end portion (J2-side end portion) to an intermediate wall part 53b of the housing 53. Incidentally, the housing 53 is basically the same in configuration and function as the housing 52 shown in FIG. 5 in that it is a member that attaches a rotation operating part 54 and a tilt operating part 56 and accommodating a switch board 62a. However, the housing 53 is different from the housing 52 in that the spacing between the front-side wall part 53a and the intermediate wall part 53b is set larger than that in the housing 52 so that the rotation operating part 54 can be moved in the J directions.

The rotation operating part 54 is provided in its lower portion with an insertion hole 55 penetrating in the J direction, and the rotating shaft 70a is inserted in and passed through the insertion hole 55. The length of the rotating shaft 70a is set to be larger than the distance from a J2-side surface of the front-side wall part 53a to a J1-side surface of the intermediate wall part 53b. In addition, the distance from the J2-side surface of the front-side wall part 53a to the J1-side surface of the intermediate wall part 53b is so set that the rotation operating part 54 can be moved in the axial direction (J direction) of the rotating shaft 70a by a distance corresponding to the spacing between a position corresponding to the first state and a position corresponding to the second state.

A spring 342A as the biasing mechanism 342 according to a configuration example is disposed between the front-side wall part 53a and the rotation operating part 54 of the housing 53, with the rotating shaft 70a inserted therein, and constantly biases the rotation operating part 54 in the J2 direction. Incidentally, the configuration and the layout position of the biasing mechanism 342 are not limited to those shown in the drawing, and may be set otherwise insofar as the biasing mechanism can bias the rotation operating part 54 in the J2 direction.

As above-mentioned, the rotation operating part 54 can be moved in the axial direction (J direction) with the rotating shaft 70a as a guide, and is constantly biased in the J2 direction by the biasing mechanism 342. Therefore, the rotation operating part 54 is located in a non-operating position shown in FIG. 42 when not receiving a forward force (a force in the J1 direction), and is moved in the J1 direction to an operating position shown in FIG. 43 when receiving a force in the J1 direction in excess of the resilience of the spring.

The switch board 62a is provided thereon with tact switches 64d and 64g that actuate the turning mechanism, like the switch board 62 (see FIG. 5). The configurations and functions of the tact switches 64d and 64g are similar to those of the tact switches 64d and 64g shown in FIG. 9.

As shown in FIG. 42, the first state of the rotation operating part 54 is a state in which the rotation operating part 54 is in a "non-operating position" retracted toward the J2 side and away from a position where the tact switches 64d and 64g can be depressed. Specifically, in the first state, press protrusions 72b and 72c (see FIG. 6, as well) provided in the rotation operating part 54 are located at positions deviated from the positions facing the tact switches 64d and 64g, so that the rotation operating part 54 is in the state in which the tact switches 64d and 64g cannot be depressed.

Figure 43:
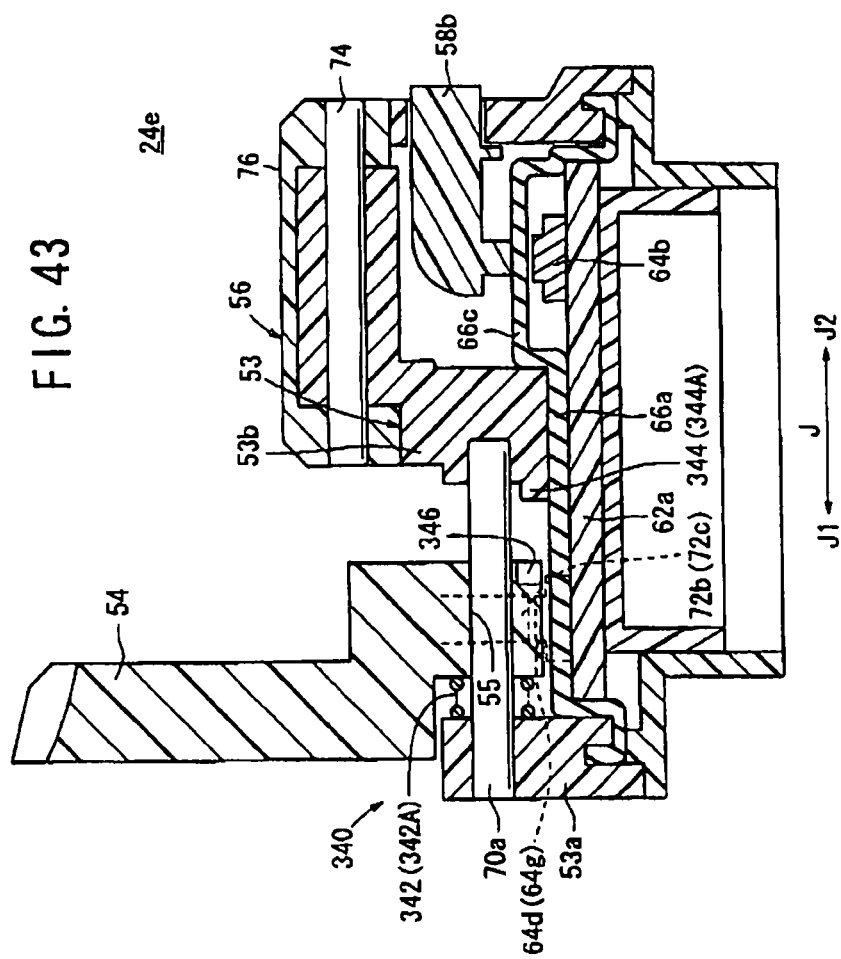
FIG. 43 is a sectional view of a composite input unit according to the seventh modification when the rotation operating part is in an operating position.

On the other hand, when the rotation operating part 54 is pushed in the J1 direction, the rotation operating part 54 is put into the second state, as shown in FIG. 43. The second state of the rotation operating part 54 is a state in which the rotation operating part 54 is in an "operating position" where the tact switches 64*d* and 64*g* can be depressed. Specifically, in the second state, the press protrusions 72*b* and 72*c* are located at the positions facing the tact switches 64*d* and 64*g*, so that by rotating the rotation operating part 54 in these positions, the tact switches 64*d* and 64*g* can be depressed through a silicone body 66A.

In addition, as shown in FIG. 42, the misoperation preventive mechanism 340 further includes a rotation stopper 344 that inhibits rotation of the rotation operating part 54 when the rotation operating part 54 is located in the non-operating position. The rotation stopper 344 according to a configuration example is a protrusion body 344A provided (fixed) on a J1-side surface of the intermediate wall part 53*b*. By engagement of the rotation stopper 344 with a recess 346 provided in the rotation operating part 54 when the rotation operating part 54 is located in the non-operating position, rotation of the rotation operating part 54 is inhibited.

Since the misoperation preventive mechanism 340 is configured as above-described, the turning mechanism is not operated when the rotation operating part 54 is in the non-operating position; that is, operation of the turning mechanism by the rotation operating part 54 does not become possible unless the rotation operating part 54 is moved into the operating position. This promises effective prevention the rotation operating part 54 from being operated erroneously.

Specifically, when the rotation operating part 54 is in the non-operating position, even if the rotation operating part 54 is operated, the tact switches 64*d* and 64*g* would not be depressed by the rotation operating part 54. Besides, the tact switches 64*d* and 64*g* would not be depressed unless the rotation operating part 54 is intentionally moved into the operating position by the operator. Therefore, misoperation of the rotation operating part 54 is securely prevented.

In addition, when the rotation operating part 54 is located in the non-operating position, rotation of the rotation operating part 54 is inhibited by the rotation stopper 344. Therefore, the rotation operating part 54 is prevented from reaching the operating position by moving in the J1 direction while being in the state of having been rotated leftward or rightward from its neutral position. Consequently, the tact switches 64*d* and 64*g* are prevented from being depressed unexpectedly.

Besides, the operator attempting to operate the rotation operating part 54 can recognize that the rotation operating part 54 is in the non-operating position, based on the fact that the rotation of the rotation operating part 54 is being inhibited by the action of the rotation stopper 344. Therefore, the operator can easily understand that it is necessary to push the rotation operating part 54 in the J1 direction in order to make it possible to operate the turning mechanism.

Figure 44:
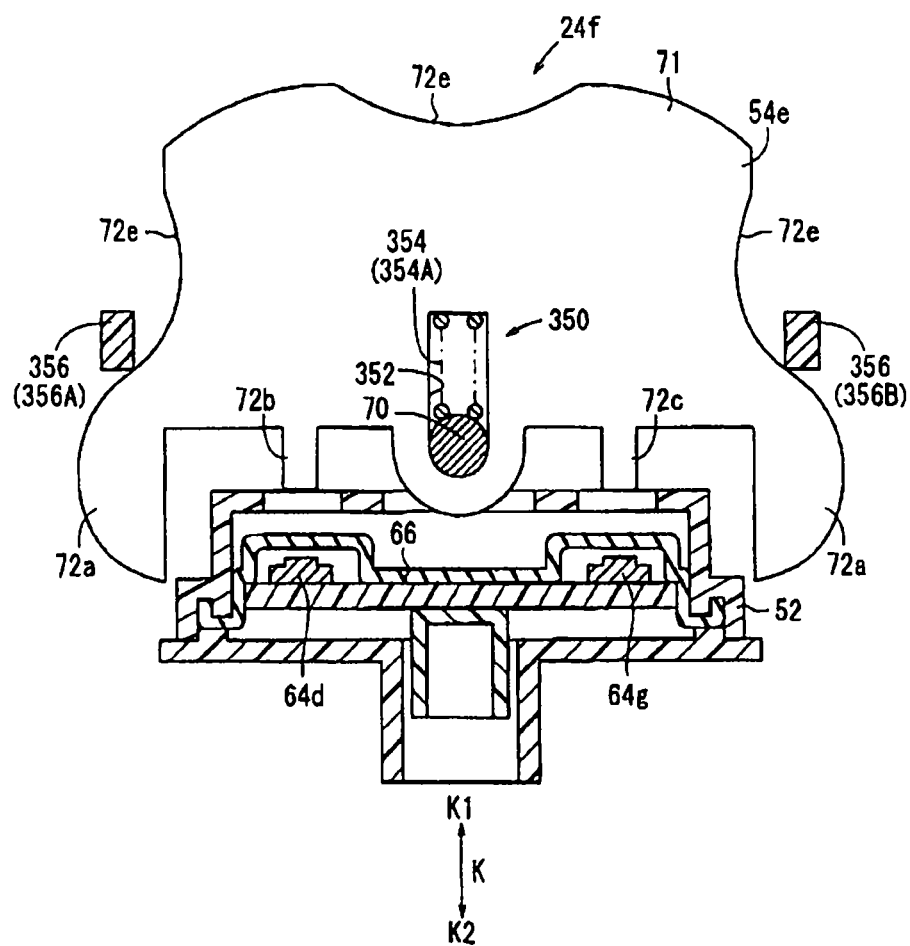
FIG. 44 is a sectional view of a part of a composite input unit according to a eighth modification when the rotation operating part is in the non-operating position.
Figure 45:
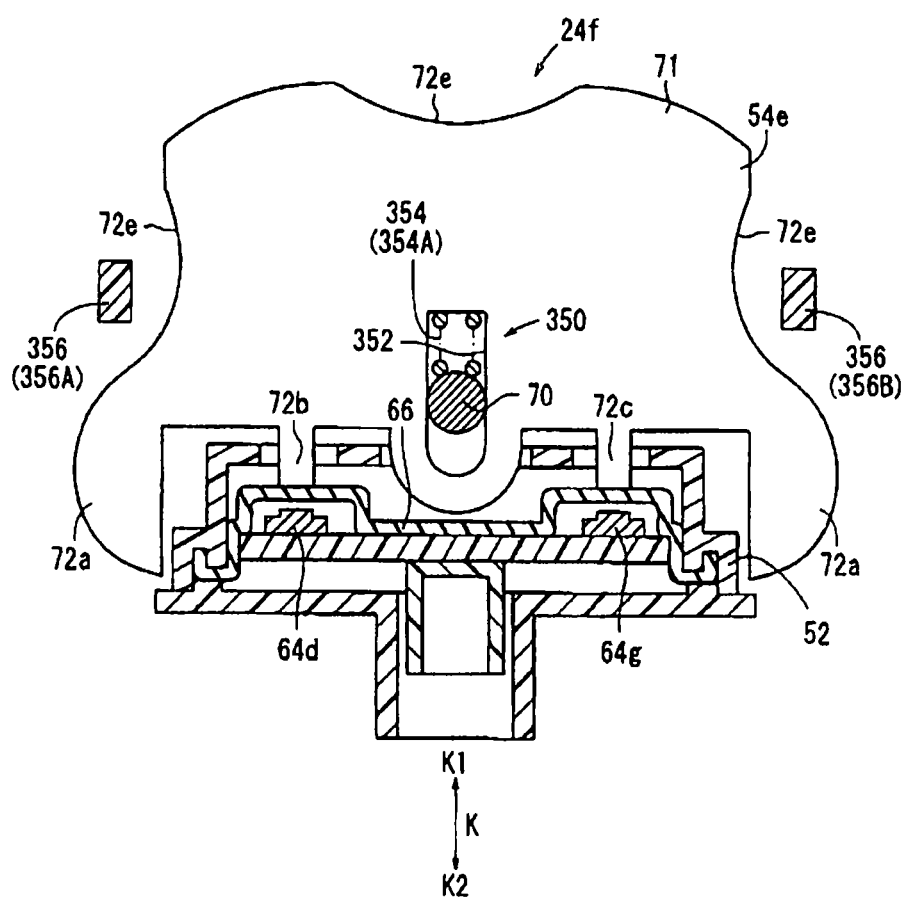
FIG. 45 is a sectional view of a part of the composite input unit according to the eighth modification when the rotation operating part is in the operating position.

FIG. 44 is a sectional view of a composite input unit 24*f* according to an eighth modification when a rotation operating part 54*e* is in a non-operating position. FIG. 45 is a sectional view of the composite input unit 24*f* in the eighth modification when the rotation operating part 54*e* is in an operating position. Incidentally, in FIGS. 44 and 45, the same reference symbols as those shown in FIG. 6 basically denote the components which are the same as or similar to the above-described ones and which are deemed as exhibiting the functions and effects the same as or similar to the above-described ones; therefore, detailed descriptions of these components will be omitted.

The composite input unit 24*f* is provided with a misoperation preventive mechanism 350 that prevents the rotation operating part 54*e* from being operated erroneously. The misoperation preventive mechanism 350 is so configured as to make impossible the operation of a turning mechanism by the rotation operating part 54*e* when the rotation operating part 54*e* is in a first state (the state shown in FIG. 44) and as to make possible the operation of the turning mechanism by the rotation operating part 54*e* when the rotation operating part 54*e* is in a second state (the state shown in FIG. 45).

As for overall shape, the rotation operating part 54*e* in the example shown here has an operating element 71 provided with notches 72*e* functioning as finger holders, and levers 72*a* provided at the lower side in the operating element 71 and bulging to the left-right directions, like the rotation operating part 54 shown in FIG. 6. However, the rotation operating part 54*e* may be similar to the rotation operating part 54*b* shown in FIG. 13 or the rotation operating part 54*c* shown in FIG. 14.

The rotation operating part 54*e* is provided, in its central portion in the left-right direction, with a slot 352 penetrating in the J direction (the direction orthogonal to the drawing in FIG. 44) and extending in the K direction. A shaft 70 is inserted through the slot 352, and the rotation operating part 54*e* is movable in the K directions with the shaft 70 as a guide. The slot 352 is one of the components of the misoperation preventive mechanism 350.

A spring 354A as biasing mechanism 354 that constantly biases the rotation operating part 54*e* in the K1 direction is disposed inside the slot 352. The biasing mechanism 354 is one of the components of the misoperation preventive mechanism 350. Incidentally, the configuration and layout position of the biasing mechanism 354 are not limited to those shown in the figure, and may be set otherwise insofar as the biasing mechanism 354 can bias the rotation operating part 54*e* in the K1 direction.

As above-mentioned, the rotation operating part 54*e* is movable in the K directions with the shaft 70 as a guide, and is constantly biased upward (in the K1 direction) by the biasing mechanism 354. Therefore, the rotation operating part 54*e* is located in a non-operating position shown in FIG. 44 when not receiving a downward force (a force in the K2 direction), and is moved in the K2 direction to an operating position shown in FIG. 45 when receiving a downward force in excess of the resilience of the spring.

As shown in FIG. 44, the first state of the rotation operating part 54*e* is a state in which the rotation operating part 54*e* is in a "non-operating position" retracted toward the K1 side and away from the position where tact switches 64*d* and 64*g* can be depressed. Specifically, in the first state, the distance from press protrusions 72*b* and 72*c* provided in the rotation operating part 54*c* to the tact switches 64*d* and 64*g* is so large that the rotation operating part 54*e* cannot depress the tact switches 64*d* and 64*g*.

On the other hand, when the rotation operating part 54*e* is pushed in the K2 direction, as shown in FIG. 45, the rotation operating part 54*e* is put into a second state. The second state of the rotation operating part 54*e* is a state in which the rotation operating part 54*e* is in an "operating position" where the rotation operating part 54*e* can depress the tact switches 64*d* and 64*g*. Specifically, in the second state, tip portions of the press protrusions 72*b* and 72*c* are in contact with a silicone body 66 and are proximate to the tact switches 64*d* and 64*g*. Therefore, by rotating the rotation operating part 54e in this position leftward or rightward, either one of the tact switches 64d and 64g can be depressed through the silicone body 66.

In addition, as shown in FIG. 44, the misoperation preventive mechanism 350 further includes a rotation stopper 356 that inhibits rotation of the rotation operating part 54e when the rotation operating part 54e is located in the non-operating position. The rotation stopper 356 in a configuration example makes contact with a part (in the example shown, the lever 72a) of the rotation operating part 54e when the rotation operating part 54e is located in the non-operating position, whereby rotation of the rotation operating part 54e is prevented.

More specifically, the rotation stopper 356 has a first stopper 356A provided on the left side of the rotation operating part 54e, and a second stopper 356B provided on the right side of the rotation operating part 54e. The first stopper 356A and the second stopper 356B are provided at those portions of an operating unit 14 which face the rotation operating part 54e.

As shown in FIG. 44, when the rotation operating part 54e is located in the non-operating position, an attempt to rotate the rotation operating part 54e to the right side cannot cause a rightward rotation of the rotation operating part 54e, since the rotation operating part 54e abuts on the first stopper 356A. In addition, when the rotation operating part 54e is located in the non-operating part, an attempt to rotate the rotation operating part 54e to the left side cannot produce a leftward rotation of the rotation operating part 54e, since the rotation operating part 54e abuts on the second stopper 356B.

On the other hand, as shown in FIG. 45, when the rotation operating part 54e has been moved downward and is located in the operating position, the rotation operating part 54e is separated from the first stopper 365A and the second stopper 356B, so that it can be rotated to the left side and to the right side.

Since the misoperation preventive mechanism 350 is configured as above, the turning mechanism would not be operated when the rotation operating part 54e is in the non-operating position, and operation of the turning mechanism by the rotation operating part 54e would not become possible unless the rotation operating part 54e is moved into the operating position. This promises effective prevention of the rotation operating part 54e from being operated erroneously.

Specifically, when the rotation operating part 54e is in the non-operating position, even if the rotation operating part 54e is operated, the tact switches 64d and 64g are not depressed by the rotation operating part 54e. Besides, the tact switches 64d and 64g are not depressed unless the rotation operating part 54e is intentionally moved into the operating position by the operator. Therefore, the rotation operating part 54e can be securely prevented from being operated erroneously.

In addition, the operator attempting to operate the rotation operating part 54e can recognize that the rotation operating part 54e is in the non-operating position, based on the fact that the rotation operating part 54e cannot be rotated, due to the action of the rotation stopper 356. Therefore, the operator can easily understand that it is necessary to push the rotation operating part 54e in the K2 direction in order to obtain a condition in which the turning mechanism can be operated.

Figure 46:
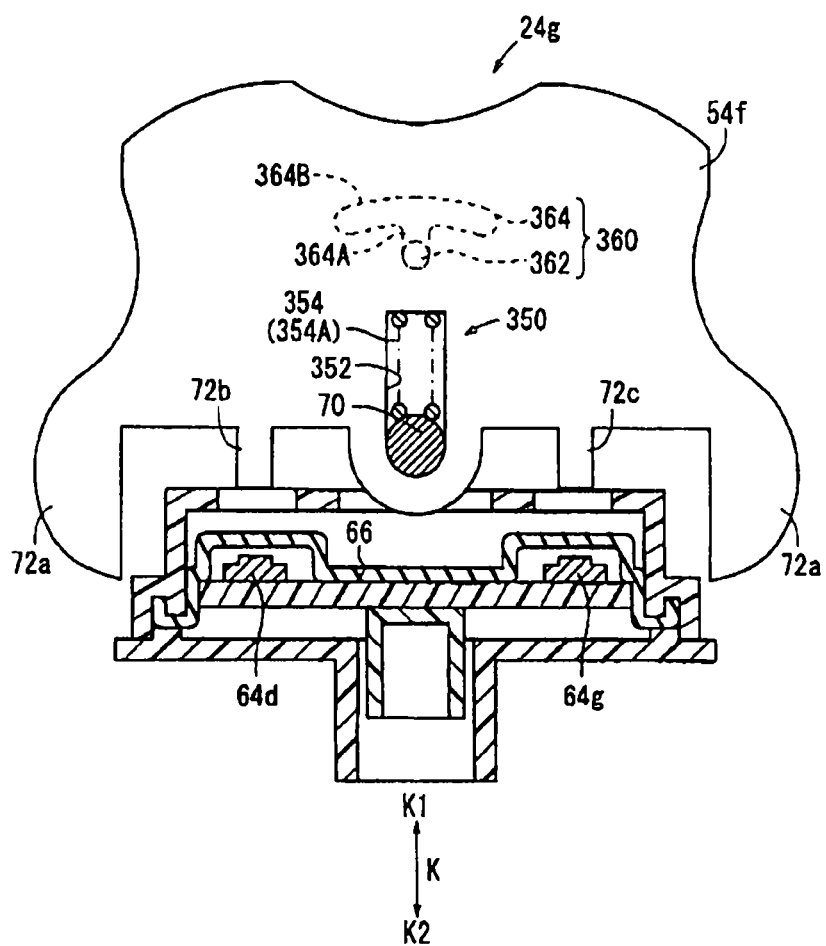
FIG. 46 is a sectional view of a part of a composite input unit according to a ninth modification when the rotation operating part is in the non-operating position.

FIG. 46 is a sectional view showing a part of a composite input unit 24g according to a ninth modification when a rotation operating unit 54f is in a non-operating position.

Figure 47:
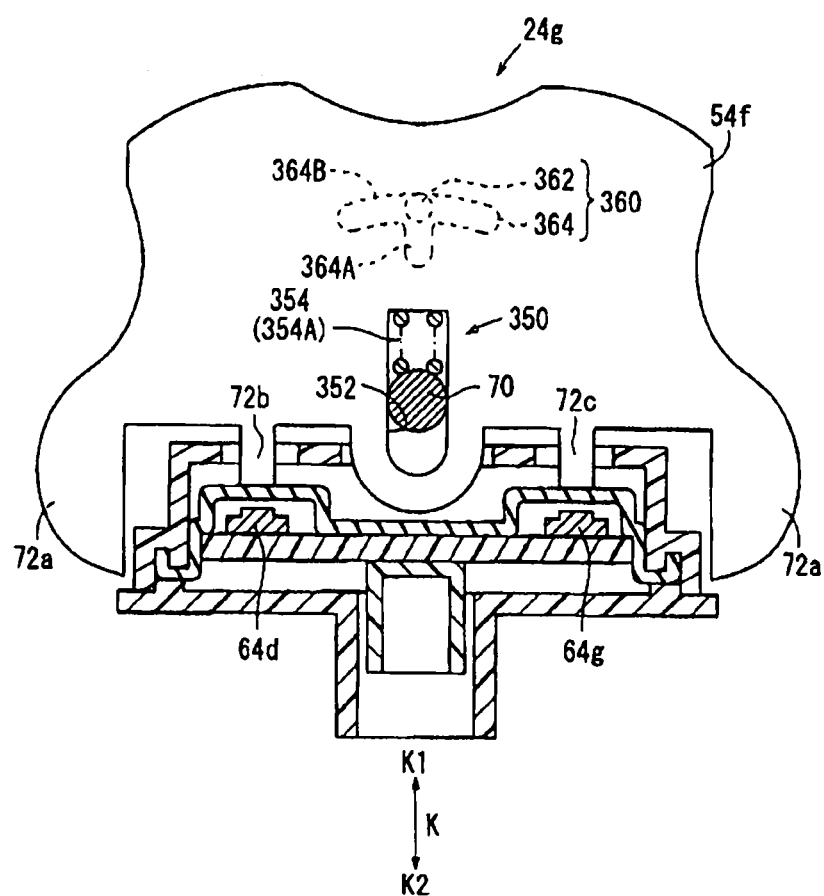
FIG. 47 is a sectional view of a part of the composite input unit according to the ninth modification when the rotation operating part is in the operating position.

FIG. 47 is a sectional view showing a part of the composite input unit 24g according to the ninth modification when the rotation operating part 54f is in an operating position. The composite input unit 24g differs from the composite input unit 24f of the sixth modification only in the configuration of the rotation stopper 360. The rotation stopper 360 here has a pin 362 provided at a position that faces the rotation operating part 54f, and a guide groove 364 provided in the rotation operating part 54f.

The pin 362 is provided at that portion of an operating unit 14 which faces the rotation operating part 54f. The guide groove 364 is provided in a J1-side surface (a surface on the side away from the viewer of FIG. 46) of the rotation operating part 54f. The guide groove 364 is so configured as to inhibit rotation of the rotation operating part 54f when the rotation operating part 54f is in the non-operating position, and as to permit rotation of the rotation operating part 54f when the rotation operating part 54f is in the operating position. For this purpose, the guide groove 364 has a vertical groove 364A extending in the K direction, and an arcuate groove 364B extending along an arc of a circle which has a radius coinciding with the line segment interconnecting the center of a shaft 70 and the center of the pin 362.

As shown in FIG. 46, when the rotation operating part 54f is located in the non-operating position, an attempt to rotate the rotation operating part 54f to the left side or the right side cannot yield a rotation of the rotation operating part 54f, since the pin 362 is located within the vertical groove 364A. On the other hand, as shown in FIG. 47, when the rotation operating part 54f has been moved downward and is located in the operating position, the pin 362 is located within the arcuate groove 364B, so that the rotation operating part 54f can be rotated to the left side and to the right side.

The rotation stopper 360 configured in this manner functions like the above-described rotation stopper 356. Specifically, the operator attempting to operate the rotation operating part 54f can recognize that the rotation operating part 54f is located in the non-operating position, based on the fact that the rotation operating part 54f cannot be rotated. Therefore, the operator can easily understand that it is necessary to push the rotation operating part 54f in the K2 direction, in order to obtain a condition in which the turning mechanism can be operated.

Figure 48:
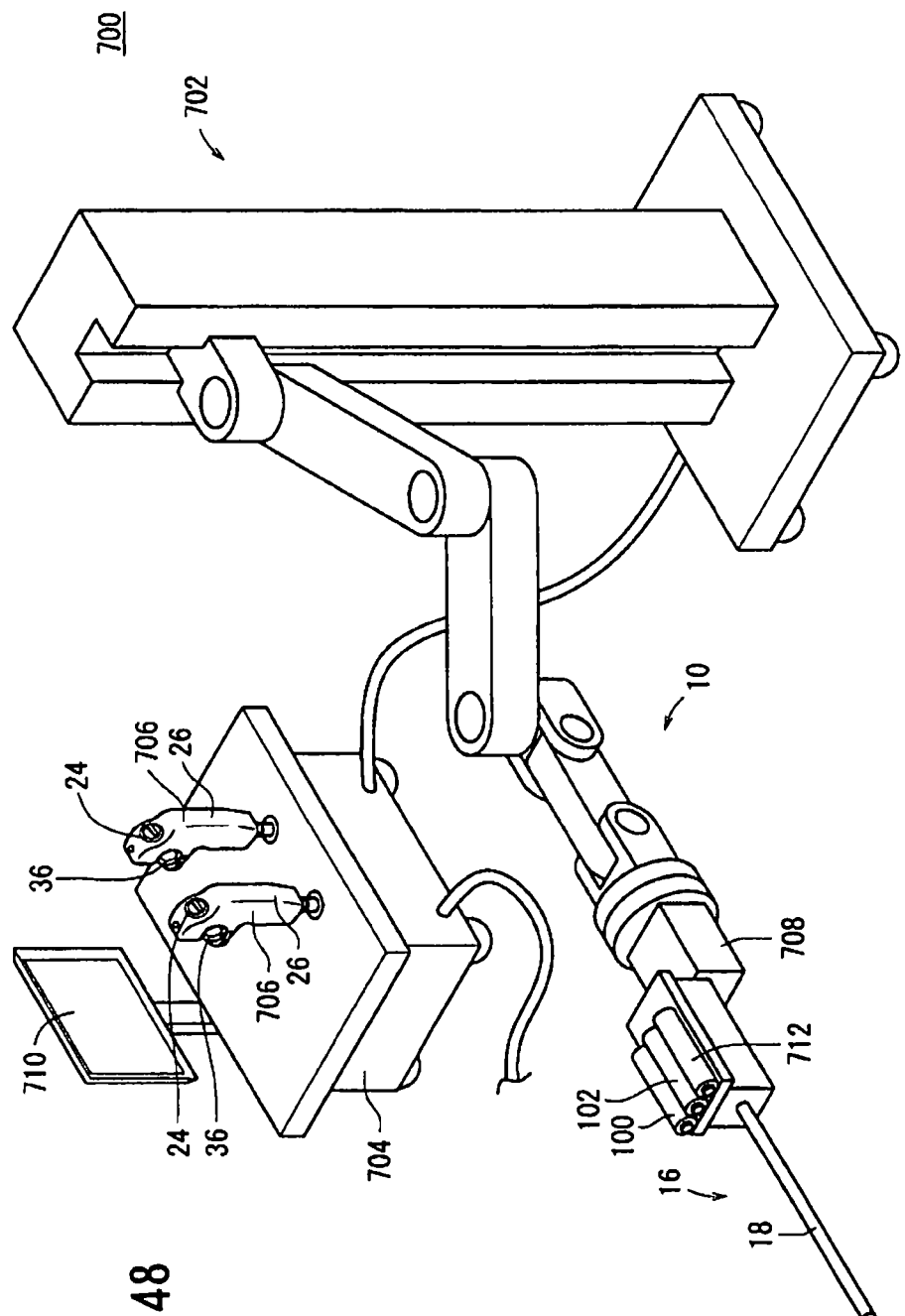
FIG. 48 is a schematic perspective view of a surgical robot system in which the working unit is connected to a distal end of a robot arm.

The present invention is applicable also to a surgical robot system 700 as shown in FIG. 48, for example.

The surgical robot system 700 has a robot arm 702 of an articulate type, and a console 704, with a working unit 16 connected to the distal end of the robot arm 702. The same mechanism as the above-described manipulator 10 is provided at the distal end of the robot arm 702. It suffices for the robot arm 702 to be mechanism that moves the working unit 16; thus, the robot arm 702 is not limited to a stationary-type one, and may be an autonomous locomotion type one, for example. The console 704 may take any of various configurations such as table type, control panel type, etc.

The robot arm 702 preferably has six or more independent articulations (rotating shafts, slide shafts, or the like) so that the position and orientation of the working unit 16 can be arbitrarily set. The manipulator 10 at the distal end is united with a distal portion 708 of the robot arm 702. The manipulator 10 has a motor (an actuator interlocking with an input unit operated by hand) 712 in place of the above-described trigger lever 36, and two rods 192a and 192b are driven by the motor 712.

The robot arm 702 is operated under operations on the console 704. Specifically, the robot arm 702 may be so configured as to perform automatic motions according to programs, motions imitating those of a joystick 706 provided at the console 704, and composite motions of these motions. The console 704 includes the functions of the above-mentioned controller. The working unit 16 is provided with the above-described end effector 12.

The console 704 is provided with two joysticks 706 as an operation command unit, and a monitor 710. Although not illustrated in the drawings, two robot arms 702 can be individually operated by use of the two joysticks 706. The two joysticks 706 are provided at such positions as to permit easy operation thereof by both hands. Information such as an image captured by a flexible endoscope is displayed on the monitor 710.

The joystick 706 can perform vertical motions, leftward and rightward motions, twisting motions, and tilting motions, and the robot arm 702 can be moved according to these motions of the joystick 706. The joystick 706 may be a master arm. The communication between the robot arm 702 and the console 704 can be achieved by wired communication, wireless communication, network communication, or a combination of them.

The joystick 706 is provided with a trigger lever 36, and the motor 712 can be driven by operating the trigger lever 36.

As has been described above, according to the manipulator 10 in the embodiments of the present invention, the motors 100 and 102 that drive the end effector 12 are arranged in parallel to the connector shaft 18, whereby the degree of freedom in layout is enhanced, and, for example, they can be disposed near the grip handle 26. This ensures mass concentration into the vicinity of the grip handle 26, reduces the burden on the operator's hand, and enhances operability. In addition, the moment of inertia about the connector shaft 18 is reduced, which also contribute to enhancement of operability. The motors 100 and 102 remain compact, without protruding sideways.

In the proximal portion of the manipulator 10, the motors 100 and 102 and the grip handle 26 are comparatively large in weight and volume. The motors 100, 102 and the grip handle 26 are disposed on the opposite sides (the Y1 and Y2 sides) with reference to the axis of the connector shaft 18, and the motors 100 and 102 are juxtaposed in the direction away from the viewer of the drawings (in the X direction), whereby good balance is ensured, the degree of freedom in layout is enhanced, and operability is further enhanced. In this case, the juxtaposed arrangement of the motors 100 and 102 is not limited to an arrangement in which the motors 100 and 102 are strictly juxtaposed without any stagger. For example, where the motors 100 and 102 are somewhat different in length, it suffices for the motors 100 and 102 to be juxtaposed at their portions of not less than half their lengths.

Furthermore, the motors 100 and 102 and the grip handle 26 are disposed on the further proximal side (Z2 side) relative to a proximal portion of the connector shaft 18. This ensures that the motors 100 and 102 and the grip handle 26 are disposed close to each other, further concentration of mass is promised, operability is further enhanced, and the manipulator 10 can be easily used by an operator accustomed to conventional forceps.

Obviously, numerous modifications and variations of the present invention are possible in light of the above teachings. It is therefore to be understood that within the scope of the appended claims, the invention may be practiced otherwise than as specifically described herein.

The invention claimed is:

1. A handheld medical manipulator comprising:
   an end effector that performs motions with respect to at least two different axes, and that is inserted in a body cavity during operation of the medical manipulator;
   a cylindrical motor including a longitudinal axis, the motor driving at least a part of the end effector, the motor remaining outside the body cavity during operation of the medical manipulator and being mounted on at least one bracket and, the motor including a drive mechanism and a drive shaft that extends substantially perpendicular to the longitudinal axis of the motor, the drive shaft including a driven mechanism that engages the drive mechanism of the motor;
   a connector shaft that interconnects the bracket and the end effector, a longitudinal axis of the connector shaft extending substantially parallel to the longitudinal axis of the motor; and
   a grip handle that is gripped during operation of the medical manipulator, the grip handle being positioned on a proximal side of the medical manipulator.

2. The handheld medical manipulator according to claim 1,
   wherein the motor is positioned in a first direction, and
   wherein the grip handle and the motor are disposed on opposite sides of the longitudinal axis of the connector shaft with respect to a second direction that is substantially perpendicular to the first direction and the longitudinal axis of the connector shaft.

3. The handheld medical manipulator according to claim 2, wherein the motor and the grip handle are disposed on the medical manipulator proximal of a proximal portion of the connector shaft.

4. The handheld medical manipulator according to claim 1,
   wherein the drive shaft is a rotator provided for the motor, the motor being disposed in a first direction, the rotator being disposed so as to rotate about a center axis that extends in a second direction that is substantially perpendicular to the first direction and the longitudinal axis of the motor, and the rotator including a driven bevel gear that is driven by a drive bevel gear of the motor;
   a flexible member that is partly wrapped around the rotator and passes through the connector shaft so as to transmit motive power to the end effector; and
   a guide unit that guides the flexible member to a proximal opening of the connector shaft.

5. The handheld medical manipulator according to claim 4, wherein the guide unit includes a pulley that includes an axis of rotation that is substantially parallel to the center axis of rotation of the rotator.

6. The handheld medical manipulator according to claim 5, wherein:
   the pulley includes a two-idler structure, the two idlers respectively corresponding to a forward line and a return line, and the two idlers being independently rotatable.

7. The handheld medical manipulator according to claim 4, wherein:
   the rotator is rotatably borne by a pair of bearing members on opposite sides with reference to an area where a corresponding driven bevel gear is provided;
   the bracket comprises a motor plate and the motor is fixed to the motor plate which interconnects the pair of bearing members; and an output shaft of the motor protrudes through a hole provided in the motor plate and is connected to the corresponding driven bevel gear through the corresponding drive bevel gear.

8. The handheld medical manipulator according to claim 7, further comprising a reinforcement plate that interconnects the pair of bearing members and the motor plate.

9. The handheld medical manipulator according to claim 4, wherein:
the guide unit and a portion of the rotator around which the flexible member is wound are provided in a cavity of a box into which a proximal portion of the connector shaft opens; and
the rotator is rotatably sealed in an airtight relationship with respect to the cavity.

10. The handheld medical manipulator according to claim 1, wherein:
the end effector changes a direction when driven by the motor, and the end effector is driven by being mechanically connected to an input unit that is operated by a hand.

11. The handheld medical manipulator according to claim 10, wherein:
a rod protrudes to a proximal side of the medical manipulator from an inside of the connector shaft, the rod being connected to the input unit, and the rod advancing and retracting in a direction of the connector shaft; and
the rod is mounted so as to advance and retract in relation to the connector shaft and a space with which the connector shaft communicates while maintaining a sealed air-tight relationship with the space.

12. The handheld medical manipulator according to claim 1, further comprising a trigger lever including a finger ring part disposed adjacent to the grip handle.

13. The handheld medical manipulator according to claim 12, wherein the trigger lever further comprises a finger holder protrusion attached to a first side of the finger ring part, and a ratchet release that is integral with a ratchet pawl that assists in actuating end effector elements in combination with use of the trigger lever.

14. The handheld medical manipulator according to claim 13, wherein the ratchet release is disposed within the finger holder protrusion so as to be partly exposed in a first position.

15. A handheld medical manipulator comprising:
an end effector that performs motions with respect to at least two different axes, the end effector having forceps that are inserted in a body cavity during operation of the medical manipulator;
a cylindrical motor having a longitudinal axis, the motor driving at least a part of the end effector, the motor remaining outside the body cavity during operation of the medical manipulator; the motor driving the end effector to change a direction;
a drive shaft that extends substantially perpendicular to the longitudinal axis of the motor, the drive shaft including a driven mechanism that engages the drive mechanism of the motor;
a connector shaft that interconnects the end effector, a longitudinal axis of the connector shaft extending substantially parallel to the longitudinal axis of the motor;
a grip handle that is gripped during operation of the medical manipulator, the grip handle positioned on a proximal side of the medical manipulator, the motor and the grip handle disposed on opposite sides of the connector shaft;
a trigger lever including a finger ring part disposed adjacent to the grip handle that mechanically drives the forceps when operated by a hand.

16. A handheld medical manipulator comprising:
an end effector that performs motions with respect to at least two different axes, the end effector having forceps that are inserted in a body cavity during operation of the medical manipulator;
a cylindrical motor having a longitudinal axis, the motor driving at least a part of the end effector, the motor remaining outside the body cavity during operation of the medical manipulator;
a drive shaft that extends substantially perpendicular to the longitudinal axis of the motor, the drive shaft including a driven mechanism that engages the drive mechanism of the motor;
a connector shaft that interconnects the end effector, a longitudinal axis of the connector shaft extending substantially parallel to the longitudinal axis of the motor;
a grip handle that is gripped during operation of the medical manipulator, the grip handle positioned on a proximal side of the medical manipulator;
wherein the drive shaft is a rotator provided for the motor, the motor being disposed in a first direction, the rotator being disposed so as to rotate about a center axis that extends in a second direction that is substantially perpendicular to the first direction and the longitudinal axis of the motor, and the rotator including a driven bevel gear that is driven by a drive bevel gear of the motor;
a flexible member that is partly wrapped around the rotator and passes through the connector shaft so as to transmit motive power to the end effector; and
a guide unit that guides the flexible member to a proximal opening of the connector shaft.

* * * * *